(12) United States Patent
Nozaki et al.

(10) Patent No.: US 11,024,031 B1
(45) Date of Patent: Jun. 1, 2021

(54) SYSTEM AND METHOD FOR DIAGNOSING SEVERITY OF GASTRIC CANCER

(71) Applicant: OLYMPUS CORPORATION, Hachioji (JP)

(72) Inventors: Hirokazu Nozaki, Hachioji (JP); Wataru Hashimoto, Kawasaki (JP); Takashi Suzuki, Hino (JP); Mitsunori Kubo, Hachioji (JP); Yusuke Kuwa, Hachioji (JP); Yuji Sakamoto, Kunitachi (JP); Mariko Otagiri, Sagamihara (JP); Naoki Yoshida, Mitaka (JP); Yoji Watanabe, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/790,068

(22) Filed: Feb. 13, 2020

(51) Int. Cl.
| | | |
|---|---|---|
| *G06K 9/00* | (2006.01) | |
| *G06T 7/00* | (2017.01) | |
| *G06T 5/50* | (2006.01) | |
| *A61B 1/06* | (2006.01) | |
| *A61B 1/273* | (2006.01) | |

(52) U.S. Cl.
CPC .......... *G06T 7/0016* (2013.01); *A61B 1/0638* (2013.01); *A61B 1/2736* (2013.01); *G06T 5/50* (2013.01); *G06T 2207/10068* (2013.01); *G06T 2207/10081* (2013.01); *G06T 2207/10088* (2013.01); *G06T 2207/20081* (2013.01); *G06T 2207/30092* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 8,010,381 B2 | 8/2011 | Sirohey et al. | |
| 2006/0247514 A1* | 11/2006 | Panasyuk | A61B 5/0059 600/410 |
| 2013/0293693 A1* | 11/2013 | Igarashi | H04N 7/183 348/70 |
| 2019/0223690 A1* | 7/2019 | Yamamoto | A61B 1/045 |

FOREIGN PATENT DOCUMENTS

JP  H08266485 A  * 10/1996  ............... A61B 5/00

* cited by examiner

*Primary Examiner* — Atiba O Fitzpatrick
(74) *Attorney, Agent, or Firm* — Oliff PLC

(57) ABSTRACT

A diagnostic system, method, and a computer-readable storage medium for determining a severity of a gastric condition, such as gastric cancer, in a subject are disclosed. The diagnostic system includes a processor that can obtain various images of a stomach of the subject including wavelength images and generate difference images from the wavelength images. The processor can compare the subject images with reference images representative of different severity levels of gastric cancer, or can input the subject images into a learned model trained using the reference images stored in the database to extract a feature pattern corresponding to a severity of gastric cancer to diagnose the subject as having a particular severity level of gastric cancer.

20 Claims, 40 Drawing Sheets

SYSTEM AND METHOD FOR DIAGNOSING SEVERITY OF GASTRIC CANCER

BACKGROUND

Gastric conditions, including gastric atrophy, gastritis, and gastric cancer, affect millions of people. Gastric cancer is the most common form of digestive system malignant tumor among Japanese people. Gastric cancer and other gastric conditions can be cured by early detection and treatment. However, many cases are detected in an advanced state, resulting in a poor prognostic outcome.

Endoscopic examination and imaging offer opportunities for early detection. For example, with an endoscopic apparatus, a doctor can observe the organs in the body cavity and make a diagnosis by inserting the elongated insertion portion into the body cavity and using a solid-stage imaging element or the like as an imaging means. However, final diagnoses using these medical imaging apparatuses are mainly based on determinations by doctors, which are inherently subjective. For example, variations in experience and knowledge between doctors may result in inconsistent diagnoses.

SUMMARY

The present systems and methods provide quantitative and objective diagnostic support information via image processing to facilitate consistent and accurate diagnoses of gastric conditions, such as gastric cancer and the severity thereof.

The disclosed embodiments include a diagnostic system for determining a severity of gastric cancer in a subject, a method for determining a severity of gastric cancer in a subject, and a computer-readable storage medium storing a computer-executable program that causes a computer to perform functions for determining a severity of gastric cancer in a subject. The severity of gastric cancer may include determining a stage of gastric cancer.

The diagnostic system according to the disclosed embodiments includes a processor programmed to obtain various images of a stomach of the subject including wavelength images, and generate difference images from the wavelength images. The processor is programmed to compare the subject images with reference images representative of different severity levels of gastric cancer, or input the subject images into a learned model trained using the reference images stored in the database to extract a feature pattern corresponding to a severity of gastric cancer to diagnose the subject as having a particular severity level of gastric cancer.

The method for determining a severity of gastric cancer in a subject may include obtaining various images of a stomach of the subject including wavelength images, and generating difference images from the wavelength images. The subject images may then be compared with reference images representative of different severity levels of gastric cancer, or input into a learned model trained using the reference images stored in the database to extract a feature pattern corresponding to a severity of gastric cancer to diagnose the subject as having a particular severity level of gastric cancer.

A computer-readable storage medium according to the disclosed embodiments stores a computer-executable program that causes a computer to perform functions, such as obtaining various images of a stomach of the subject including wavelength images, generating difference images from the wavelength images, and comparing the subject images with reference images representative of different severity levels of gastric cancer, or inputting the subject images into a learned model trained using the reference images stored in the database to extract a feature pattern corresponding to a severity of gastric cancer to diagnose the subject as having a particular severity level of gastric cancer.

DETAILED DESCRIPTION

It will be apparent to the skilled artisan in the medical field from this disclosure that the following descriptions of exemplary embodiments are provided as examples only and need not limit the broad inventive principles described herein or included in the appended claims.

The present disclosure relates to a diagnostic system, non-transitory computer-readable storage medium, and method for determining a severity of a gastric condition of a subject based on image and non-image data. For example, the present disclosure relates to comparing an image of the stomach of the subject with a standard stomach image of a healthy stomach to generate a subject abnormality image. The subject abnormality image may then be compared with reference abnormality images of stomachs representative of different severity levels of gastric conditions. The subject may be then diagnosed based at least in part on the comparison between the subject abnormality image and the reference abnormality images as having a particular severity level of a gastric condition. As discussed in more detail below, the system and the associated computer-readable storage medium and method enable consistent and accurate diagnoses of the severity of gastric conditions.

Figure 1:
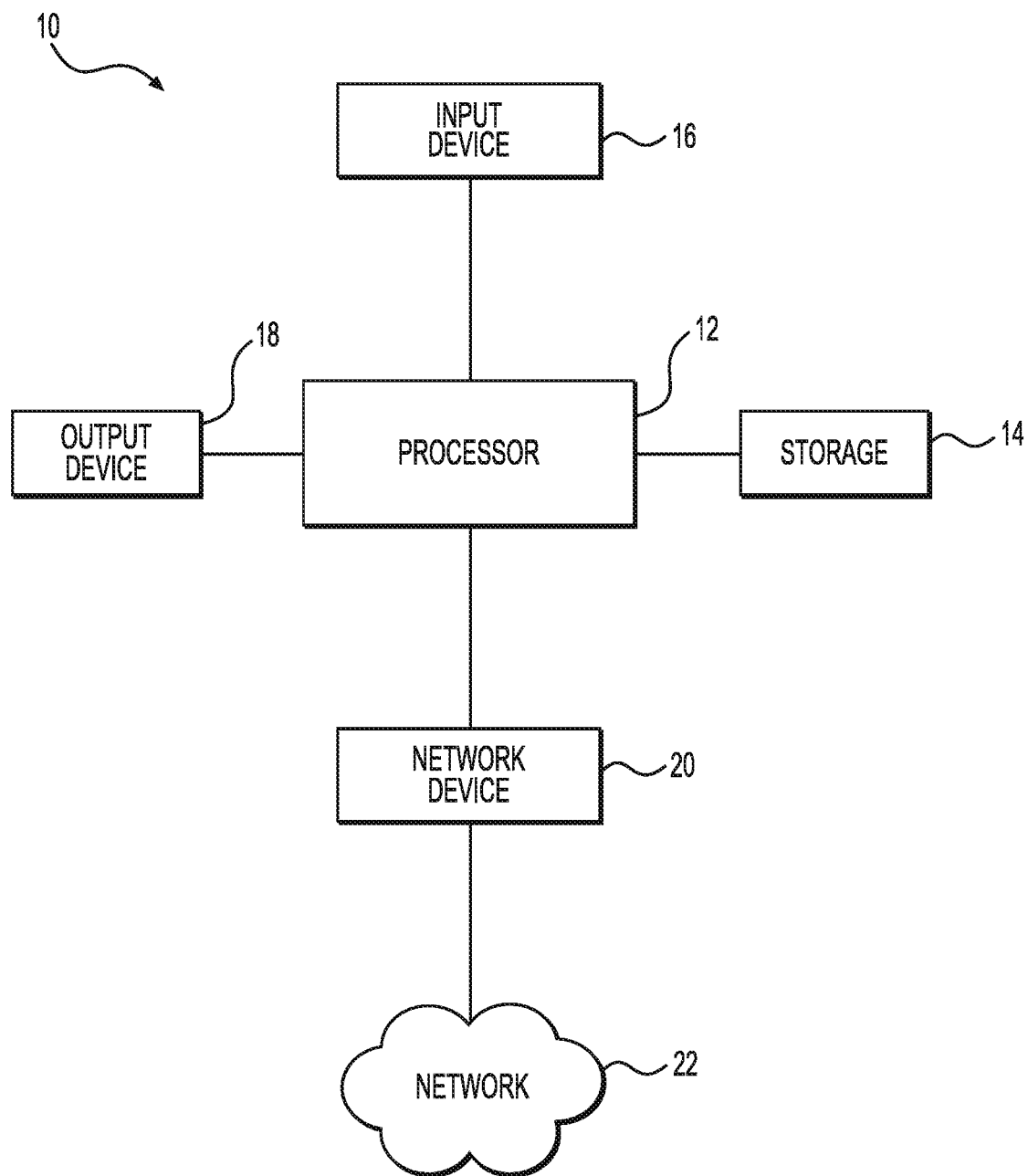
FIG. 1 is a block diagram of an exemplary diagnostic processor system.

FIG. 1 shows an exemplary processor system 10 for use in connection with diagnosing severity levels of gastric conditions. The processor system 10 may be a general-purpose computer, such as a personal computer, tablet, or mobile device, a specific-purpose computer or workstation, a mainframe computer, or a distributed computing system. The processor system 10 is configured to execute various software programs, including software performing all or part of the processes and algorithms disclosed herein. The exemplary processor system 10 includes a controller or processor 12 that is configured to process data, such image and non-image information received as inputs for various algorithms and software programs. The processor 12 may include hardware, and the hardware may include at least one of a circuit for processing digital signals and a circuit for processing analog signals, for example. The processor may include one or a plurality of circuit devices (e.g., an IC) or one or a plurality of circuit elements (e.g., a resistor, a capacitor) on a circuit board, for example. The processor 12 may be a central processing unit (CPU), and/or various types of processors, including a GPU (Graphics Processing Unit) and a DSP (Digital Signal Processor), may be used. The processor may be a hardware circuit with an ASIC (Application Specific Integrated Circuit) or an FPGA (Field-Programmable Gate Array). The processor may include an amplification circuit, a filter circuit, or the like for processing analog signals.

The processor 12 may execute operating system instructions, along with software algorithms, computer-executable instructions, and processing functions of the system 10. Such algorithms and computer-executable instructions may be stored in a computer readable-storage medium, such as storage 14. "Computer readable-storage medium" as used herein refers to a non-transitory computer readable storage medium. The system 10 may include one or more storage devices 14. The storage 14 may include a memory and/or other storage device. The memory may be, for example, random-access memory (RAM) of a computer. The memory may be a semiconductor memory such as an SRAM and a DRAM. The storage device may be, for example, a register, a magnetic storage device such as a hard disk device, an optical storage device such as an optical disk device, an internal or external hard drive, a server, a solid-state storage device, CD-ROM, DVD, other optical or magnetic disk storage, or other storage devices. Computer-executable instructions include, for example, instructions and data which cause the processor system 10 to perform a certain function or group of functions. When the instructions are executed by the processor 12, the functions of each unit of the system and the like are implemented. The instructions may be a set of instructions constituting a program or an instruction for causing an operation on the hardware circuit of the processor.

Data, including subject image data, subject non-image data, and other data, such as reference images, reference abnormality images, and standard images may be stored in a database in the storage 13, such as the memory or another storage device. Such data may also be provided to the processor 12 by an input device 16, such as a keyboard, touchscreen, mouse, data acquisition device, network device, or any other suitable input device. Exemplary data acquisition devices may include an imaging system or device, such as an endoscope, a subject monitor, or any other suitable system or device capable of collecting or receiving data regarding the subject. Subject data may include image data and/or non-image data, and may include any of static data, dynamic data, and longitudinal data. For example, subject images collected by an endoscope may be provided to the processor to diagnose a severity of a gastric condition. Data, such as subject, standard, and reference images, as well as non-image data may be stored in a database or various databases accessible by the processor 12. The processor may be configured to implement a deep learning process described in detail below to generate normal image data.

The various components of the diagnostic system 10 and the like may be connected with each other via any types of digital data communication such as a communication network 22. Data may also be provided to the processor system 10 through a network device 20, such as a wired or wireless Ethernet card, a wireless network adapter, or any other devices designed to facilitate communication with other devices through a network 22. The network 22 may be, for example, a Local Area Network (LAN), Wide Area Network (WAN), and computers and networks which form the Internet. The system 10 may exchange data and communicate with other systems through the network 22. Although the system shown in FIG. 1 is shown as being connected to a network, the system may be also be configured to work offline.

Results, including diagnoses of a severity of a gastric condition output by the processor 12 may be stored in accordance with one or more algorithms in one or more storage devices 14, such as memory, may undergo additional processing, or may be provided to an operator via an output device 18, such as a display and/or a printer. Based on the displayed or printed output, an operator may request additional or alternative processing or provide additional or alternative data, for example, via an input device 16.

Figure 2:
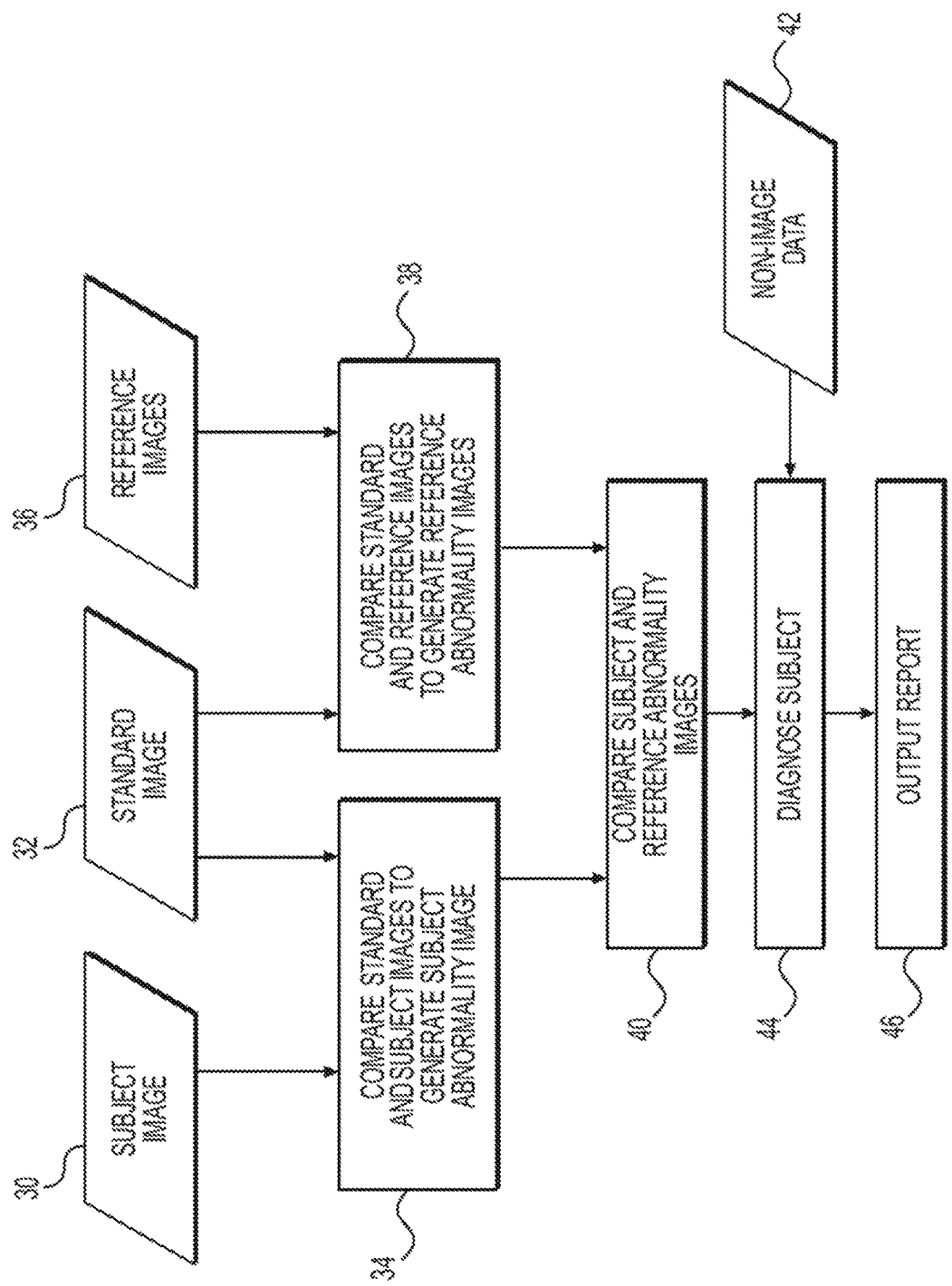
FIG. 2 is a flow chart of an exemplary diagnosis method.

FIG. 2 shows an exemplary method for diagnosing a subject as having a particular severity of a gastric condition based on image abnormality data. Gastric conditions may include, for example, gastric atrophy, gastritis, and gastric cancer. As shown in FIG. 2, a subject image 30 of a stomach of the subject is obtained. The subject image 30 is compared with a standard image 32 to generate a subject abnormality image 34, which is indicative of differences between the subject image and the standard image. The subject image 30 may be an image collected by an endoscope and may be processed to improve contrast and/or extract or enhance features. The standard image is an image of a stomach in a healthy state. The standard image may be an earlier image of the subject in a healthy state or may be an image of a stomach of a different person in a healthy state. As discussed in more detail below, the different person may be selected based on one or more shared characteristics with the subject, such as age, race, and sex.

Further with respect to FIG. 2, reference images 36 of stomachs exhibiting different severity levels of various gastric conditions are also compared to the standard image to generate reference abnormality images 38, which are indicative of differences between the reference images and the standard image. Reference images 36 may be standardized images acquired from a database of reference images for each diagnosed condition or disorder collected from a particular group of people diagnosed with such conditions, as discussed above. The reference images 36 may be the actual images, optionally processed to enhance the structural feature of interest, collected from the people of a particular group or characteristic category. Alternatively, the reference images 36 may be average images created based on the data collected from the people of a particular population diagnosed with such conditions. For example, a representative average stomach image for each gastric condition may be generated. Additionally, representative average stomach images corresponding to various severity levels within a particular gastric condition may also be generated. Thus, multiple representative or average images may be created for each gastric condition and severity level.

The subject abnormality image 34 is then compared 40 with the reference abnormality images 38. All of the images may be standardized into one or more common or similar formats to facilitate analysis and comparison. The subject is diagnosed 44 as having a particular severity level of a gastric condition based at least on part on the comparison between the subject abnormality image the reference abnormality images. The diagnosis 44 may also be made by taking other data 42 and analysis into consideration, including non-image data, such as clinical data, laboratory data, subject history, family history, subject vital signs, results of various tests (e.g., genetic tests), and any other relevant non-image data. Based on the subject and reference data, numerous reference and subject abnormality data and images may be created. Then, a report 46 of the diagnosis 44 is output to an output device 18 (shown in FIG. 1), such as a display or a printer, or may be output to a database for storage, or to a user in a human-readable format.

The various images and data described herein may be stored in one or more databases to facilitate subsequent data analysis. Moreover, any or all of the foregoing comparisons may be performed either automatically by a data processing system, such as system 10, or by a medical professional, such as a doctor, or by some combination thereof, to facilitate automatic or manual diagnosis of the subject in step 44.

The abnormality images described herein may be generated through any suitable technique. For example, an abnormality image may be a difference image between two or more images. A subject abnormality image may be created by subtracting a standard image from a subject image. Likewise, reference abnormality images may be generated by subtracting a standard image from each of the reference images. The resulting difference (abnormality) images show the differences between the subject and reference images and the standard image. By eliminating normal features through subtractive processing, the difference images make it easier to identify areas of abnormalities or deviations from normal. For example, the difference images allow a user to focus on, extract, and enhance the deviations and abnormalities in the subject image that may not be as apparent from a comparison of the raw subject images with the standard images. In the absence of differential imaging, it is often difficult to identify the extent of deviation in a subject image by simply comparing the subject image and a normal image, for example, in a side-by-side comparison. The difference images enable a user to clearly determine the extent of deviation from the standard images, and accurately diagnose the severity of a particular gastric condition. Using the systems and methods disclosed herein, diagnoses of the severity of various gastric conditions may become more consistent and objective.

Standard images, such as normal reference and normal subject images, may be generated through deep learning techniques. Deep learning is a machine learning technique using multiple data processing layers to recognize various structures in data sets and accurately classify the data sets. For instance, a deep learning model may be trained to generate corresponding normal images from abnormal images, such as reference images indicative of a particular level of severity or an abnormal subject image.

Such a deep learning model may be, for example, an autoencoder network. An autoencoder network has at least three layers: an input layer, a hidden layer for encoding, and an output decoding layer. The autoencoder network may be a variational autoencoder (VAE) model. The VAE is a class of deep generative models that includes an encoder and a decoder.

The model may be trained based on normal training images only. Such normal training images may be images of healthy stomachs that are substantially free of abnormalities. The VAE model is trained via unsupervised learning in which the model extracts and learns features and patterns of the normal training images. That is, the model may analyze raw normal image data to identify features and patterns of normal images without external identification. For example, using backpropagation, the unsupervised algorithm can continuously train itself by setting the target output values to equal the inputs. During training, the VAE can compress (encode) an input normal training image to a small vector of encodings from which it must contain enough information to reconstruct the input image by the decoder. Subsequently, the decoder can expand (decode) the compressed form (output) to reconstruct the input image. The VAE may be trained by comparing the reconstructed output image and the input image in an iterative process to minimize the difference between them. By doing this, the autoencoder is forced to learn features about the image being compressed. Thus, the autoencoder learns features of normal images in an unsupervised manner.

When trained on only normal data, the resulting model is able to perform efficient inference and to determine if a test image is normal or not, as well as to reconstruct an abnormal image into a corresponding normal image. Therefore, once learned, the model can be given an image to predict whether it is normal or abnormal. Because the trained model has been trained using only normal images, it can detect features (e.g., abnormalities) different from the learned normal features (e.g., representative of healthy subjects) as abnormal features.

Additionally, when given an abnormal image, such as a reference image indicative of a particular severity level or an abnormal subject image, the trained model can generate a corresponding normal image. For instance, an abnormal image may be obtained and compressed with the encoder. Using the decoder, the input normal features (encodings) are restored, and the input abnormal features are not restored. Because the trained model has been trained on normal images, normal features of the input abnormal image can be restored, but abnormal features cannot be restored. Rather, abnormal features in the input abnormality image are deleted when the compressed image is restored, and the abnormal feature(s) in the original (input) image are restored as normal feature(s) in the restored image (generated normal image). As such, the restored image produced by the decoder from the compressed image corresponds to the input abnormality image except that an abnormality in the input image is omitted.

Therefore, as discussed below, normal images may be generated from reference images for each severity level by deep learning techniques. Similarly, a normal image may be generated from the subject image. In other words, deep learning may be used to generate normal images that correspond to reference images for each severity level or correspond to the subject image except that abnormal part(s) have been removed. Then, the subject and reference difference images may be obtained by pattern matching. By using deep learning, a pseudo-normal image can be accurately generated, and an accurate difference image can be generated. Additionally, it reduces the amount of data necessary for training the deep learning device or network.

Difference images may be obtained by comparing a subject image and a normal image generated by deep learning. Reference difference images may also be obtained by comparing reference images indicative of various severity levels to normal images generated by deep learning techniques. The difference images may be raw difference images or they may be processed or manipulated to filter out noise or movement and increase the dynamics of effect, e.g., of different pixel values to illustrate abnormalities or deviations in the area of interest. The difference images may be further processed to smooth out the image and remove high frequency noise. For example, a lowpass spatial filter can block high spatial frequencies and/or low spatial frequencies to remove high frequency noises at either end of the dynamic range. This provides a smoothed-out processed difference image (in digital format).

In another aspect, reference data, including image and non-image data, may be collected from people or groups of people. Such people may include healthy people that are not suffering from a gastric condition, and other people suffering from various gastric conditions and severity levels thereof, including, for example, gastric atrophy, gastritis, and gastric cancer. The reference image and non-image data may be standardized and categorized according to one or more characteristics. For example, such reference data may be categorized based on population characteristics, such as race, gender, or age of the people from which the data was collected. Standardized data permits average stomach characteristics to be calculated for healthy subjects and subjects with different severity levels of each particular gastric condition.

Figure 3:
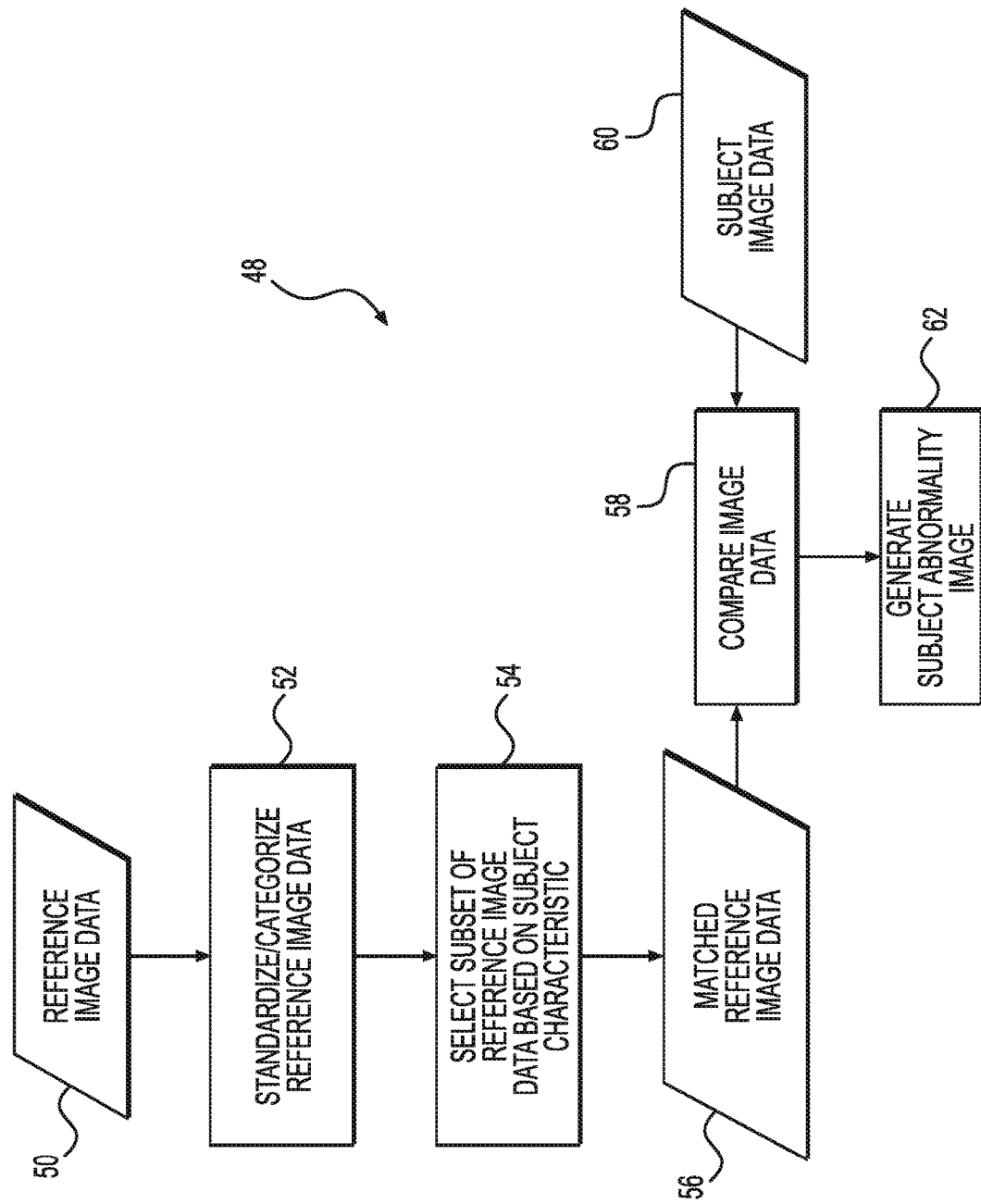
FIG. 3 is a flow chart of an exemplary method for generating subject abnormality images.

An exemplary method 48 for generating abnormality images, indicative of differences between a region of the subject's stomach and a reference stomach region, is illustrated in FIG. 3. Reference image data is acquired in step 50. Reference image data 50 may include standard image data of healthy, normal subjects, and reference image data of subjects with various gastric conditions and severity levels thereof. The reference image data may be categorized and standardized in step 52. For example, reference image data may be categorized and/or standardized according to one or more desired characteristics, such as age, gender, or race. While the presently illustrated embodiment is described with respect to image data, it is noted that reference non-image data and subject non-image data may also, or instead, be used to generate the abnormality images discussed herein.

The method 48 may include a step 54 of selecting a subset of the reference image data based on a subject characteristic. For instance, if a subject is a thirty-five year old Japanese man, a subset of the reference image data grouped to include reference images pertaining to men between thirty and forty years of age may be more relevant for comparative purposes than a group of reference images composed of data collected from men between sixty and seventy years of age. Similarly, a subset of the reference image data grouped to include reference images pertaining to Japanese men may be more relevant for comparative purposes than a group of reference images composed of data collected from Caucasian men. A subset of reference image data collected from Japanese men between thirty and forty years of age may be the most relevant for comparative purposes.

Once a desired group of reference image data is selected, the matched reference image data 56 may be compared to image data 60 of the subject in step 58. For example, the subject abnormality image may be a difference image between the reference image data 56 and the subject image data 60 may be created. The abnormality image may be generated from a comparison of standard image data of normal, healthy subjects and the subject image data. Non-image data of the subject may instead or also be compared to matched reference non-image data, as described above. Additionally, the various data may be processed and categorized in any suitable manner to facilitate such comparisons.

Figure 4:
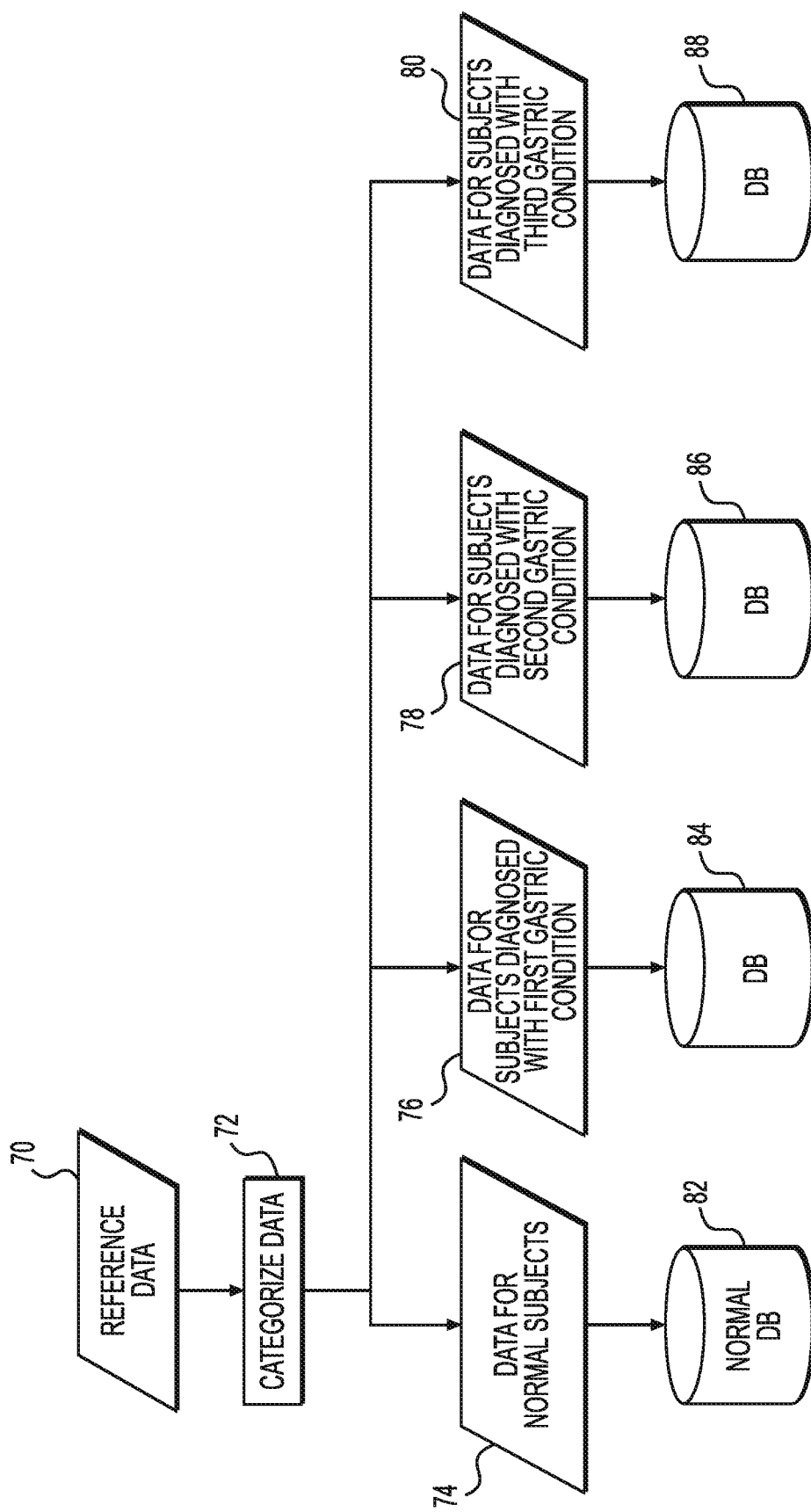
FIG. 4 is a flow chart of an exemplary method for categorizing reference and standard data.

Additionally, reference data may be categorized and sorted into standardized databases, such as through an exemplary method shown in FIG. 4. The method may include acquiring reference data 70, which may include image and non-image data from various people, and categorizing the data in step 72. For example, the reference data 70 may be categorized into various groups, such as normal (healthy) subject data 74, data 76 of subjects clinically diagnosed with a first gastric condition, data 78 of subjects diagnosed with a second gastric condition, and data 80 of subjects diagnosed with a third condition. Such gastric conditions may include, for example, gastritis, including atrophic gastritis, and gastric cancer. The reference data 70 may further be categorized according to severity level for each gastric condition, as discussed in more detail below. The data 74, 76, 78, and 80 may be stored in respective databases 82, 84, 86, and 88. Such databases may be stored on a server, in one or more memory or storage devices, and/or in other suitable media. Such databases may be continuously or periodically updated as more subjects are diagnosed with a particular gastric condition and severity level thereof.

Figure 5:
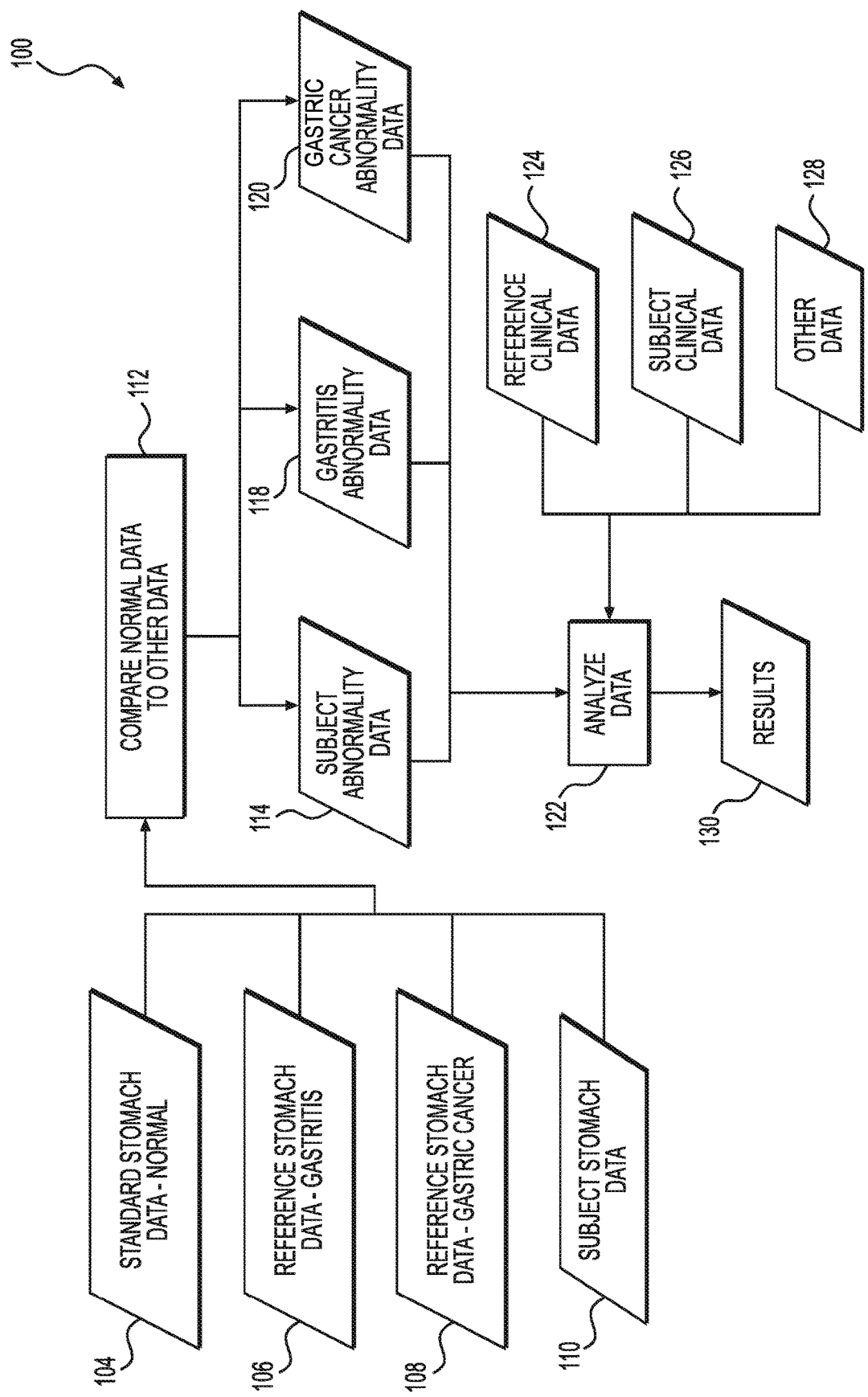
FIG. 5 is a flow chart of an exemplary method for generating and analyzing abnormality data.

Based on the subject and reference image and non-image data discussed above, numerous reference and subject abnormality data and images may be created. By way of example, an exemplary method 100 for generating and analyzing such abnormality data is shown in FIG. 5. The method 100 includes acquiring reference stomach data for: normal subjects without diagnosed gastric conditions (data 104), subjects diagnosed with gastritis, including gastric atrophy (data 106), and subjects diagnosed with gastric cancer (data 108). Each subset of reference stomach data for a particular gastric condition may be further divided into groups based on severity level. The method 100 may also include acquiring subject stomach data 110. The method 100 may acquire reference stomach data for other gastric disorders, which may be processed in a manner similar to those discussed in the present example. Indeed, the present processing techniques may also be applied to other disorders unrelated to the stomach.

In step 112, the standard data 104 may be compared to each of the other data 106, 108, and 110, to generate gastritis abnormality data 118, gastric cancer abnormality data 120, and subject abnormality data 114, all of which may represent deviations from the standard/normal data 104. The abnormality data for each gastric condition may be further divided into groups based on severity level. Such abnormality data may include structural abnormality images representative of differences between the subject data and: (i) the reference data for the particular gastric condition, and (ii) the normal reference data. For example, structural abnormality images may include mucosa thickness images, blood vessel permeation images, lesion size images, and lesion depth images.

In step 122, such abnormality data may be analyzed. For example, a subject abnormality image or data may be compared to representative reference abnormality images or data for each of the above noted gastric conditions to facilitate diagnosis of the subject with respect to one or more of such gastric conditions and a severity level thereof. Additionally, reference clinical data 124, subject clinical data 126, and other data 128 may also be analyzed by a data processing system or a user to facilitate diagnosis. Such analysis may include pattern matching of subject images and reference images, and confidence levels of such matching may be provided to a user. Finally, results 130 of the analysis may be output to storage or to a user via, for example, an output device 18, such as a display or printer.

Figure 6:
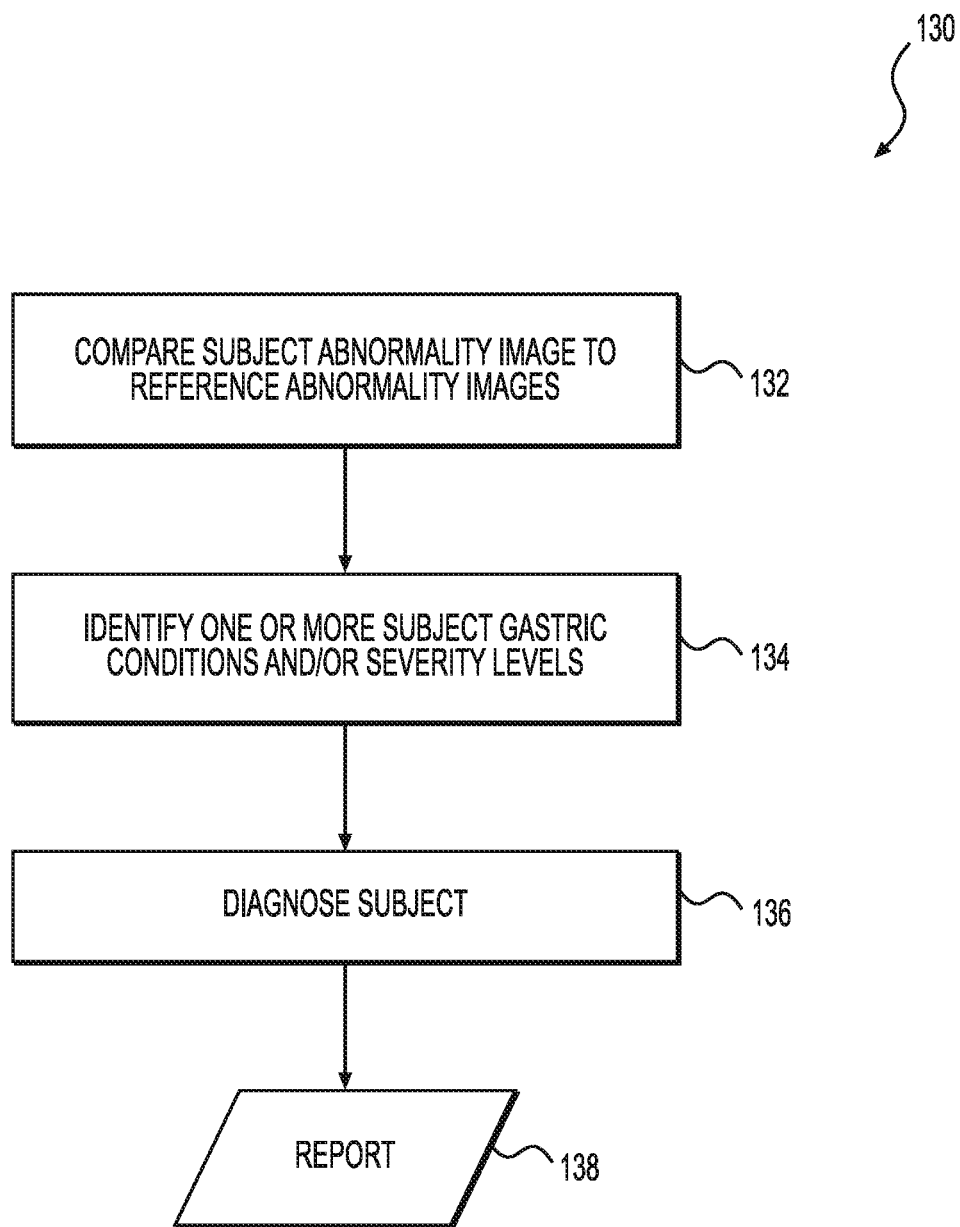
FIG. 6 is a flow chart of an exemplary method for diagnosing a subject based on a comparison of a subject abnormality images and reference abnormality images.

A method 130 for analyzing the data discussed above and diagnosing a subject is illustrated in FIG. 6. In step 132, one or more subject abnormality images, which may include a structural abnormality image or some other abnormality image, may be compared to one or more reference abnormality images, such as those previously described. Notably, the reference abnormality images may include abnormality images representative of one or more gastric conditions, as well as various severity levels of the one or more gastric conditions.

Based on such comparisons, one or more subject gastric conditions and/or severity levels may be identified in step 134 and diagnosed in step 138. In some embodiments, such as a fully automated embodiment, steps 134 and 136 may be combined. In other embodiments, however, the identification and diagnosis may be performed as separate steps. For instance, the data processing system 10 may identify various potential gastric conditions and/or severity levels and present the identified conditions and/or severity levels to a user for diagnosis. A report 138 may include an indication of the identified subject gastric condition(s) or severity levels, the diagnosis, or both.

Figure 7:
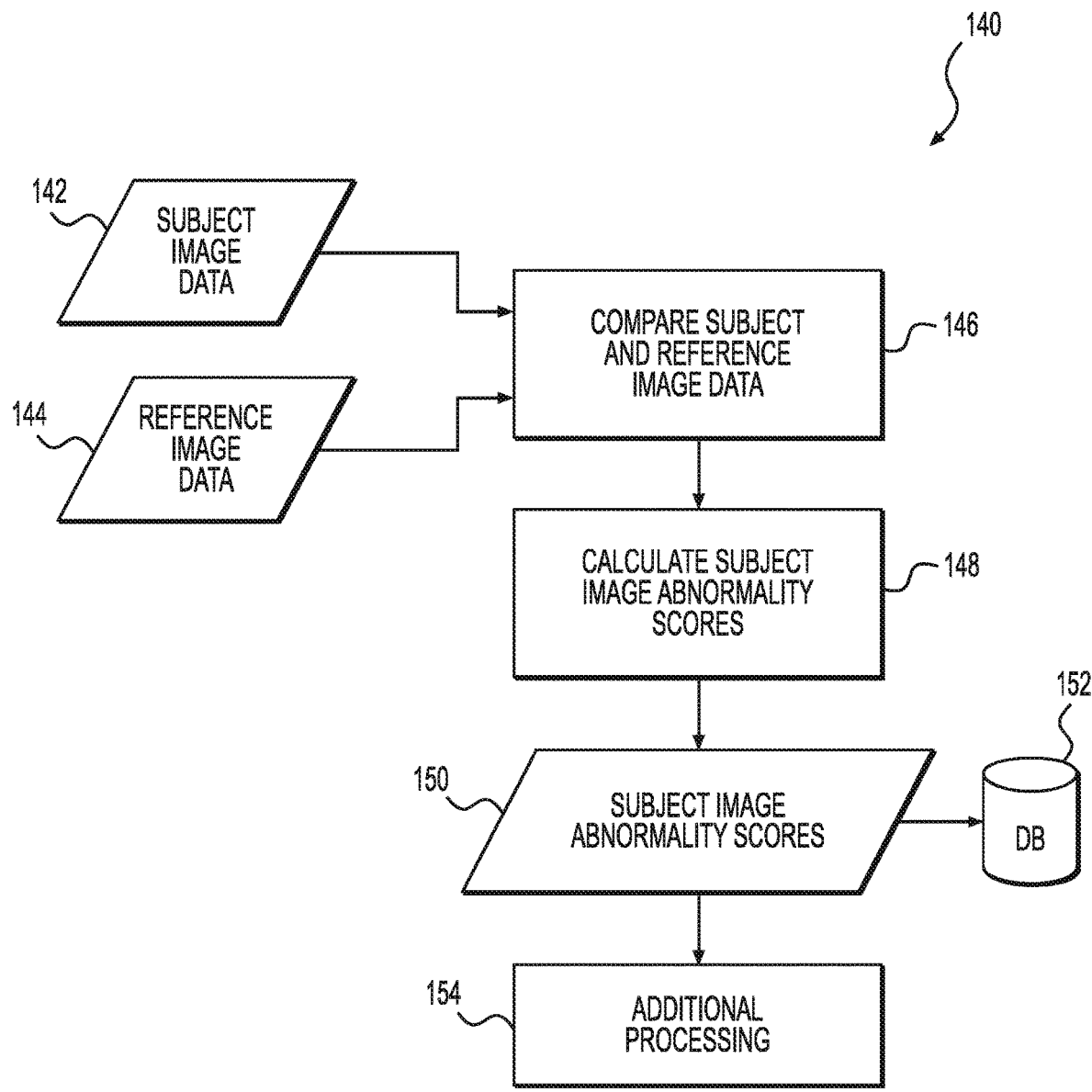
FIG. 7 is a flow chart of an exemplary method for generating abnormality scores for a subject.
Figure 8:
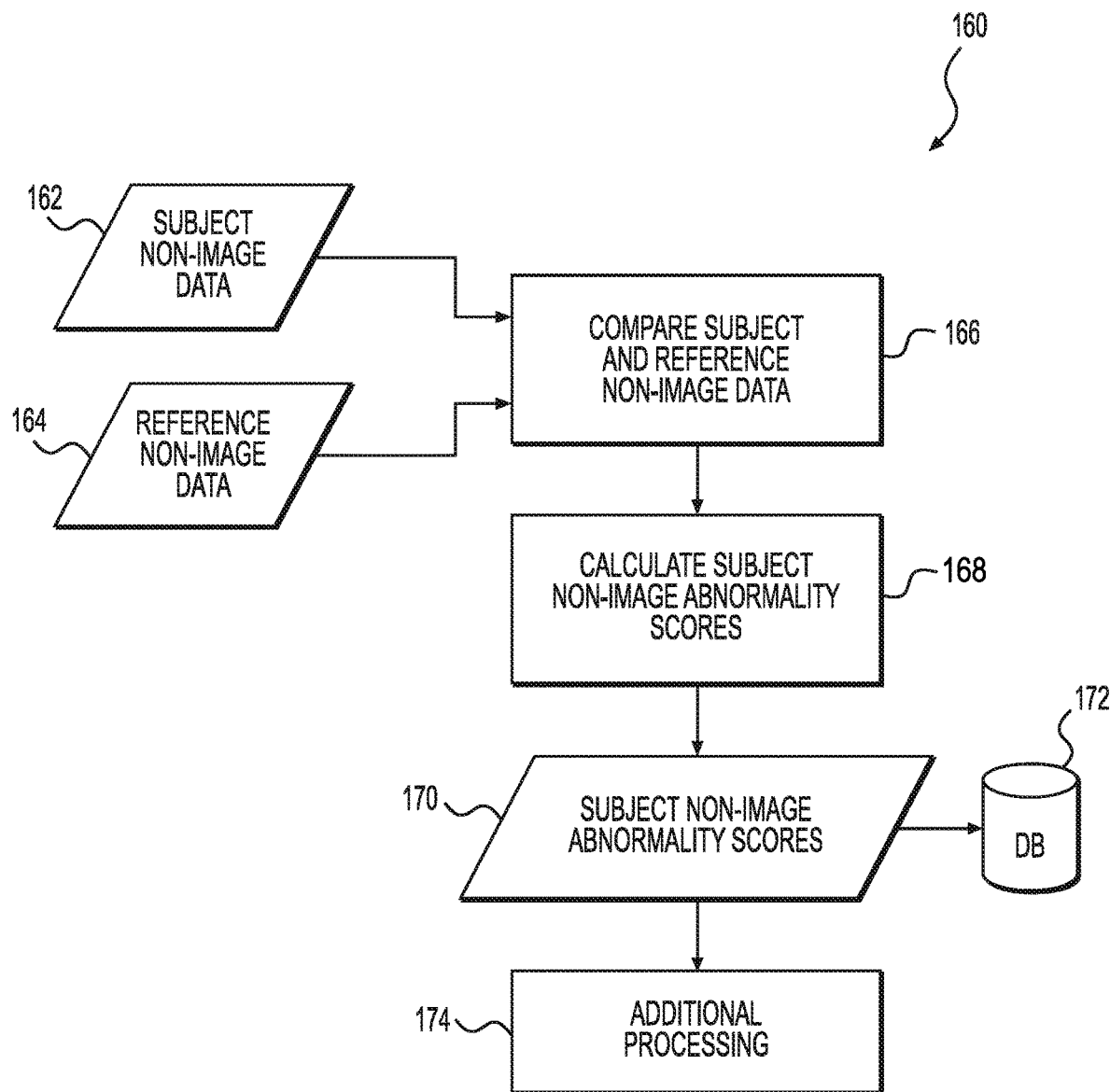
FIG. 8 is a flow chart of an exemplary method for generating non-image abnormality scores for a subject.

The extent of subject deviation from reference data may also be translated into one or more abnormality scores, which may be generated through the methods shown in FIGS. 7 and 8. An exemplary method 140 of FIG. 7 may include accessing subject image data 142 and reference image data 144, including standard image data and image data representative of a particular gastric condition and/or severity level thereof. Such image data may be received from any suitable source, such as a database or an imaging system, such as an endoscope. The image data 142 and 144 may include image data collected from a wide range of sources. The reference image data 144 may be standardized according to any desired characteristics. For instance, the reference image data 144 may include data representative of features of normal individuals with certain characteristics, for example, characteristics similar to the subject. In step 146, the subject image data 142 and the reference image data 144 may be compared to determine deviations of the subject image data 142 from the reference image data 144. Such differences may generally represent deviation, for example, structural differences between the subject and normal (e.g., healthy) subjects.

The method 140 may also include calculating 148 one or more subject image abnormality scores for differences between the subject image data 142 and the reference image data 144. Such abnormality scores may be indicative of an array of structural deviations of the subject relevant to the reference image data. The subject image abnormality scores may be calculated in various manners, such as based on projection deviation, single pixel (2D) deviation, single voxel (3D) deviation, or on any other suitable technique. The calculated subject image abnormality scores 150 may then be stored in a database 152, output to a user, or may undergo additional processing in one or more further steps 154.

FIG. 8 shows an exemplary method 160 for calculating non-image abnormality scores. The method 160 may include accessing subject non-image data 162 and reference non-image data 164. The non-image data may be received from any suitable source, such as a database, a computer, or subject monitor. The subject non-image data 162 may include any non-image information collected for the purpose of diagnosing the subject, such as clinical data, laboratory data, subject history, family history, subject vital signs, and the like, and may also include results of other tests, such as genetic tests and so forth. The reference non-image data 164 may include similar data, which may be standardized based on one or more characteristics of the persons from whom it was obtained. The subject non-image data 162 and reference non-image data 164 may include one or both of numeric data and enumerated data, each of which may be continuous or discrete. The reference non-image data 164 may include data representative of features of normal persons with particular characteristics, such as those similar to the subject. In step 166, the subject non-image data 162 may be compared to the reference non-image data 164 to identify differences between the data. Such differences may generally represent a deviation, such a structural deviation, of the subject from normal (e.g., healthy) individuals.

Additionally, the method 160 may include a step 168 of calculating one or more subject non-image abnormality scores for differences between the subject non-image data 162 and the reference non-image data 164. Various techniques may be used to calculate the subject non-image abnormality scores, including, for example, z-score deviation or distribution analysis. Of course, it will be appreciated that other calculation techniques may also or instead be employed in other embodiments. The calculated subject non-image abnormality scores 170 may be stored in a database 172, output to a user, or may undergo additional processing in one or more further steps 174.

Figure 9:
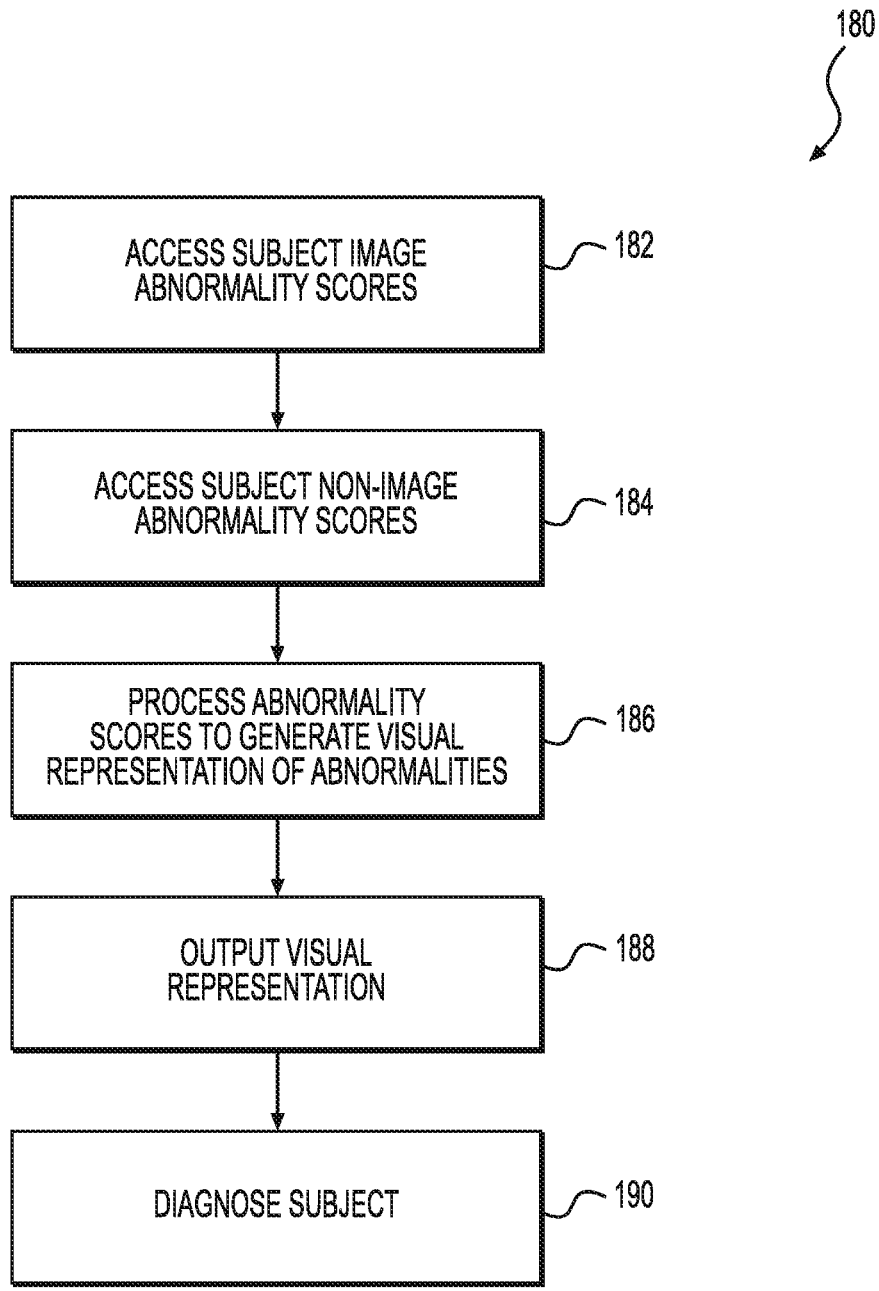
FIG. 9 is a flow chart of an exemplary method for generating a visual representation of subject abnormality data based on abnormality scores.

Subject abnormality scores may be used to generate one or more visual representations to facilitate subject diagnosis. An exemplary method 180 is illustrated in FIG. 9, which includes accessing one or more subject image abnormality scores and one or more subject non-image abnormality scores in steps 182 and 184, respectively. These abnormality scores may be processed 186 to generate a visual representation of the differences represented by the subject abnormality scores. Subject abnormality scores may be derived from dynamic data (e.g., video) or longitudinal data (e.g., data acquired at discrete points in time over a given period), and multiple visual representations corresponding to deviations at different points of time may be generated in step 186. The one or more visual representation may then be output 288 to facilitate diagnosis of the subject in step 190. For abnormalities derived from dynamic or longitudinal data, multiple visual representations may be output simultaneously or sequentially.

Technical effects of the present disclosure include the accurate and consistent diagnoses of various gastric conditions and severity levels thereof, as well as providing decision support tools for user-diagnosis of subjects. For example, by using abnormality (e.g., difference) images, it may be easier to identify areas of abnormalities or deviations from normal, as well as to determine the extent of deviation in a subject. For example, the difference images allow a user to focus on, extract, and enhance the deviations and abnormalities in the subject image that may not be as apparent from a comparison of the raw subject images with the standard images. Technical effects may also include the visualization of subject image and non-image information together in a holistic, intuitive, and uniform manner, facilitating accurate and objective diagnosis by a user. Additionally, the present systems, methods, and computer-readable media enable the generation of subject abnormality images and reference abnormality images of known gastric conditions and/or severity levels thereof, and the combination of such images with non-image data, to facilitate quantitative assessment and diagnosis of gastric conditions and their severity level. The disclosed systems, methods, and computer-readable media enable analysis of multiple parameters, including both image and non-image data, to accurately and objectively diagnose severity levels of gastric conditions.

A system may be programmed or otherwise configured to gather clinical information and create integrated comprehensive views of the progression of statistical deviations of data of an individual subject from one or more normal subject populations over time from longitudinal data. In other words, subject image and/or non-image data at a particular point in time may be compared to subject image and/or non-image data collected at an earlier point in time to determine a change in the data of the subject over time. The change in the subject data over time may be used to facilitate diagnosis, for example, diagnosis of gastric atrophy, gastritis, or gastric cancer and/or a severity thereof. In addition, the present systems, methods, and computer-readable media provide structured integrated comprehensive views of the deviation of the clinical information across a given diseased subject population when compared against a population of normal individuals, both at a single point in time and across multiple time points (longitudinally). Such comprehensive views described herein may display a normative comparison to thousands of standardized and normalized data values concurrently. The resulting comprehensive view can provide patterns of deviations from normal that may indicate a characteristic pattern corresponding to known gastric conditions or abnormalities and severity levels thereof.

Using the presently disclosed techniques, a user may be able to easily compare the results of one parameter with another, and draw conclusions therefrom. To facilitate such analysis, the various parameters may be standardized and normalized. Further, an integrated comprehensive view of clinical data of a specific population of people with respect to a population of normal subjects is provided. The view may include disparate types of clinical data, including both image and non-image data in a manner that makes it easy for humans to distinguish the distribution of clinical parameter results across gastric condition populations. Although various graphs can be used to analyze results for a single clinical parameter across populations, they are quite cumbersome and impractical when it comes to visualizing and analyzing a larger number of parameters. The present disclosure analyzes multiple parameters, including both image and non-image data to accurately and objectively diagnose severity levels of gastric conditions.

Stained Images to Facilitate Diagnosis of Severity of Gastric Atrophy

In an exemplary embodiment, a diagnostic system, method, and computer-readable storage medium for determining or facilitating diagnosis of a severity of gastric atrophy in a subject is provided. Prolonged inflammation causes normal stomach tissue to deform such that the surface, foveolar, and glandular epithelium in the oxyntic or antral mucosa is replaced by intestinal epithelium. This is a condition known as intestinal metaplasia. Intestinal metaplasia results in the thinning of the stomach mucosa, which is known as atrophic gastritis or gastric atrophy. Progressive atrophy is believed to increase a subject's risk of developing gastric cancer. Staining the interior of the stomach makes it possible to distinguish between a normal (e.g., healthy) stomach and a stomach that has developed intestinal metaplasia.

In the present embodiment, the interior of the stomach of the subject is stained with a dye to obtain subject stained images, and the subject stained images are compared with reference images to determine the severity of gastric atrophy. Dye may be applied to the subject's stomach by any suitable method for staining a stomach. For example, the dye may be sprayed onto the stomach using an endoscope or the subject may ingest the dye before endoscopic images are taken. The dye may include any suitable dye for staining the stomach, such as methylene blue, Evans blue, cardio blue, or brilliant blue. For example, methylene blue, Evans blue, or cardio blue may be sprayed onto the stomach by an endoscope to stain the subject's stomach blue. The subject may drink brilliant blue to stain the subject's stomach before collecting images. Then, an endoscope is inserted into the subject's stomach and stained images are acquired. The subject stained images may be stored on a server or in a database, for example, in the storage device 14, such as memory or other storage devices (FIG. 1).

Reference stained images (e.g., of stomachs of individuals with different severity levels of gastric atrophy) and standard stained images (e.g., of healthy stomachs) may be obtained in the same manner discussed above. For example, reference data, including stained image data and non-image data, may be collected from people or groups of people. Such people may include healthy people that are not suffering from gastric atrophy, and other people suffering from different severity levels of gastric atrophy. The reference stained image and non-image data may be standardized and categorized according to one or more characteristics. For example, such reference data may be categorized based on population characteristics, such as race, gender, or age of the people from which the data was collected. Standardized data permits average stomach characteristics to be calculated for healthy subjects and subjects with different severity levels of gastric atrophy.

The standard stained image may be an earlier stained image of the subject in a healthy state or may be a stained image of a stomach of a different person in a healthy state. As discussed in more detail below, the different person may be selected based on one or more shared characteristics with the subject, such as age, race, and sex.

An abnormality stained image of the subject's stomach may be generated through any suitable technique. For example, an abnormality image may be generated by comparing the subject stained image with a standard stained image as discussed above. For example, a difference image between the subject stained image and the standard stained image of a healthy stomach may be obtained as a subject abnormality image. Prior to comparing the subject stained image and the standard stained image, the subject stained image and standard image may undergo preprocessing to extract or enhance certain areas or anatomical features, such as areas of thinning mucosa, according to any known methods. The images may also be standardized to facilitate comparison and analysis.

The abnormality image may be a representative image in which each point of the image represents a score generally corresponding to a number of standard deviations (based on a selected population) in the difference between a subject value (e.g., staining intensity) and the average value (e.g., staining intensity) of the population for that point. Abnormality images may be generated from image data and/or one or more of numerical data, text data, waveform data, image data, video data, and the like.

The image(s) may be visualized to facilitate further analysis or diagnosis. For instance, any or all of the standard stained images, subject stained image, subject abnormality images, and reference stained images (discussed below) may be expressed as surface matrices, and can be displayed or overlaid on a three-dimensional (3D) stomach surface.

Figure 10:
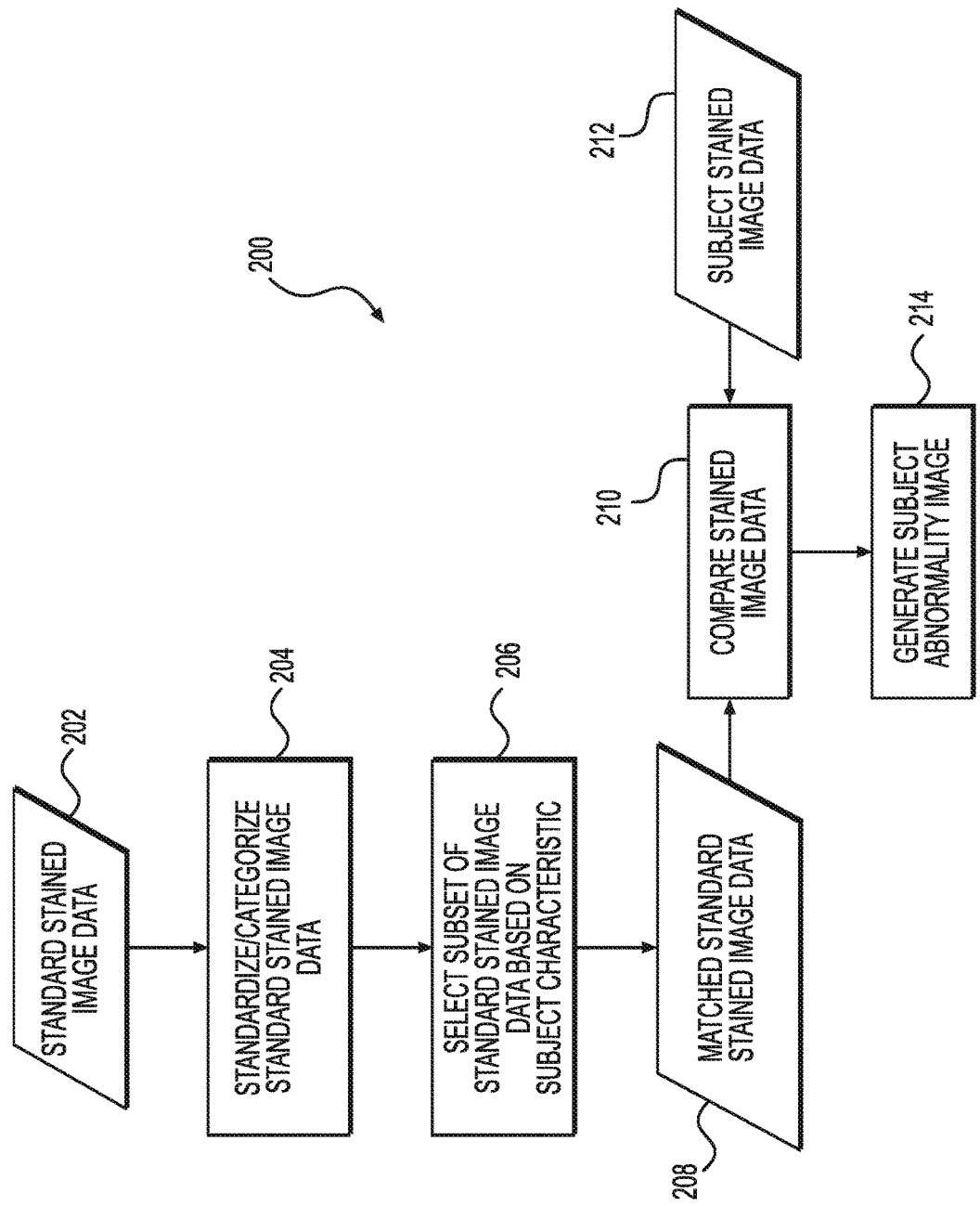
FIG. 10 is a flow chart of an exemplary method for generating subject abnormality images to facilitate diagnosis of a severity level of gastric atrophy.

An exemplary method 200 for generating abnormality images, indicative of differences between a region of the subject stained stomach image and a region of a standard stained stomach image, is illustrated in FIG. 10. Standard stained image data is obtained in step 202, and is categorized and standardized in step 204. Standard stained image data and non-image data may be collected from people and categorized or standardized according to one or more desired characteristics, such as age, gender, or race. While the presently illustrated embodiment is described with respect to stained image data, it is noted that reference non-image data and subject non-image data may also, or instead, be used to generate the abnormality images discussed herein.

The method 200 may include selecting a subset of the standard stained image data based on a subject characteristic, such as age, race, or gender in step 206, as discussed above with respect to FIG. 3 (e.g., step 54). For example, if the subject is an eighty-five year old Japanese woman, a subset of the standard image data grouped to include standard stained images pertaining to women or Japanese women between eighty and ninety years of age may be selected comparative purposes as this data may be more relevant than a group of standard stained images collected from other groups of individuals, such as men, or non-Japanese women, or younger individuals, such as individuals younger than eighty, seventy, or sixty.

Once a desired group of standard stained image data is selected, the matched standard stained image data 208 may be compared to stained image data 212 of the subject in step 210. Non-image data of the subject may instead or also be compared to matched standard non-image data, as described above. Additionally, the various data may be processed and categorized in any suitable manner to facilitate such comparisons. In step 214, a subject abnormality image may be generated based at least in part on the comparison 210 between the matched standard stained image data 208 and the subject stained image data 212.

Figure 11B:
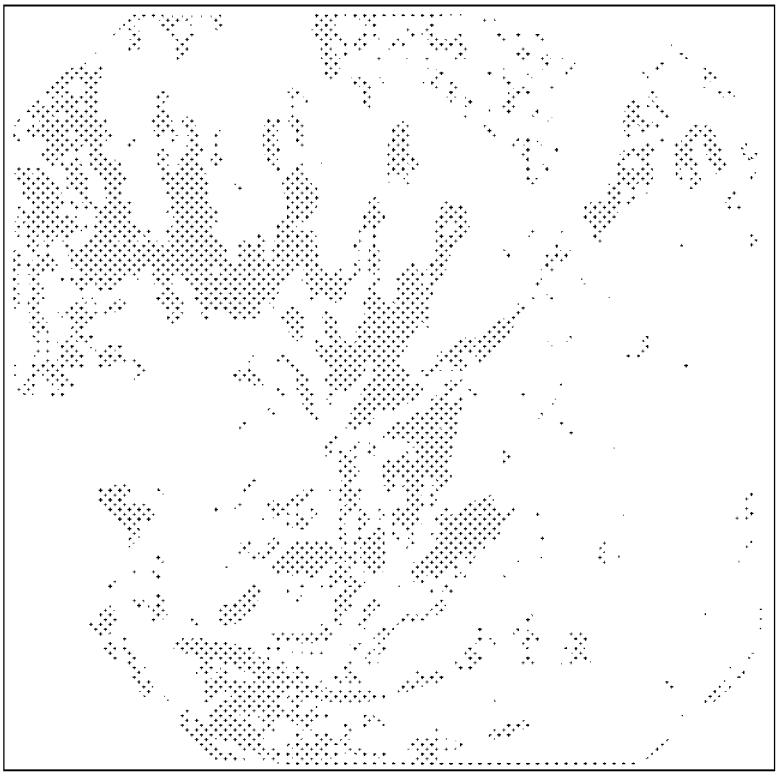
FIGS. 11A-D are exemplary abnormality images of stained stomachs.
Figure 11A:
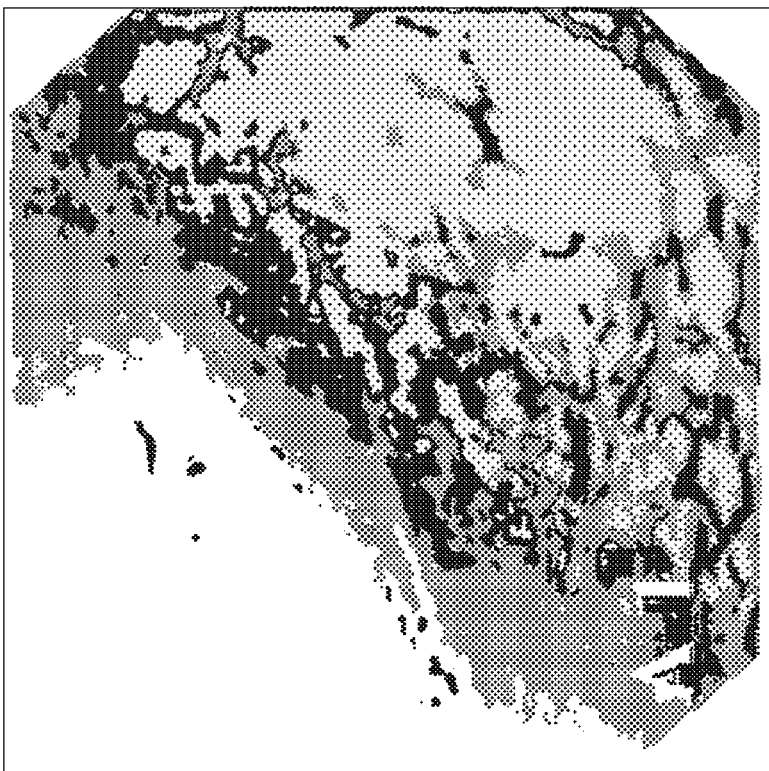
Figure 11D:
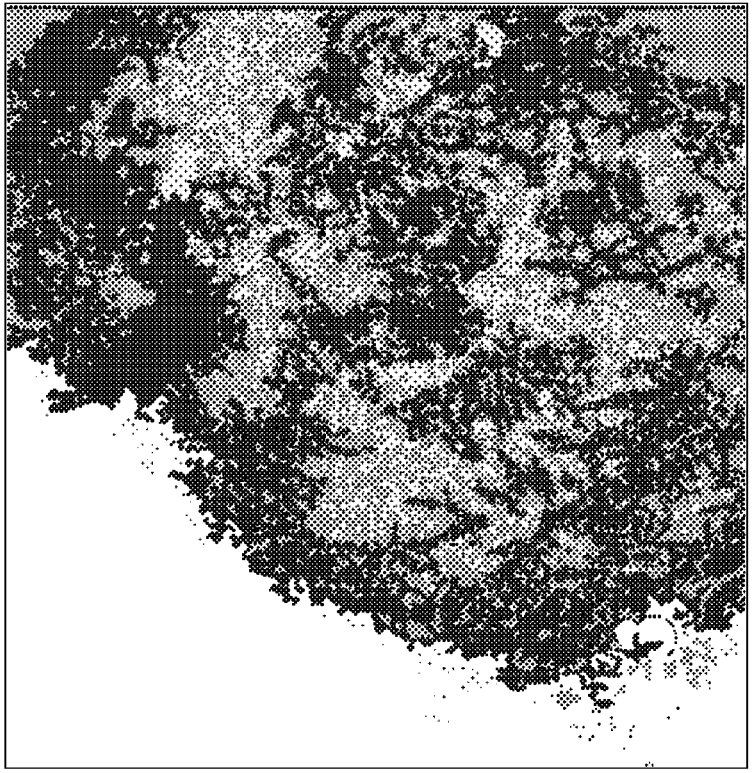
Figure 11C:
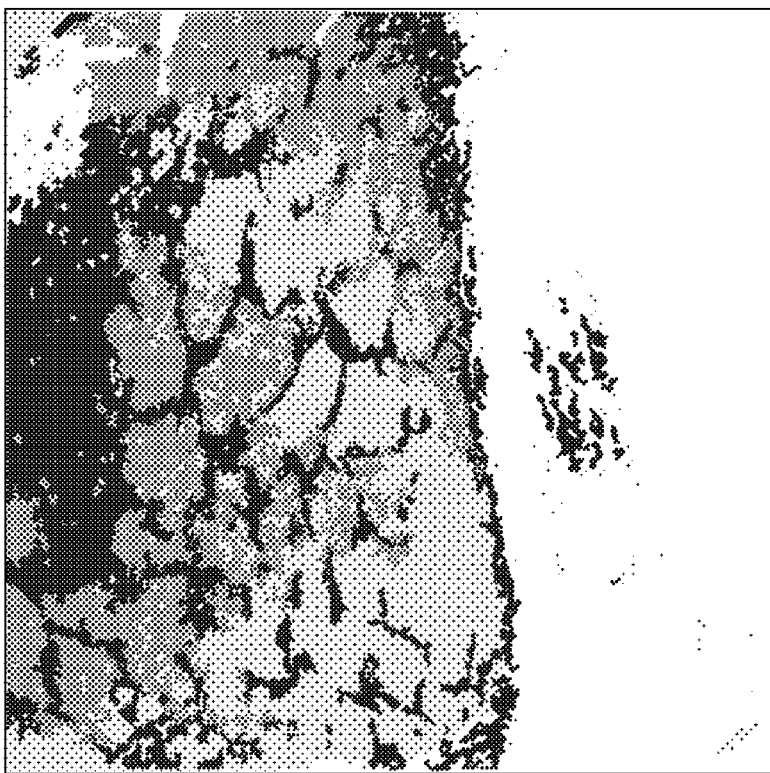

Exemplary subject abnormality images are shown in FIGS. 11A-D. FIG. 11A shows a healthy stomach with no signs of gastric atrophy. FIG. 11B shows an abnormality image of a stomach with low severity gastric atrophy. FIG. 11C shows an abnormality image of a stomach with moderate severity gastric atrophy. FIG. 11D shows an abnormality image of a stomach with high severity gastric atrophy. As shown in FIGS. 11A-11D, various regions of the stomachs may be color coded according to a scale to represent degree of atrophy, or deviation from normal mucosal thickness, to facilitate a user's understanding of the represented anatomical information.

For example, the healthy stomach shown in FIG. 11A has almost no staining, indicating that the mucosal thickness throughout the stomach is within healthy ranges and there are no signs of gastric atrophy. In FIG. 11B, the stomach abnormality image has minimal stained areas with a low staining intensity (e.g., lightly stained), indicating that the mucosal thickness is slightly below healthy ranges in the lightly stained areas of the stomach, which corresponds to low severity gastric atrophy. In FIG. 11C, the stomach abnormality image has larger stained areas than FIG. 11B, including areas with a higher staining intensity (e.g., medium staining intensity), indicating that the mucosal thickness is slightly to moderately below healthy ranges in the stained areas (ranging from light to medium staining intensity), which corresponds to moderate severity gastric atrophy. Lastly, FIG. 11D shows a stomach abnormality image that is almost entirely stained, including several areas with a medium to high staining intensity, indicating that the mucosal thickness is moderately to significantly below healthy ranges in the stained areas (ranging from medium to high staining intensity), which corresponds to high severity gastric atrophy.

Figure 12:
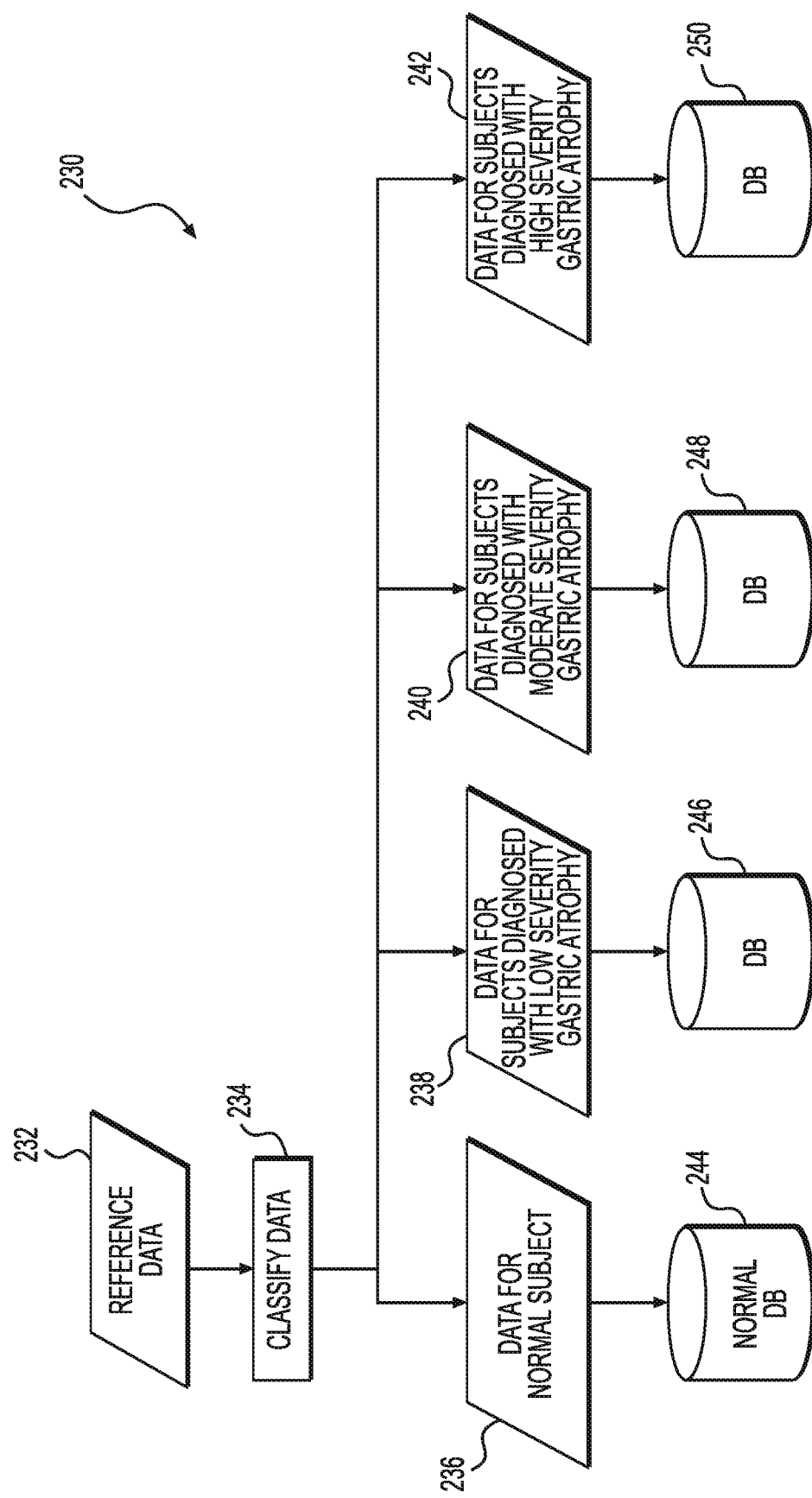
FIG. 12 is a flow chart of an exemplary method for categorizing reference and standard data to facilitate diagnosis of a severity level of gastric atrophy.

Additionally, reference stained image data may be categorized and sorted into standardized databases, such as through an exemplary method 230 shown in FIG. 12. The method may include acquiring reference data 232, which may include stained image and non-image data from various people, and categorizing the data in step 234. For example, the reference data 232 may be categorized into various groups, such as normal (healthy) subject data 236, data 238 of subjects clinically diagnosed with low severity gastric atrophy, data 240 of subjects diagnosed with moderate severity gastric atrophy, and data 242 of subjects diagnosed with high severity gastric atrophy. The data 236, 238, 240, and 242 may be stored in respective databases 244, 246, 248, and 250. Such databases may be stored on a server, in one or more memory or storage devices, and/or in other suitable media. Such databases may be continuously or periodically updated as more subjects are diagnosed. As discussed above, the data 236, 238, 240, and 242 in each database 244, 246, 248, and 250 may be further standardized and classified according to various subject characteristics, such as age, gender, and race.

Figure 13A:
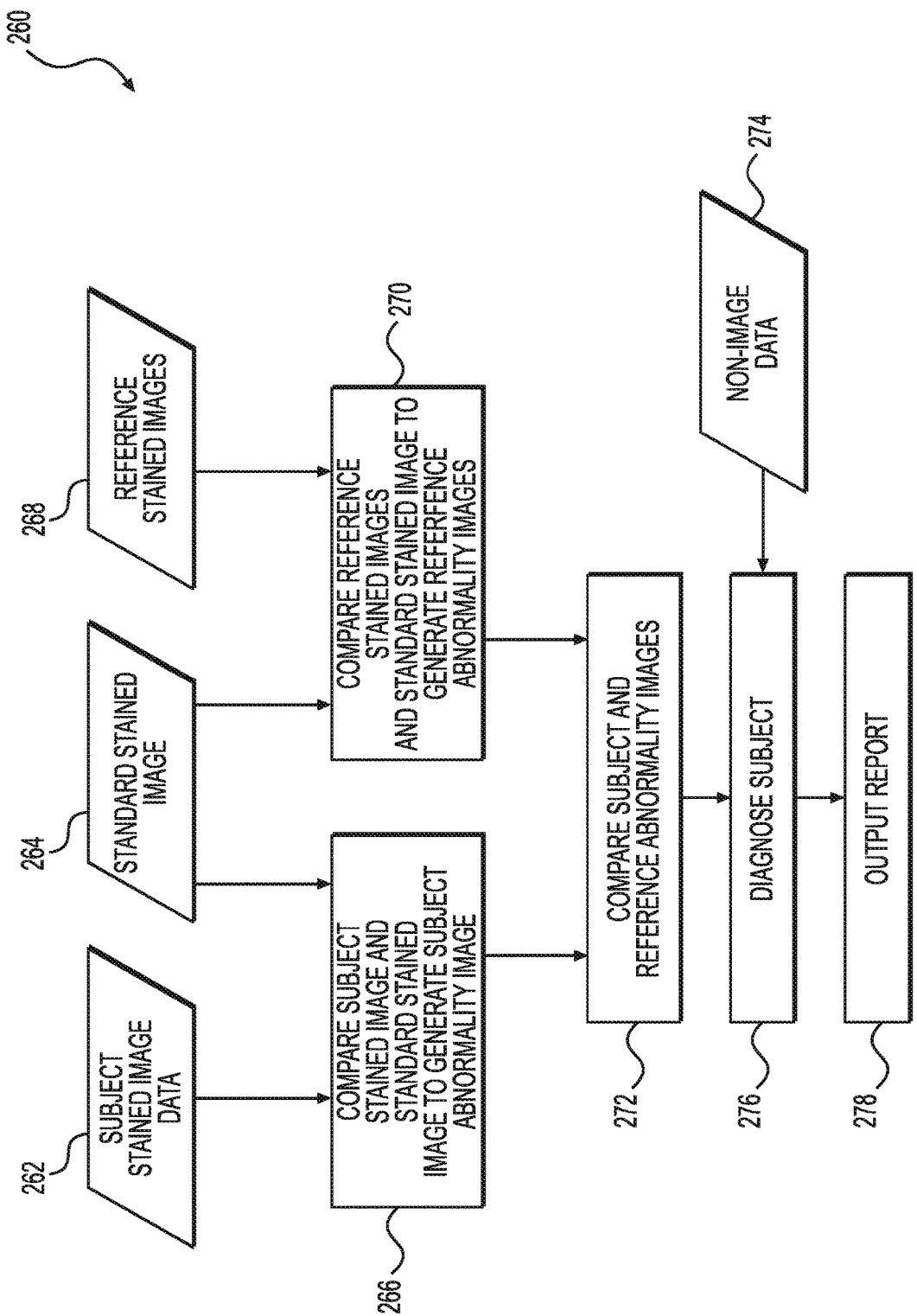
FIGS. 13A-D are flow charts of exemplary methods for diagnosing a severity level of gastric atrophy via stained images.
Figure 13B:
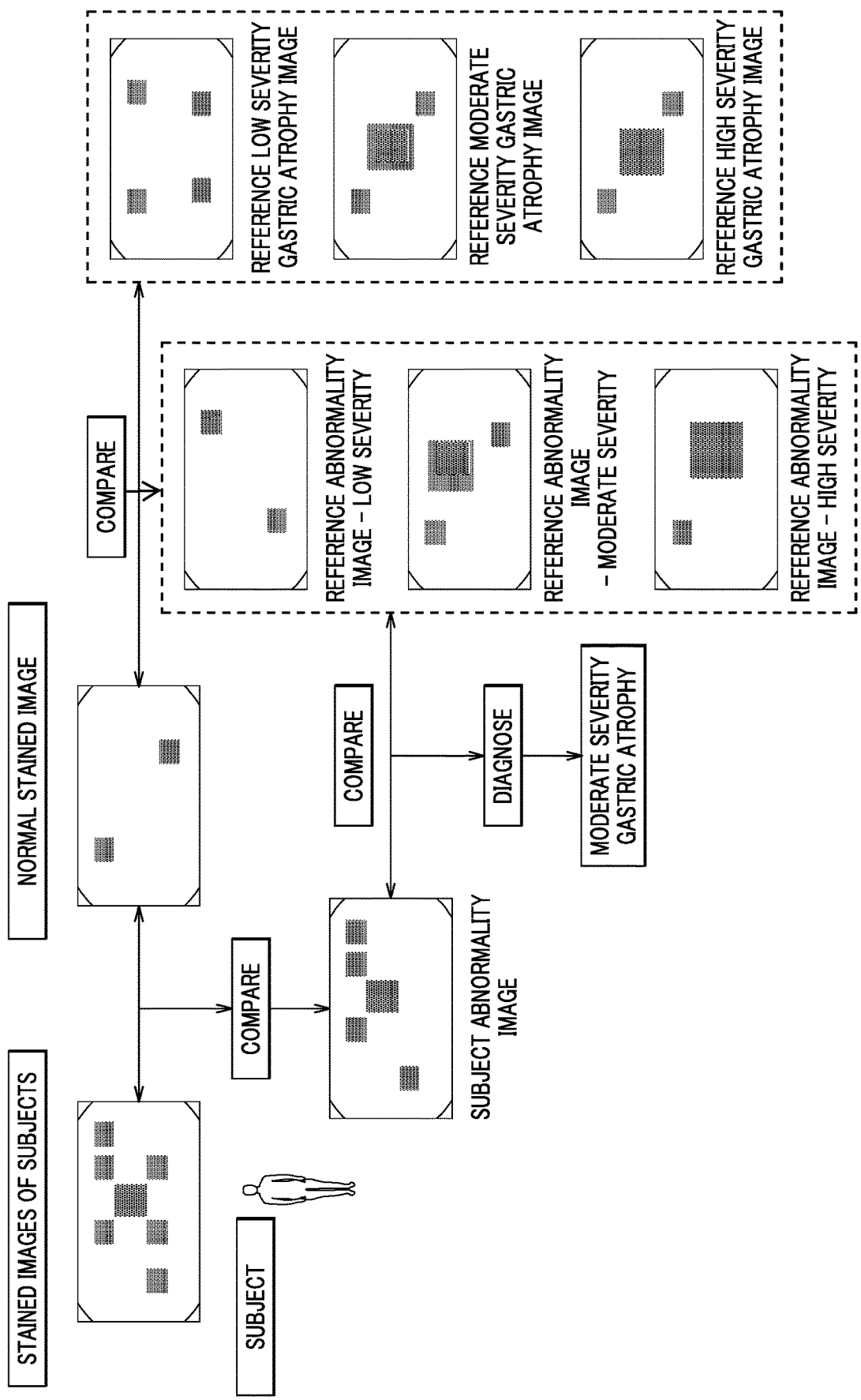

Exemplary methods for diagnosing a subject with a particular severity of gastric atrophy based at least in part of the foregoing data is shown in FIGS. 13A-B. The method 260 may include obtaining stained image(s) of the stomach of the subject 262, and comparing the subject stained image(s) 262 with standard stained image(s) 264 of healthy stomachs to generate a subject abnormality image 266, which is indicative of differences between the subject stained image(s) and the standard stained image(s).

Further with respect to FIG. 13A, reference stained images 268 of stomachs exhibiting different severity levels of gastric atrophy are also compared 270 to the standard stained image(s) 264 to generate reference abnormality images, which are indicative of differences between the reference stained images 268 and the standard stained image(s) 264. Reference stained images 268 may be standardized images acquired from a database of reference stained images 268 for each severity level of gastric atrophy collected from a particular group of people diagnosed with a particular severity level of gastric atrophy, as discussed above. The reference stained images 268 may be the actual stained images, optionally processed to enhance or extract the structural feature of interest, collected from the people of a particular group or characteristic category. Alternatively, the reference stained images 268 may be average images created based on the data collected from the people of a particular population diagnosed with a particular severity level of gastric atrophy. For example, a representative average stained stomach image for each severity level of gastric atrophy may be generated. Thus, multiple representative or average stained images may be created for each severity level of gastric atrophy.

The subject abnormality image 266 is then compared 272 with the reference abnormality images 270. All of the images may be standardized into one or more common or similar formats to facilitate analysis and comparison. The subject is diagnosed 276 as having a particular severity level of gastric atrophy based at least on part on the comparison between the subject abnormality image the reference abnormality images. The diagnosis 276 may also be made by taking other data 274 and analysis into consideration, including non-image data, such as clinical data, laboratory data, subject history, family history, subject vital signs, results of various tests (e.g., genetic tests), and any other relevant non-image data. Based on the subject and reference data, numerous reference and subject abnormality data and images may be created. Then, a report 278 of the diagnosis 276 is output, for example, to an output device 18 (shown in FIG. 1), such as a display or a printer, or to a database for storage, or to a user in a human-readable format.

The various images and data described herein may be stored in one or more databases to facilitate subsequent data analysis. Moreover, any or all of the foregoing comparisons may be performed either automatically by a data processing system, such as system 10, or by a medical professional, such as a doctor, or by some combination thereof, to facilitate automatic or manual diagnosis of the subject in step 276.

FIG. 13B shows an exemplary process in which a subject is diagnosed with moderate severity gastric atrophy based on a comparison of subject stained images with reference images. One or more stained images of the subject are compared with one or more normal stained images to generate a subject abnormality image. For instance, in FIG. 13B, the normal stained image is subtracted from the subject stained image to generate a difference image (subject abnormality image). As shown in FIG. 13B, the subject abnormality image shows the staining differences between the subject stained image and the normal stained image and eliminates shared staining between the images. The staining differences shown in the subject abnormality image are indicative of abnormalities or deviations from normal.

Reference abnormality images (representative of various severity levels of gastric atrophy) are compared to the normal stained image in the same manner to generate reference abnormality images (representative of various severity levels of gastric atrophy). For example, in FIG. 13B, the normal image is subtracted from each reference image to generate a corresponding reference difference (abnormality) image. Then the subject abnormality image is compared to the reference abnormality images to make a diagnosis. Not only the area of staining (e.g., size), but also the staining intensities of the stained area in the abnormality images is compared. In FIG. 13B, the subject abnormality image most closely resembles the reference abnormality image representative of moderate severity gastric atrophy. Therefore, based at least in part on this comparison, the subject is diagnosed with moderate severity gastric atrophy in the example shown in FIG. 13B.

The generation of the subject and reference abnormality (e.g., difference) images enables the abnormalities and deviations in the subject stained image to be visualized, thereby facilitating accurate and consistent diagnoses to be made. Such differences cannot be as easily detected by simply viewing and comparing the subject and reference images. Additionally, as discussed in more detail below, the images can be analyzed for, for example, staining intensity to further ensure objective and consistent diagnoses are made.

Figure 13C:
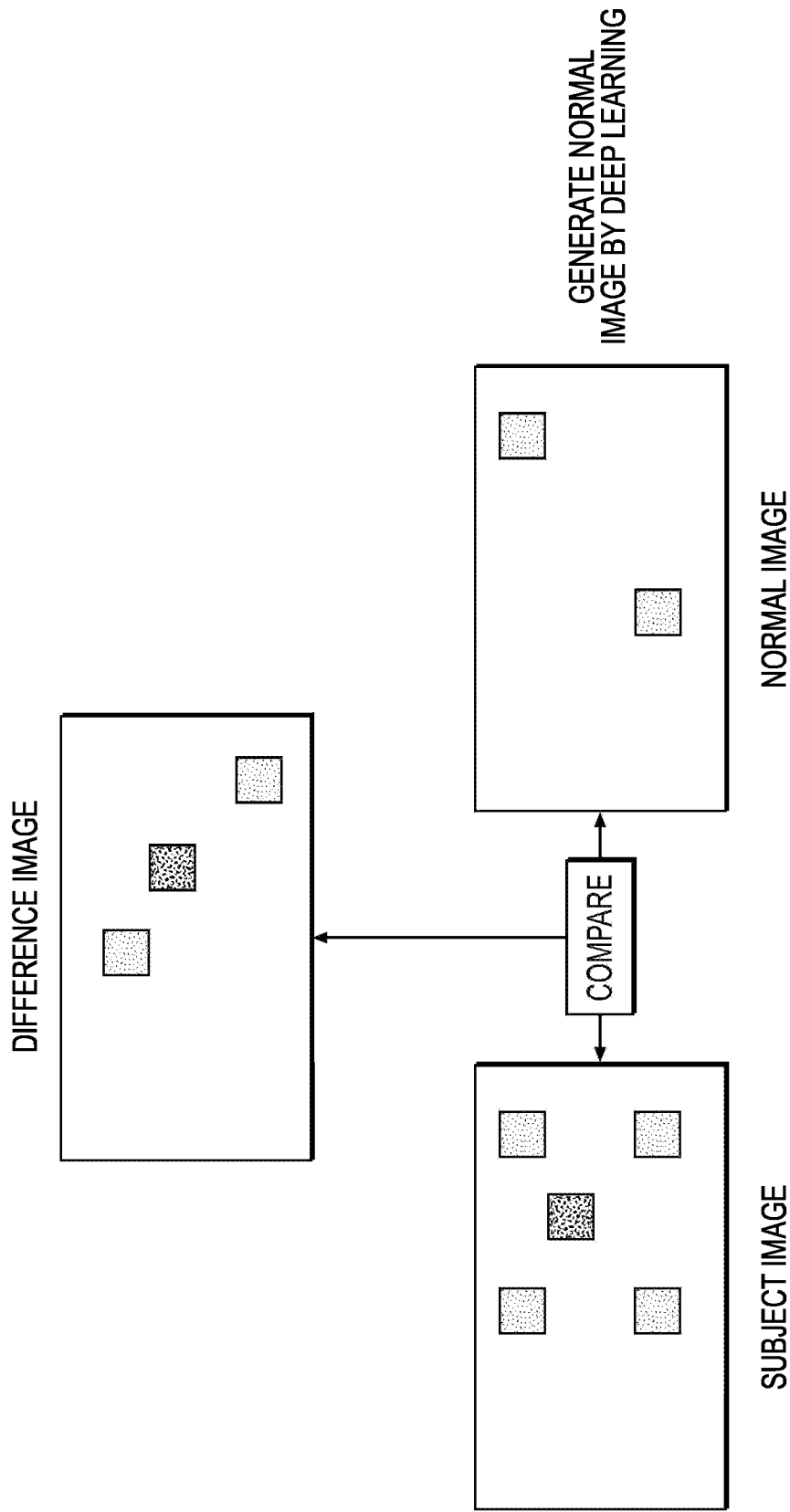
Figure 13D:
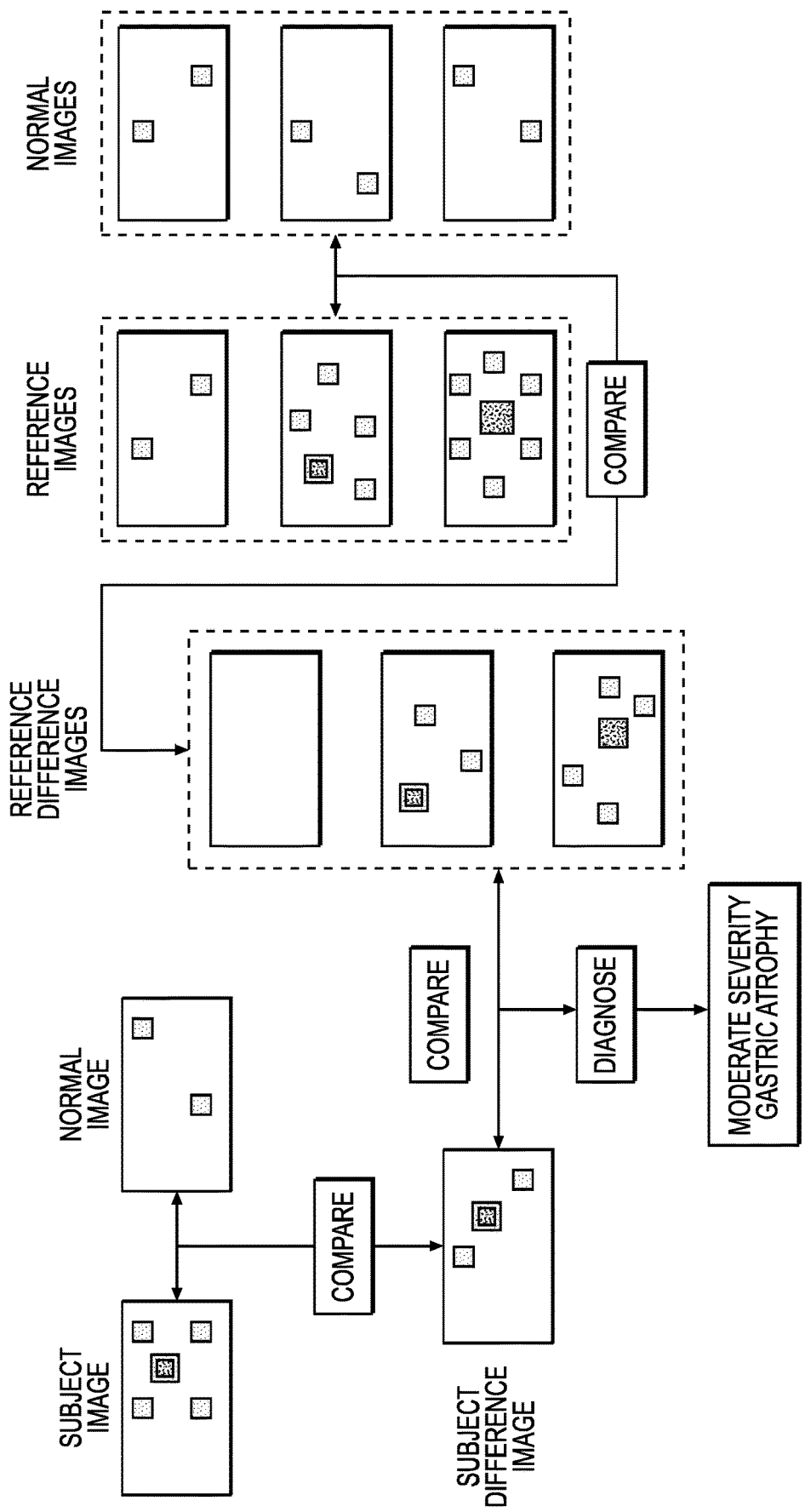

FIG. 13C shows an example where the subject difference image is generated from a subject stained image and a normal stained image generated by deep learning. Similarly, as shown in FIG. 13D, reference difference images may be generated from reference stained images representative of various severity levels of gastric atrophy and normal images generated by deep learning. That is, instead of comparing the subject and reference stained images with the same normal (e.g., standard) image, the present systems and methods employ deep learning techniques to generate normal images for use in generating the reference and subject differences images.

For example, as discussed above, a deep learning model, such as a VAE, may be trained to generate corresponding normal images. Such training may be unsupervised learning in which only normal stained images are input into the model for training. Such normal training images may be stained images of healthy stomachs that are substantially free of abnormalities. The model may be trained via an iterative process involving compressing and reconstructing input normal stained images by an encoder and a decoder to extract and learn features and patterns of normal stained images without external identification.

Once learned, the model can be given a stained image of a stomach to predict whether it is normal or abnormal. Because the trained model has been trained using only normal stained images, it can detect features different from normal stained images as abnormal features. Additionally, when given an abnormal stained image, such as a reference image indicative of a particular severity level or an abnormal subject image, the trained model can generate a corresponding normal stained image by compressing the abnormal image and restoring the compressed image as a normal stained image in which the abnormal features are omitted. That is, the trained model generates a normal stained image from the abnormal image. The abnormal feature(s) in the original image are restored as normal feature(s) in the restored stained image (generated normal stained image).

Therefore, as illustrated in FIGS. 13C and 13D, a normal stained image may be generated from a subject stained image and normal stained images may be generated from reference stained images for each severity level by deep learning. In other words, deep learning may be used to generate normal stained images that correspond to reference stained images for each severity level or correspond to the subject stained image except that abnormal part(s) have been removed. Then, the subject and reference difference images may be obtained by pattern matching. By using deep learning, a pseudo-normal stained image can be accurately generated, and an accurate difference image can be generated. Additionally, it is sufficient to train the deep learning device or network using only normal training images, and it is not necessary to train with abnormal images. Therefore, the amount of data necessary for training the deep learning device or network can be reduced. Collecting a large amount of abnormal data (e.g., abnormal images) is difficult. Thus, reducing the burden of collecting a large amount of data is a significant advantage.

Figure 14:
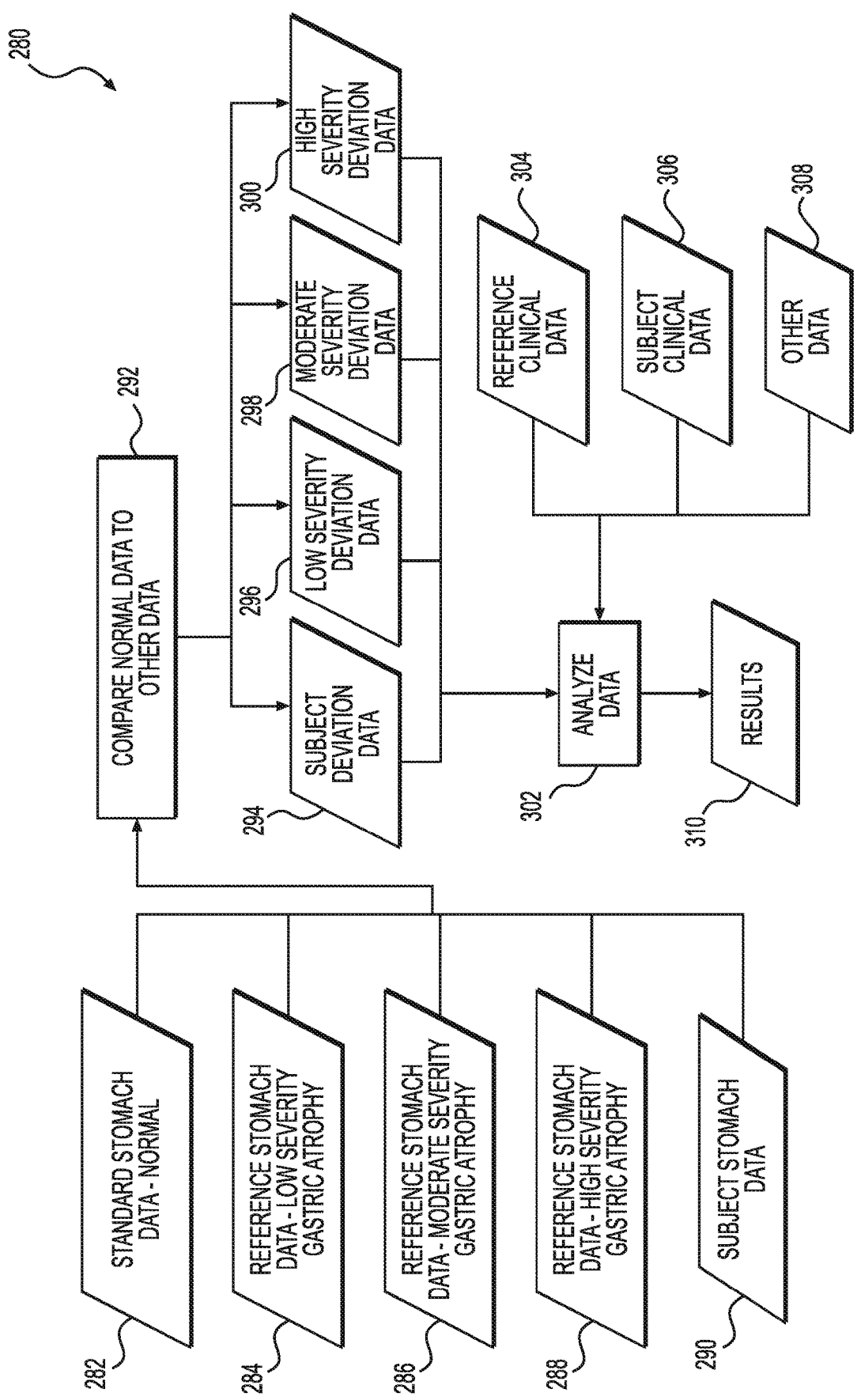
FIG. 14 is a flow chart of an exemplary method for generating and analyzing abnormality data to facilitate diagnosis of a severity level of gastric atrophy.

Based on the subject and reference stained image and non-image data discussed above, numerous reference and subject abnormality data and images may be created. By way of example, an exemplary method 280 for generating and analyzing such abnormality data is shown in FIG. 14. The method 280 includes acquiring reference stomach data, including reference stained images, for: normal subjects without gastric atrophy (data 282) (e.g., standard data, including standard stained image(s)), subjects clinically diagnosed with low severity gastric atrophy (data 284), subjects diagnosed with moderate severity gastric atrophy (data 286), and subjects diagnosed with high severity gastric atrophy (data 288). The method 280 may also include acquiring subject stomach data 290, including subject stained images.

In step 292, the standard data 282 may be compared to each of the other data 284, 286, 288, and 290, to generate low severity gastric atrophy abnormality data 296, moderate severity gastric atrophy abnormality data 298, high severity gastric atrophy abnormality data 300, and subject abnormality data 294, all of which may represent deviations from the standard/normal data 282. Such abnormality data may include structural abnormality images representative of differences between the subject data 290 and: (i) the reference data 284, 286, and 288 for the particular severity level of gastric atrophy, and/or (ii) the standard data 282. Structural abnormality images may deviations in mucosal thickness from normal, healthy ranges for a particular population. For example, the thinner the mucosa, the more severe the atrophy. As discussed above, increased areas of thinner mucosa may be indicative of more severe gastric atrophy, whereas a few or some areas of slightly to moderately thinner mucosa may be indicative of low or moderate severity gastric atrophy.

In step 302, such abnormality data may be analyzed. For example, a subject abnormality image or data may be compared to representative reference abnormality images to facilitate diagnosis of the subject with respect to a particular severity level of gastric atrophy. Additionally, reference clinical data 304, subject clinical data 306, and other data 308 may also be analyzed by a data processing system or a user to facilitate diagnosis. Such analysis may include pattern matching of subject images and reference images, and confidence levels of such matching may be provided to a user. Finally, results 310 of the analysis may be output to storage or to a user via, for example, an output device 18, such as a display or printer.

The extent of subject deviation from standard data may also be translated into one or more abnormality scores, which may be generated through the methods shown in FIGS. 7 and 8, discussed above. For example, with reference to FIG. 7, the method 140 may be include accessing subject image data 142 (e.g., stained image data) and reference image data 144 (e.g., stained image data), including standard stained image data and stained image data representative of a particular severity level of gastric atrophy. Such stained image data may be received from any suitable source, such as a database or an imaging system, such as an endoscope. The stained image data 142 and 144 may include stained image data collected from a wide range of sources. The reference stained image data 144 may be standardized according to any desired characteristics. For instance, the reference stained image data 144 may be standard stained image data generally representative of features of normal (e.g., healthy) individuals with certain characteristics, for example, characteristics similar to the subject. In step 146, the subject stained image data 142 and the reference stained image data 144 may be compared to determine deviations of the subject stained image data 142 from the reference stained image data 144. Such differences may generally represent deviation, for example, structural differences between the subject and normal (e.g., healthy) subjects.

The method 140 may also include calculating 148 one or more subject stained image abnormality scores for differences between the subject stained image data 142 and the reference stained image data 144. Such abnormality scores may be indicative of an array of structural deviations of the subject relevant to the reference stained image data. The subject stained image abnormality scores may be calculated in various manners according to any suitable technique. The calculated subject stained image abnormality scores 150 may then be stored in a database 152, output to a user, or may undergo additional processing in one or more further steps 154. The method 160 of FIG. 8 of calculating a subject non-image abnormality score, which is discussed in more detail above, may also be calculated for diagnosing or facilitating diagnosis of a particular severity level of gastric atrophy.

Figure 15:
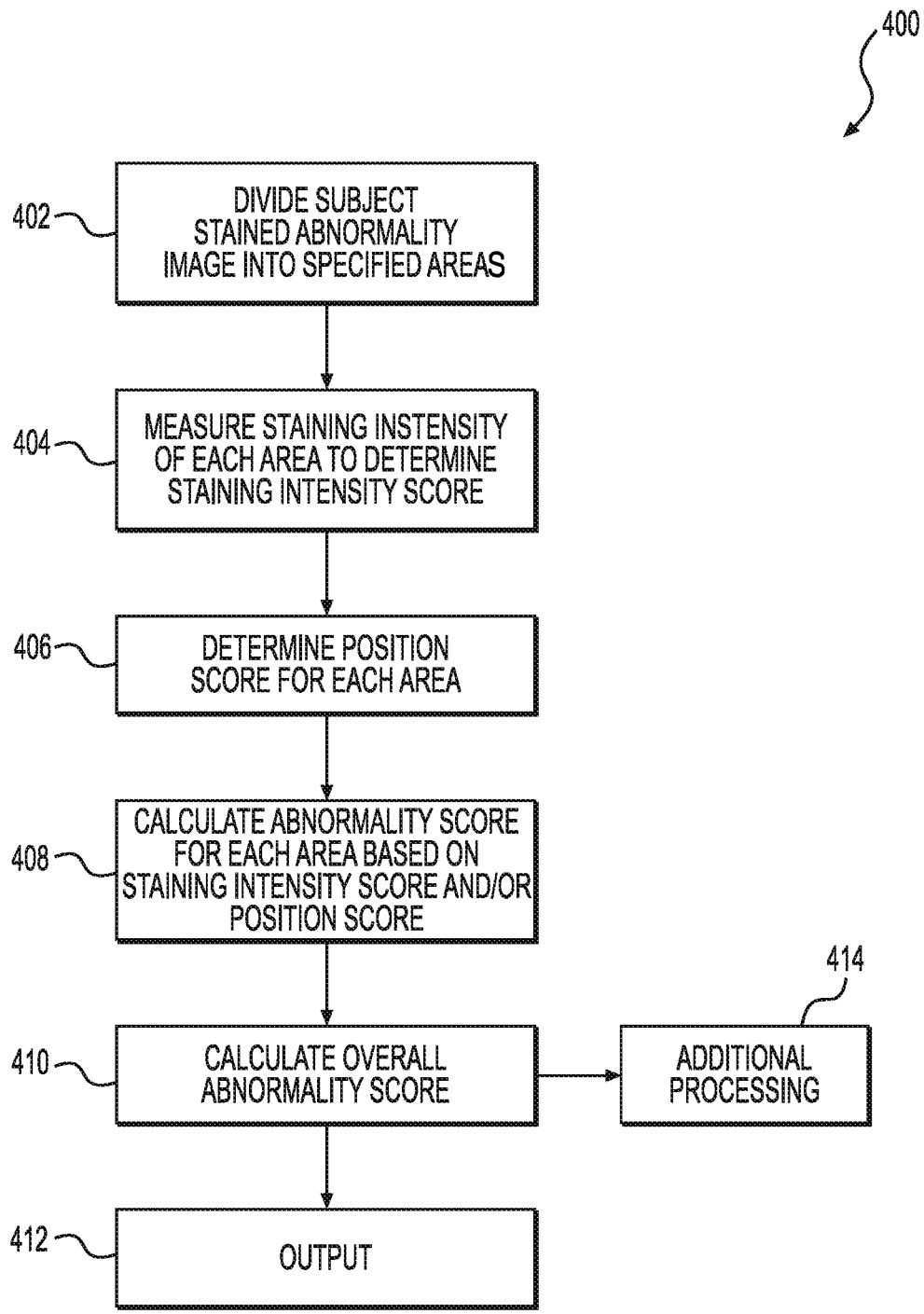
FIG. 15 is a flow chart of an exemplary method for generating abnormality scores for a subject to facilitate diagnosis of a severity level of gastric atrophy.

The abnormality score may be generated through the exemplary method 400 shown in FIG. 15. The method 400 of FIG. 15 includes dividing 402 the subject stained abnormality image by a specified area. For example, the subject stained abnormality image may be divided into 16×16 areas. Then, the staining intensity of each stained area of the image may be measured in step 404 to determine a staining intensity score. The staining intensity may be measured as, for example, a contrast area, such as a blue contrast area. Then, the measured staining intensity may be correlated to a particular staining intensity score.

For example, the staining intensity for each area may be measured by an image analysis device. Likewise, the staining intensity score may be determined by the same image analysis device or any other device. The image analysis device or other device may be the processor 12 (FIG. 1) or another processor or device that is part of the system 10 shown in FIG. 1. For example, computer-readable instructions for analyzing images to measure staining intensity and/or assign a corresponding staining intensity score for each image area may be stored in the storage device 14, such as the memory or another storage device.

As an example, if the measured staining intensity of a particular area is 0-50, then the staining intensity score for that area may be 0.1 points. If the measured staining intensity is 50-150, then the staining intensity score for that area may be 0.5 points. If the measured staining intensity is 150-255, then the staining intensity score for that area may be 0.8 points.

Then, in step 406, a position score for each stained area may be determined based on the position of each stained area. For example, if the stained area is positioned in a region known to be prone to atrophy or disease, then the stained area may be assigned a larger position score, whereas the position score may be lower if the stained area is positioned in a region not known to be prone to atrophy or disease or if the stained area is known to be resistant to atrophy.

The position score for each area may be determined by an image analysis device or the processor 12 (FIG. 1) or another processor or device that is part of the system 10 shown in FIG. 1. For example, the processor may execute computer-readable instructions and/or algorithms for analyzing images to determine a position of each stained area and/or assign a corresponding position score for each stained area. The computer-readably instructions may be stored in the storage device 14, such as the memory or another storage device.

As an example, the position factor may be 0.1 points for an atrophy-resistant area or an area not susceptible to atrophy, 0.5 points for an area known to have a small to moderate likelihood of atrophy, and 0.8 points for an area prone to atrophy.

In step 408, an abnormality score for each stained area may be calculated based on the staining intensity score determined in step 404 and the position score determined in step 406. For example, the staining intensity score 404 for each stained area may be multiplied by the position score 406 for each stained area to calculate the abnormality score 408 for each stained area. As an example, for a certain area, if the measured staining intensity is 100, and the area is an area prone to atrophy, then the abnormality score may be calculated as 0.4. That is, based on the above exemplary staining intensity and positions score ranges, the staining intensity score would be 0.5, and the position factor would be 0.8, resulting in an abnormality score of 0.5×0.8, which is 0.4. In other words, the staining intensity score 404 of each stained area may be weighted based on its position 406.

The above staining intensity score ranges and position score ranges are merely exemplary, non-limiting ranges. The staining intensity score and position score ranges may be determined by the user or may be determined based on the reference and/or standard image and non-image data.

Then, in step 410, the overall abnormality score may be calculated as a total of the abnormality scores 408 for the stained areas. In other words, the weighted score (abnormality score 408) for each stained area may be combined to determine an overall stained image abnormality score in step 410. For example, if the image was divided into 125 areas, and fifty areas were determined to have an abnormality score of 0.4, thirty areas were determined to have an abnormality score of 0.05, twenty-five areas were determined to have an abnormality score of 0.08, ten areas were determined to have an abnormality score of 0.64, and ten areas were determined to have an abnormality score of 0.01, the overall abnormality score may be calculated to be 30 (=(0.4×50)+(0.05×30)+(0.08×25)+(0.64×10)+(0.01×10)).

Alternatively, the staining intensity score may be the abnormality score, eliminating steps 406 and 408 in FIG. 15. In other words, the staining intensity score for each stained area determined in step 404 may be the abnormality score of each stained area such that the overall abnormality score may be calculated in step 410 as a total of the staining intensity scores for each area 404.

In any event, the overall abnormality score may be output 412 to the user, for example, via an output device 18, such as a display or a printer, or the overall abnormality score 410 may be output to a database or a server for storage. The overall abnormality score 410 may alternatively undergo additional processing in step 414 before being output to a user or server. Alternatively, a user may instruct the processor system 10 to perform additional processing 414 after output of the overall abnormality score 410.

Although the above description discloses calculating the abnormality score based on the subject abnormality image, the abnormality score could instead be calculated using the subject stained image or any other image derived from the subject stained image.

As discussed above with respect to FIG. 9, subject abnormality scores may be used to generate one or more visual representations to facilitate subject diagnosis. For example, one or more subject image abnormality scores and one or more subject non-image abnormality scores may be acquired and processed to generate a visual representation of the differences represented by the subject abnormality scores. Subject abnormality scores may be derived from dynamic data (e.g., video) or longitudinal data (e.g., data acquired at discrete points in time over a given period), and multiple visual representations corresponding to deviations at different points of time may be generated. The one or more visual representation may then be output to facilitate diagnosis of the subject in step. For abnormalities derived from dynamic or longitudinal data, multiple visual representations may be output simultaneously or sequentially.

Reference abnormality scores may be determined in the same manner for the reference abnormality images indicative of different severity levels of gastric atrophy. After dividing the reference abnormality images into specified areas, calculating the abnormality score for each area based on the staining intensity score and/or position score for each area, and calculating the overall reference abnormality score for each reference abnormality image, the reference abnormality scores may also be output to a server or database for storage, or may be output to a user. The reference abnormality scores may be calculated for several reference images representative of a particular severity level of gastric atrophy to determine a reference abnormality score range or average for each severity level of gastric atrophy. A reference abnormality score or average score or range for each particular severity level may be determined from a composite reference image generated from multiple reference abnormality images representative of the particular severity level of gastric atrophy.

As more subjects are diagnosed as having a particular severity level of gastric atrophy using the system and methods disclosed herein, the reference image database and standard image database for subjects that are determined to be healthy may be continuously or periodically updated. Likewise, the reference abnormality score, average score, or score range for each severity level of gastric atrophy may be continuously or periodically updated based on updated reference data.

Figure 16:
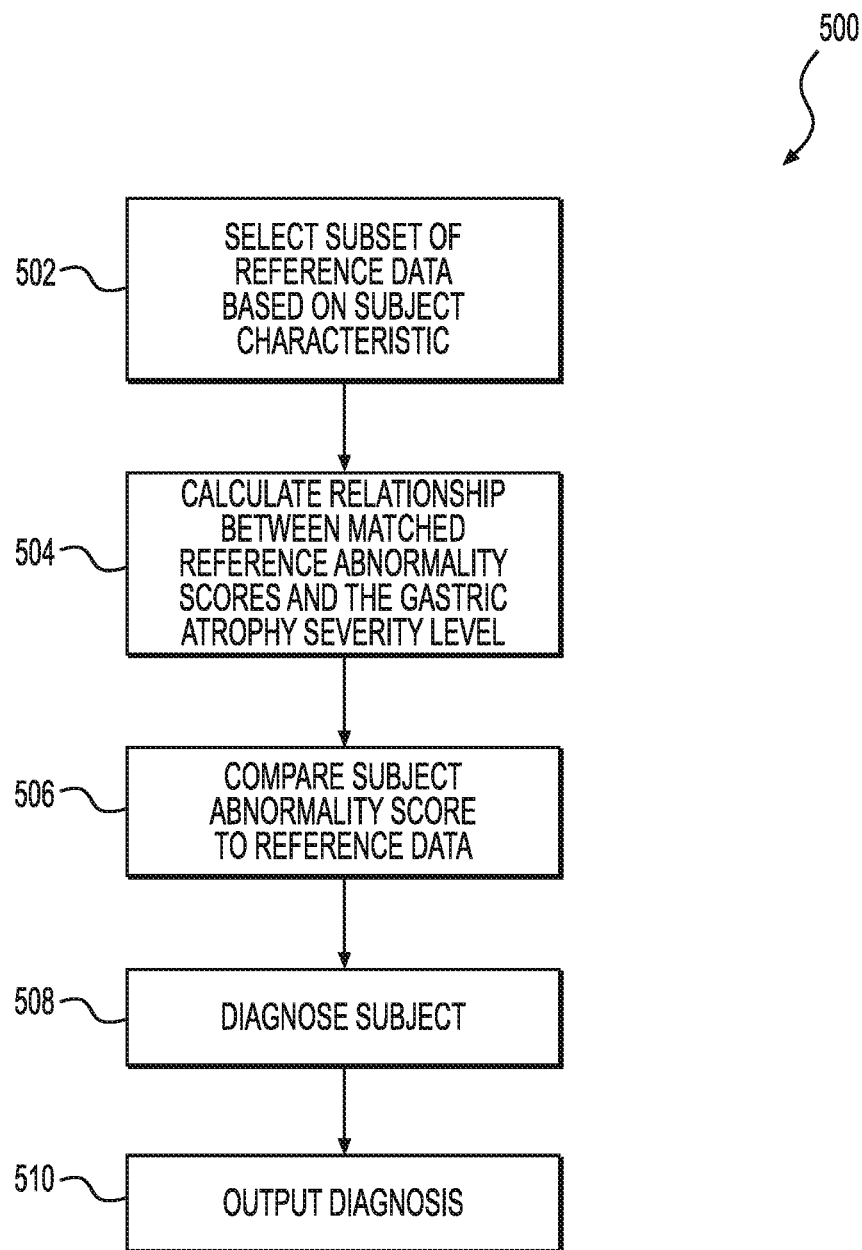
FIG. 16 is a flow chart of an exemplary method for diagnosing a severity of gastric atrophy and/or possibility of gastric cancer based on the subject abnormality score.

The present embodiment may further include systems and methods for diagnosing a subject with a particular severity level of gastric atrophy and/or diagnosing a likelihood of stomach cancer based at least in part of the abnormality score. An exemplary method 500 is shown in FIG. 16. In particular, the method 500 includes a step 502 of selecting a subset of reference data based on a subject characteristic, such as age, gender, or race, as discussed in more detail above. In step 504, a relationship is calculated between the abnormality scores and the gastric atrophy severity level of the matched reference data (e.g., that share a characteristic with the subject).

As an example, the matched reference data may include: (i) 10,000 subjects with a score of 0-20 points, of which 100 have a large degree of atrophy, and 50 have stomach cancer, (ii) 2,000 subjects with a score of 20-40 points, of which 600 have a large degree of atrophy, and 300 have stomach cancer, and (iii) 500 subjects with a score of 40-60 points, of which 400 have a large degree of atrophy, and 200 have stomach cancer. In this case, it may be determined that a subject with a score of 0-20 points has low severity gastric atrophy and a 0.5% possibility of stomach cancer, a subject with a score of 20-40 points has moderate severity gastric atrophy and a 15% possibility of stomach cancer, and a subject with a score of 40-60 points has high severity gastric atrophy, and a 40% possibility of stomach cancer.

For example, Table 1 shows an example correlation between the score and the likelihood of having a various severity level of gastric atrophy. For example, according to Table 1, if the subject has a score of 50, the probability of being normal is 10% (=200/2000), the probability of low degree gastric atrophy is 20%, the probability of moderate degree gastric atrophy is 30%, and the probability of high degree gastric atrophy is 40%.

TABLE 1

| Score | Number | Normal | Low Degree | Moderate Degree | High Degree |
| --- | --- | --- | --- | --- | --- |
| 0-20 | 5000 | 3000 (60%) | 1500 (30%) | 450 (9%) | 50 (1%) |
| 20-40 | 3000 | 2000 (67%) | 500 (17%) | 400 (13%) | 100 (3%) |
| 40-60 | 2000 | 200 (10%) | 400 (20%) | 600 (30%) | 800 (40%) |

In step 506, the subject abnormality score is compared to the Reference Data. Based at least in part on that comparison, the subject is then diagnosed in step 508 as having a particular severity of gastric atrophy and/or the possibility of stomach cancer. For example, if the subject has an overall abnormality score of 30, then the subject may be diagnosed as having moderate severity gastric atrophy and a 15% possibility of stomach cancer. The diagnosis may be output to a user, such as a doctor or technician via a display or printer or other output device 18, and/or the diagnosis may be stored on a server or database in, for example, a storage device 14.

The exemplary diagnostic processor system 10 shown in FIG. 1 may be used to facilitate diagnosis of the severity level of gastric atrophy of the subject and/or possibility of stomach cancer. For example, computer-readable instructions for analyzing and/or processing stained images and data, generating abnormality images, calculating abnormality scores, performing or facilitating diagnosis of a particular severity level of gastric atrophy and/or possibility of stomach cancer may be stored in the storage device 14, such as the memory. The processor 12 may execute the computer-readable instructions to facilitate diagnosis of the subject. As an output device 18, a display may be configured to display one or more of: the subject stained image, the subject abnormality image, the standard stained image, the reference stained images, the reference abnormality images, non-image subject data, a subject deviation score, and the diagnosis received from the processor.

Based on the diagnosis of the severity of gastric atrophy, the subject may be appropriately treated. The processor may determine which treatment is appropriate based on the severity level of gastric atrophy and output treatment information accordingly. For example, medications that block acid production and promote healing may be administered. Such medications including proton pump inhibitors, such as omeprazole, lansoprazole, rabeprazole, esomeprazle, dexlansoprazole, and pantoprazole. Proton pump inhibitors reduce acid by blocking the action of the parts of the cells that produce acid. Acid blockers or histamine (H-2) blockers may be administered to reduce the amount of acid released in the subject's digestive tract. Such acid blockers include ranitidine, famotidine, cimetidine, and nizatidine. Antacids may also be administered to neutralize exciting stomach acid and provide pain relief. Additionally, antibiotic medications may be administered to kill *H. pylori* in the subject's digestive tract. Such antibiotics may include clarithromycin, amoxicillin, and metronidazole. Further, stomach coating drugs, such as bismuth subsalicylate, that help protect the tissues that line the stomach and small intestine may be administered.

For example, in the treatment of acute gastritis (low degree gastric atrophy), elimination of the cause is important. If the cause is clear, such as stress or drug use, it may be treated by removing the cause. If nausea and vomiting are severe, fasting, feeding by drip infusion, and treatment with gastric acid secretion inhibitors and gastric mucosal protective agents may indicated. If there is bleeding in the gastric mucosa, then use of a hemostat may be indicated.

In the case of chronic gastritis (moderate severity gastric atrophy), the subject may be treated with a drug that suppresses gastric acid secretion. It may be used in combination with gastric mucous membrane protective drugs and stomach movement function improving drugs.

For atrophic gastritis (high severity gastric atrophy), removal of *H. pylori* is indicated. In the eradication therapy, two types of antibacterial drugs and one type of proton pump inhibitor (a drug that suppresses the secretion of gastric acid) may be taken twice daily for 7 days. This therapy may be used to eliminate at least about 70% of bacteria. For remaining bacteria, the subject should be treated again with a different combination of antibacterial agents (secondary eradication therapy). This should eliminate about 90% of bacteria.

Blood Vessel Images to Facilitate Diagnosis of Severity of Gastritis

In an exemplary embodiment, a diagnostic system, method, and computer-readable storage medium for determining or facilitating diagnosis of a severity of gastritis in a subject is provided. Chronic inflammation of the stomach results in thinning of the stomach's mucosa, allowing submucosal blood vessels to be imaged, for example, by an endoscope. Progression of chronic gastritis leads to progression of superficial gastritis, atrophic gastritis, and intestinal metaplasia, and can eventually lead to gastric cancer. The present systems, methods, and computer-readable media diagnose the severity of gastritis based on the contrast between the stomach wall and a blood vessel in stomach wall images.

Figure 17:
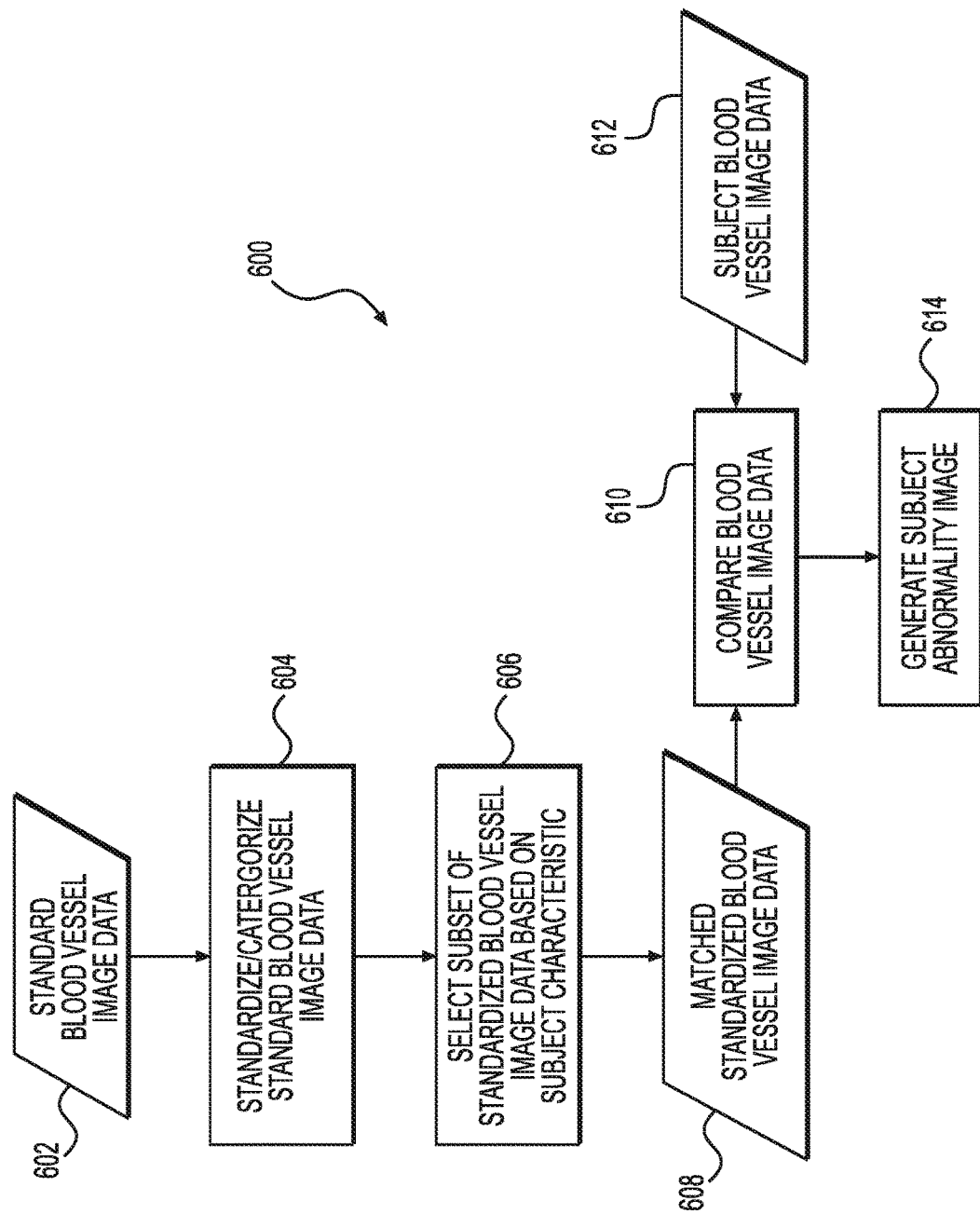
FIG. 17 is a flow chart of an exemplary method for generating subject abnormality images to facilitate diagnosis of a severity level of gastritis.

In the case of a normal gastric mucosal structure shown in FIG. 17, since a mucosal layer of a stomach is increased in thickness, most of light is absorbed or reflected in the mucosal layer. In contrast, in a case of a mucosal structure in which gastritis has progressed, a thickness of the mucosal layer is decreased with a decrease in the number of gastric gland cells. The change of the internal structure of the gastric mucosa with the progression of gastritis results in changes in an endoscopic image. For example, lamina muscularis mucosae, which is normally a color close to white, becomes transparent, and the color of atrophic mucosa becomes a faded color compared to a normal part. In an area where there is an atrophic mucosa, when a mucosal layer is decreased in thickness with atrophy, a blood vessel of a submucosa becomes visible in an endoscopic image.

An image of the gastric wall of the subject is obtained using an endoscope. The image may be a color image that has a pixel level (pixel value) for each wavelength component of R (red), G (green), and B (blue) in each pixel position. Each value of RGB may be stored in memory. The image may be color converted such that only green (G) is extracted in order to highlight blood vessels in the image. For example, an image may be acquired and color converted into a green (G) wavelength component image using known conversion processes. The G component may be used because it is close to an absorption wavelength band of hemoglobin in blood so that structural information of the intraluminal image, such as the structure of a blood vessel in the mucous membrane, is properly represented. The G-component image may then be processed to remove noise, enhance edges and lines, and sharpen the image. Then, as discussed below, the brightness value of green (G) may be calculated as the luminance value.

Such images show a contrast between the gastric wall and a blood vessel of the subject. The subject contrast images are compared with reference contrast images to determine the severity of gastritis based on a degree of permeation of a blood vessel. The subject contrast images and/or reference contrast images may be stored on a server or in a database.

Reference contrast images (e.g., of stomachs of individuals with different severity levels of gastritis) and standard contrast images (e.g., of healthy stomachs) may be obtained in the same manner discussed above. These contrast images, like the subject contrast image(s), show a contrast between the gastric wall and a blood vessel of the subject. For example, reference data, including contrast image data and non-image data, may be collected from people or groups of people. Such people may include healthy people that are not suffering from gastritis, and other people suffering from different severity levels of gastritis. The reference contrast image and non-image data may be standardized and categorized according to one or more characteristics, as discussed above. For example, such reference data may be categorized based on population characteristics, such as race, gender, or age of the people from which the data was collected. Standardized data permits average stomach characteristics to be calculated for healthy subjects and subjects with different severity levels of gastritis.

The standard contrast image may be an earlier contrast image of the subject in a healthy state or may be a contrast image of a stomach of a different person in a healthy state. As discussed in more detail below, the different person may be selected based on one or more shared characteristics with the subject, such as age, race, and sex.

An abnormality contrast image of the subject's stomach may be generated through any suitable technique. For example, an abnormality image may be generated by comparing the subject contrast image with a standard contrast image as discussed above. For example, a difference image between the subject contrast image and the standard contrast image of a healthy stomach may be obtained as a subject abnormality image. Prior to comparing the subject contrast image and the standard contrast image, the subject contrast image and standard image may undergo preprocessing to extract or enhance certain areas or anatomical features, such as blood vessels, according to any known methods. The images may also be standardized to facilitate comparison and analysis.

The abnormality image may be a representative image in which each point of the image represents a score generally corresponding to a number of standard deviations (based on a selected population) in the difference between a subject value (e.g., contrast intensity) and the average value (e.g., contrast intensity) of the population for that point. Abnormality images may be generated from image data and/or one or more of numerical data, text data, waveform data, image data, video data, and the like.

The image(s) may be visualized to facilitate further analysis or diagnosis. For instance, any or all of the standard contrast images, subject contrast image, subject abnormality images, and reference contrast images (discussed below) may be expressed as surface matrices, and can be displayed or overlaid on a three-dimensional (3D) stomach surface.

An exemplary method 600 for generating abnormality images, indicative of differences between a region of the subject contrast stomach image and a region of a standard contrast stomach image, is illustrated in FIG. 17. Standard contrast image data (e.g., standard blood vessel image) is obtained in step 602, and is categorized and standardized in step 604. Standard contrast image data and non-image data may be collected from people and categorized or standardized according to one or more desired characteristics, such as age, gender, or race. While the presently illustrated embodiment is described with respect to contrast image data, it is noted that reference non-image data and subject non-image data may also, or instead, be used to generate the abnormality images discussed herein.

The method 600 may include selecting a subset of the standard contrast image data based on a subject characteristic, such as age, race, or gender in step 606, as discussed above with respect to FIG. 3 (e.g., step 54) and 10 (e.g., step 206). Once a desired group of standard contrast image data is selected, the matched standard contrast image data 608 may be compared to contrast image data 612 of the subject (e.g., subject blood vessel image data) in step 610. Non-image data of the subject may instead or also be compared to matched standard non-image data, as described above. Additionally, the various data may be processed and categorized in any suitable manner to facilitate such comparisons. In step 614, a subject abnormality image may be generated based at least in part on the comparison 610 between the matched standard contrast image data 608 and the subject contrast image data 612.

Figures 18A, 18B, 18C, 18D:
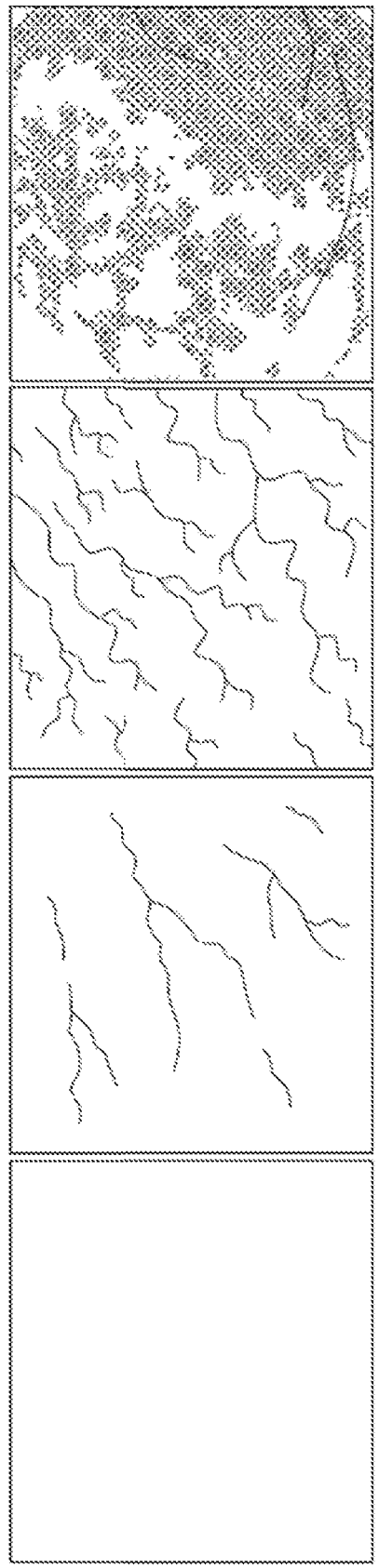
FIGS. 18A-D are exemplary abnormality images of stomach walls showing contrast between the stomach wall and a blood vessel.

Exemplary subject abnormality images are shown in FIGS. 18A-D. FIG. 18A shows a healthy stomach with no signs of gastritis. FIG. 18B shows an abnormality image of a stomach with low severity gastritis (superficial gastritis). FIG. 18C shows an abnormality image of a stomach with moderate severity gastritis (atrophic gastritis). FIG. 18D shows an abnormality image of a stomach with high severity gastritis (intestinal epithelialization/intestinal metaplasia). As shown in FIGS. 18A-18D, a degree of contrast of the blood vessels represents a degree of permeation of the blood vessel through the mucosa (e.g., visibility of the blood vessel through the mucosa), or deviation from normal, to facilitate a user's understanding of the represented anatomical information.

For example, in the healthy stomach shown in FIG. 18A, there is no contrast between the blood vessels and the stomach wall, indicating that the mucosal thickness throughout the stomach is within healthy ranges and there are no signs of gastritis. In the stomach abnormality image of FIG. 18B, there is some contrast between some blood vessels and the stomach wall, indicating that the mucosal thickness is slightly to moderately below healthy ranges, which corresponds to low severity gastritis (e.g., superficial gastritis). In the stomach abnormality image of FIG. 18C, there is increased contrast between even more blood vessels 634 and the stomach wall, indicating that the mucosal thickness is moderately below healthy ranges, which corresponds to moderate severity gastritis (atrophic gastritis). Lastly, FIG. 18D shows a stomach abnormality image in which the blood vessels cannot be seen and the stomach wall appears to be different from that in FIGS. 18A-D. This may be is indicative of intestinal epithelialization (intestinal metaplasia) and is indicative of high severity gastritis.

Subject contrast images generated over a period of time may be compared to determine a change in the stomach of the subject over time. For example, subject contrast images may be obtained, for example, once a year, twice a year, every two years, or any other time period. When a new subject contrast image is collected, it may be compared with one or more earlier subject contrast images to analyze changes in the subject contrast images over time. Difference (e.g., abnormality) images may be generated by subtracting earlier subject contrast images from the latest subject contrast image. Such difference images may serve to emphasize the changes between the subject contrast images collected at different points in time.

For example, the comparison may reveal that a contrast of the blood vessels has increased compared to the earlier contrast image, indicating that gastritis has advanced or become more severe. Alternatively, if the earlier subject image showed a high contrast between blood vessels and the stomach wall, and a later subject image no longer shows a high contrast or no longer shows blood vessel at all, it may be determined that intestinal epithelialization (intestinal metaplasia) has occurred (e.g., FIG. 18D).

Figure 19:
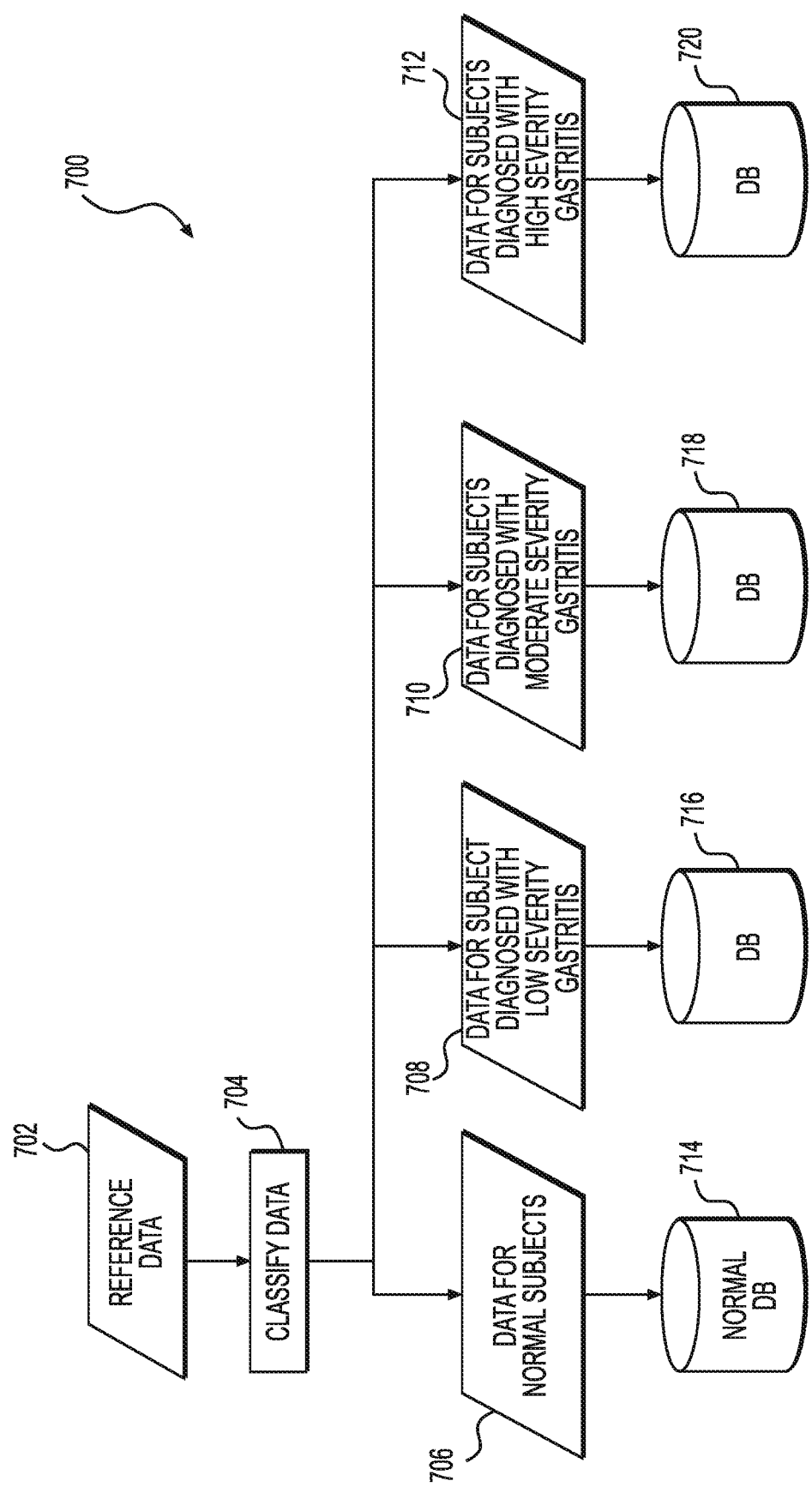
FIG. 19 is a flow chart of an exemplary method for categorizing reference and standard data to facilitate diagnosis of a severity level of gastritis.

Additionally, reference contrast image data may be categorized and sorted into standardized databases, such as through an exemplary method 700 shown in FIG. 19. The method 700 may include acquiring reference data 702, which may include contrast image and non-image data from various people, and categorizing the data in step 704. For example, the reference data 702 may be categorized into various groups, such as normal (healthy) subject data 706, data 708 of subjects clinically diagnosed with low severity gastritis, data 710 of subjects diagnosed with moderate severity gastritis, and data 712 of subjects diagnosed with high severity gastritis. The data 706, 708, 710, and 712 may be stored in respective databases 714, 716, 718, and 720. Such databases may be stored on a server, in one or more memory or storage devices, and/or in other suitable media. Such databases may be continuously or periodically updated as more subjects are diagnosed. As discussed above, the data 706, 708, 710, and 712 in each database 714, 716, 718, and 720 may be further standardized and classified according to various subject characteristics, such as age, gender, and race.

Figure 20A:
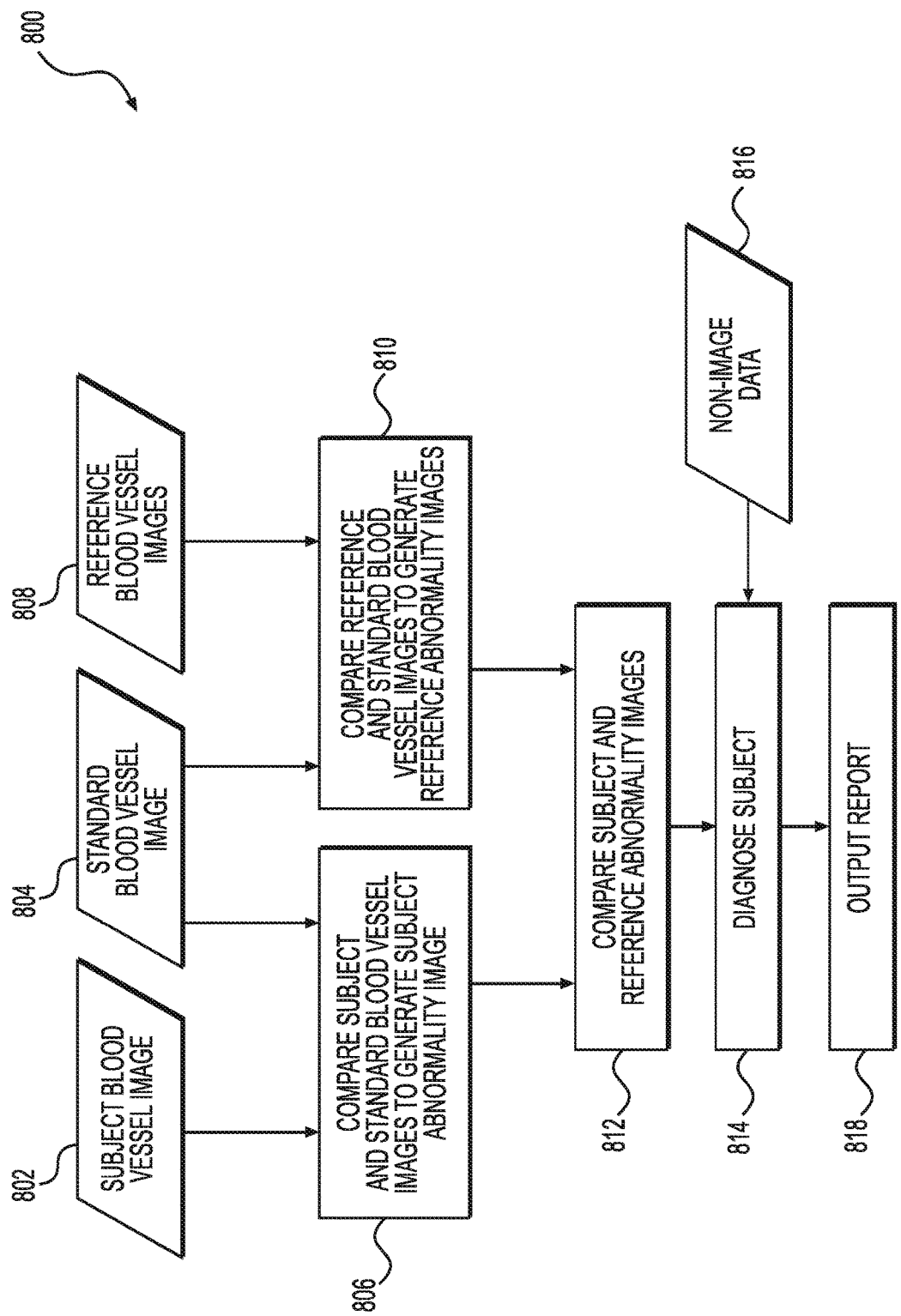
FIGS. 20A-D are flow charts of an exemplary method for diagnosing a severity level of gastritis via blood vessel images.
Figure 20B:
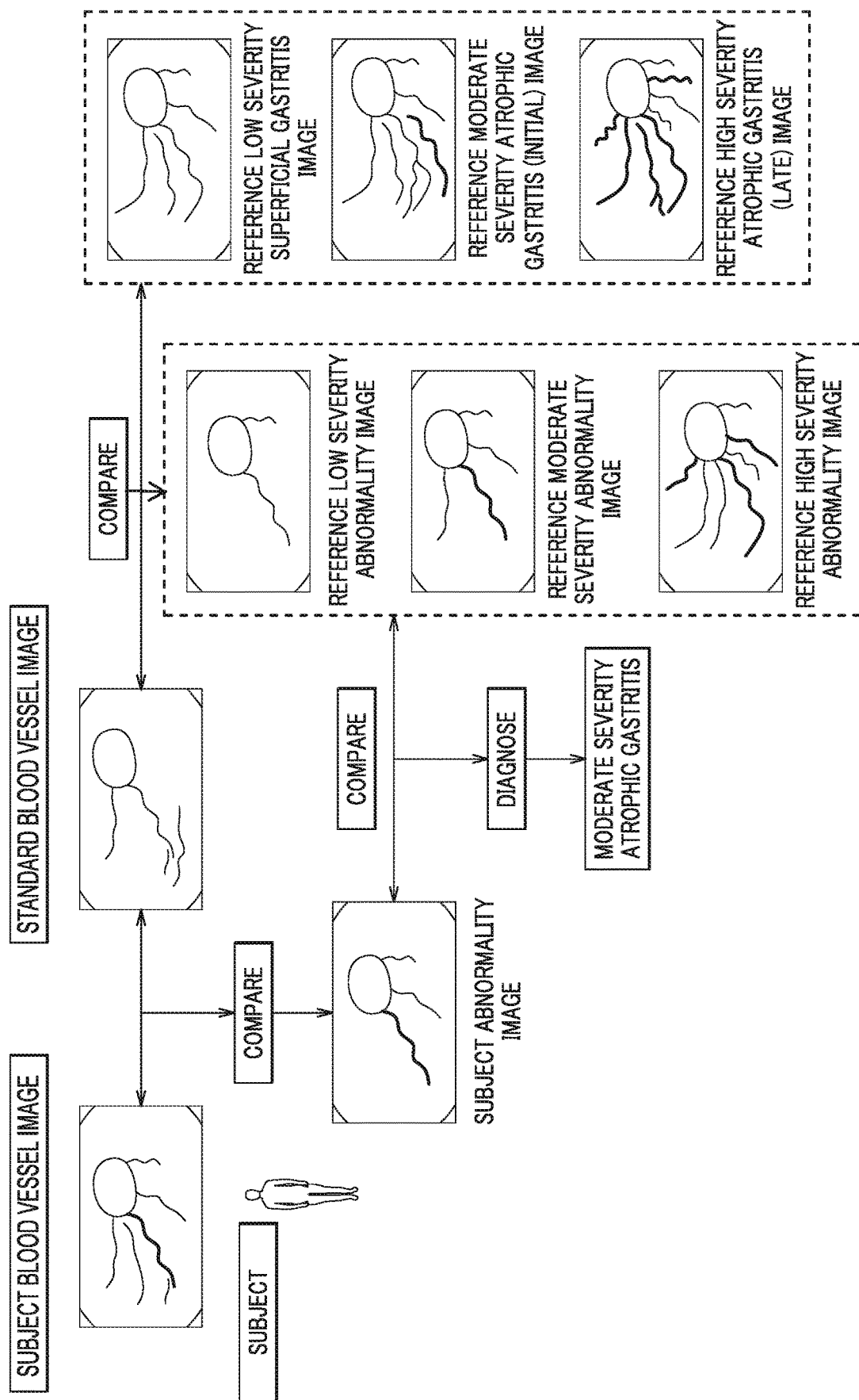

Exemplary methods for diagnosing a subject with a particular severity of gastritis based at least in part of the foregoing data is shown in FIGS. 20A-B. For example, in FIG. 20A, the method 800 may include obtaining contrast image(s) of the stomach of the subject 802, and comparing the subject contrast image(s) 802 with standard contrast image(s) 804 of healthy stomachs to generate a subject abnormality image 806, which is indicative of differences between the subject contrast image(s) and the standard contrast image(s).

Further with respect to FIG. 20A, reference contrast images 808 of stomachs exhibiting different severity levels of gastritis are also compared 810 to the standard contrast image(s) 804 to generate reference abnormality images, which are indicative of differences between the reference contrast images 808 and the standard contrast image(s) 804. Reference contrast images 808 may be standardized images acquired from a database of reference contrast images 808 for each severity level of gastritis collected from a particular group of people diagnosed with a particular severity level of gastritis, as discussed above. The reference contrast images 808 may be the actual contrast images, optionally processed to enhance or extract the structural feature of interest, collected from the people of a particular group or characteristic category. Alternatively, the reference contrast images 808 may be average images created based on the data collected from the people of a particular population diagnosed with a particular severity level of gastric atrophy. For example, a representative average contrast stomach image for each severity level of gastritis may be generated. Thus, multiple representative or average contrast images may be created for each severity level of gastritis.

The subject abnormality image 806 is then compared 812 with the reference abnormality images 810. All of the images may be standardized into one or more common or similar formats to facilitate analysis and comparison. The subject is diagnosed 814 as having a particular severity level of gastritis based at least on part on the comparison between the subject abnormality image the reference abnormality images. The diagnosis 814 may also be made by taking other data 816 and analysis into consideration, including non-image data, such as clinical data, laboratory data, subject history, family history, subject vital signs, results of various tests (e.g., genetic tests), and any other relevant non-image data. Based on the subject and reference data, numerous reference and subject abnormality data and images may be created. Then, a report 818 of the diagnosis 814 is output, for example, to an output device 18 (shown in FIG. 1), such as a display or a printer, or to a database or server for storage, or to a user in a human-readable format.

FIG. 20B shows an exemplary process in which a subject is diagnosed with moderate severity gastritis based on a comparison of subject contrast images with reference contrast images. One or more blood vessel contrast images of the subject are compared with one or more standard contrast images to generate a subject abnormality image. For instance, in FIG. 20B, the standard contrast image is subtracted from the subject contrast image to generate a difference image (subject abnormality image). As shown in FIG.

20B, the subject abnormality image shows the contrast differences between the subject contrast image and the standard contrast image and eliminates shared contrast between the images. The contrast differences shown in the subject abnormality image are indicative of abnormalities or deviations from normal.

Reference abnormality images (representative of various severity levels of gastritis) are compared to the standard contrast image in the same manner to generate reference abnormality images (representative of various severity levels of gastritis). For example, in FIG. 20B, the standard contrast image is subtracted from each reference contrast image to generate a corresponding reference difference (abnormality) image. Then the subject abnormality image is compared to the reference abnormality images to make a diagnosis. Not only the area or amount of luminance, but also the intensities (saturation) of the contrast areas in the abnormality images are compared. In FIG. 20B, the subject abnormality image most closely resembles the reference abnormality image representative of moderate severity gastritis. Therefore, based at least in part on this comparison, the subject is diagnosed with moderate severity gastritis in the example shown in FIG. 20B.

The generation of the subject and reference abnormality (e.g., difference) images enables the abnormalities and deviations in the subject contrast image to be visualized, thereby facilitating accurate and consistent diagnoses to be made. Such differences cannot be as easily detected by simply viewing and comparing the subject and reference images. Additionally, as discussed in more detail below, the images can be analyzed for, for example, contrast intensity to further ensure objective and consistent diagnoses are made.

Figure 20C:
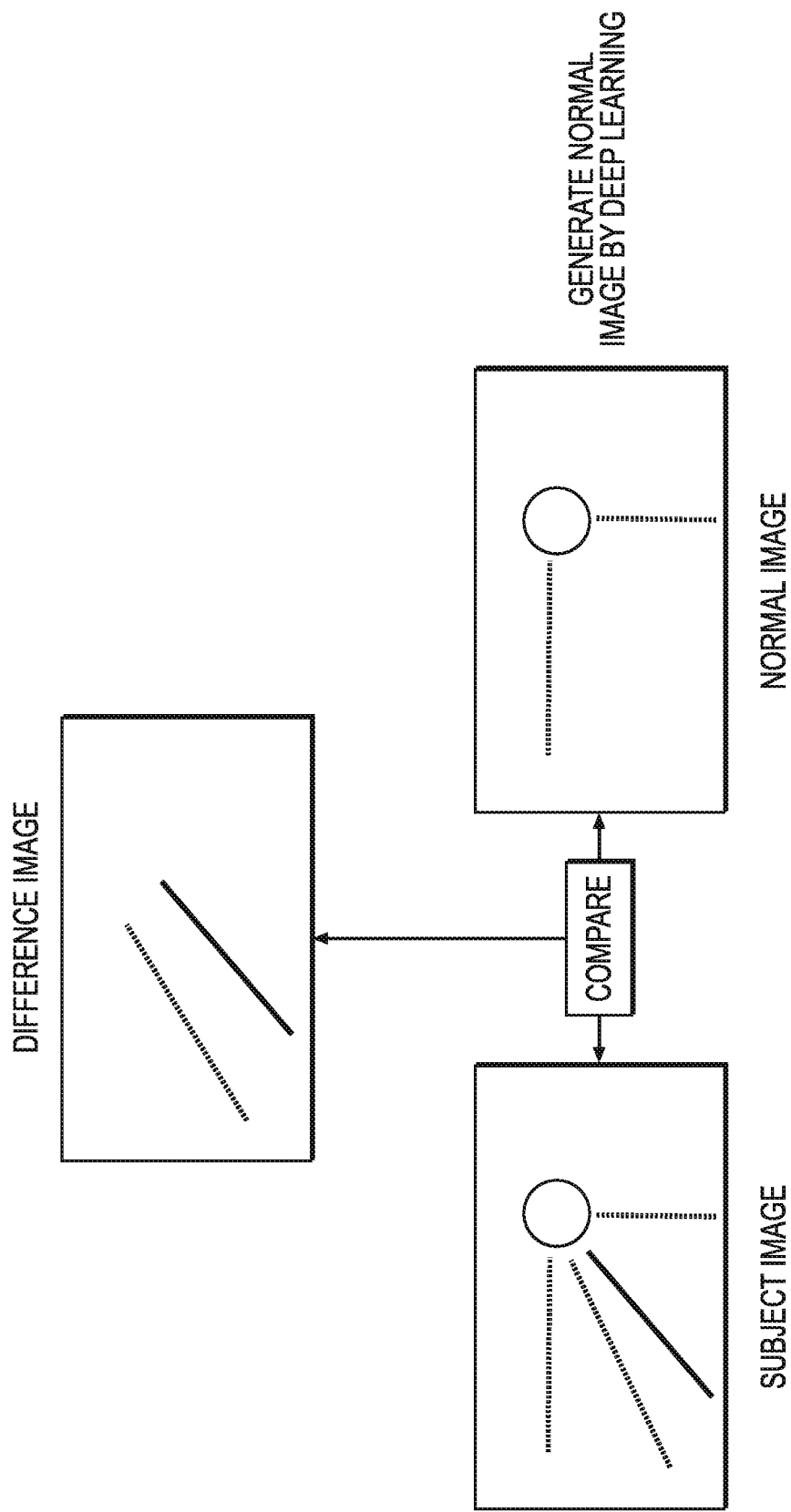
Figure 20D:
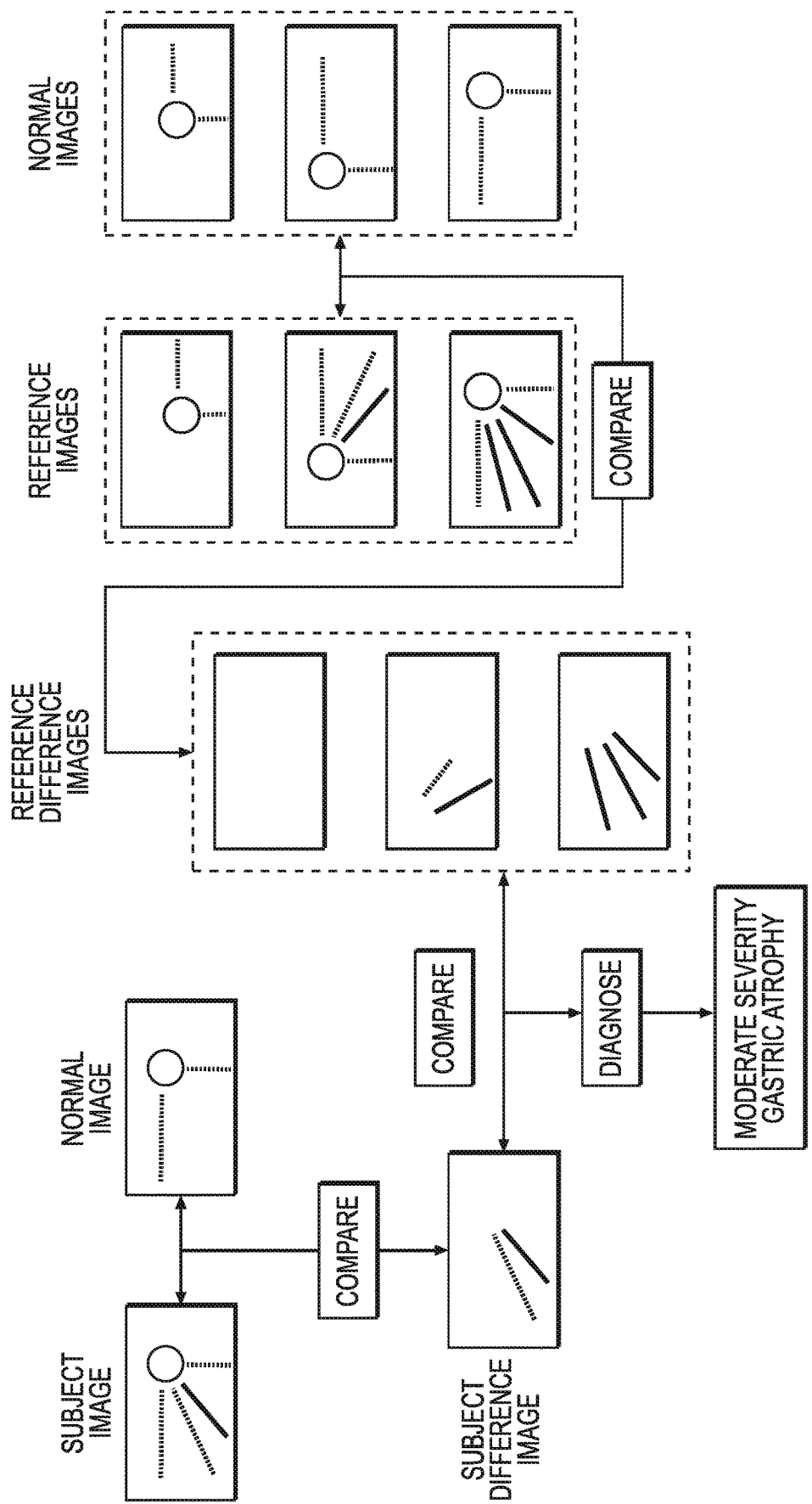

FIG. 20C shows an example where the subject difference image is generated from a subject blood vessel image and a normal blood vessel image generated by deep learning techniques. Similarly, as shown in FIG. 20D, reference difference images may be generated from reference blood vessel images representative of various severity levels of gastritis and normal blood vessel images selected by deep learning techniques. That is, instead of comparing the subject and reference images with the same normal (e.g., standard) image, the present systems and methods employ deep learning techniques to generate normal blood vessel images for use in generating the reference and subject differences images.

For example, as discussed above, a deep learning model, such as a VAE, may be trained to generate corresponding normal images. Such training may be unsupervised learning in which only normal blood vessel images are input into the model for training. Such normal training images may be blood vessel images of healthy stomachs that are substantially free of abnormalities. The model may be trained via an iterative process involving compressing and reconstructing input normal blood vessel images by an encoder and a decoder to extract and learn features and patterns of normal blood vessel images without external identification.

Once learned, the model can be given a blood vessel image of a stomach to predict whether it is normal or abnormal. Because the trained model has been trained using only normal blood vessel images, it can detect features different from normal blood vessel images as abnormal features. Additionally, when given an abnormal blood vessel image, such as a reference image indicative of a particular severity level or an abnormal subject image, the trained model can generate a corresponding normal blood vessel image by compressing the abnormal image and restoring the compressed image as a normal blood vessel image in which the abnormal features are omitted. That is, the trained model generates a normal blood vessel image from the abnormal image. The abnormal feature(s) in the original image are restored as normal feature(s) in the restored blood vessel image (generated normal blood vessel image).

Therefore, as illustrated in FIGS. 20C and 20D, a normal blood vessel image may be generated from a subject blood vessel image and normal blood vessel images may be generated from reference blood vessel images for each severity level by deep learning. In other words, deep learning may be used to generate normal blood vessel images that correspond to reference blood vessel images for each severity level or correspond to the subject blood vessel image except that abnormal part(s) have been removed. Then, the subject and reference difference images may be obtained by pattern matching. By using deep learning, a pseudo-normal blood vessel image can be accurately generated, and an accurate difference image can be generated. Additionally, it is sufficient to train the deep learning device or network using only normal training images, and it is not necessary to train with abnormal images. Therefore, the amount of data necessary for training the deep learning device or network can be reduced. Collecting a large amount of abnormal data (e.g., abnormal images) is difficult. Thus, reducing the burden of collecting a large amount of data is a significant advantage.

The various images and data described herein may be stored in one or more databases to facilitate subsequent data analysis. Moreover, any or all of the foregoing comparisons may be performed either automatically by a data processing system, such as system 10, or by a medical professional, such as a doctor, or by some combination thereof, to facilitate automatic or manual diagnosis of the subject in step 814.

Figure 21:
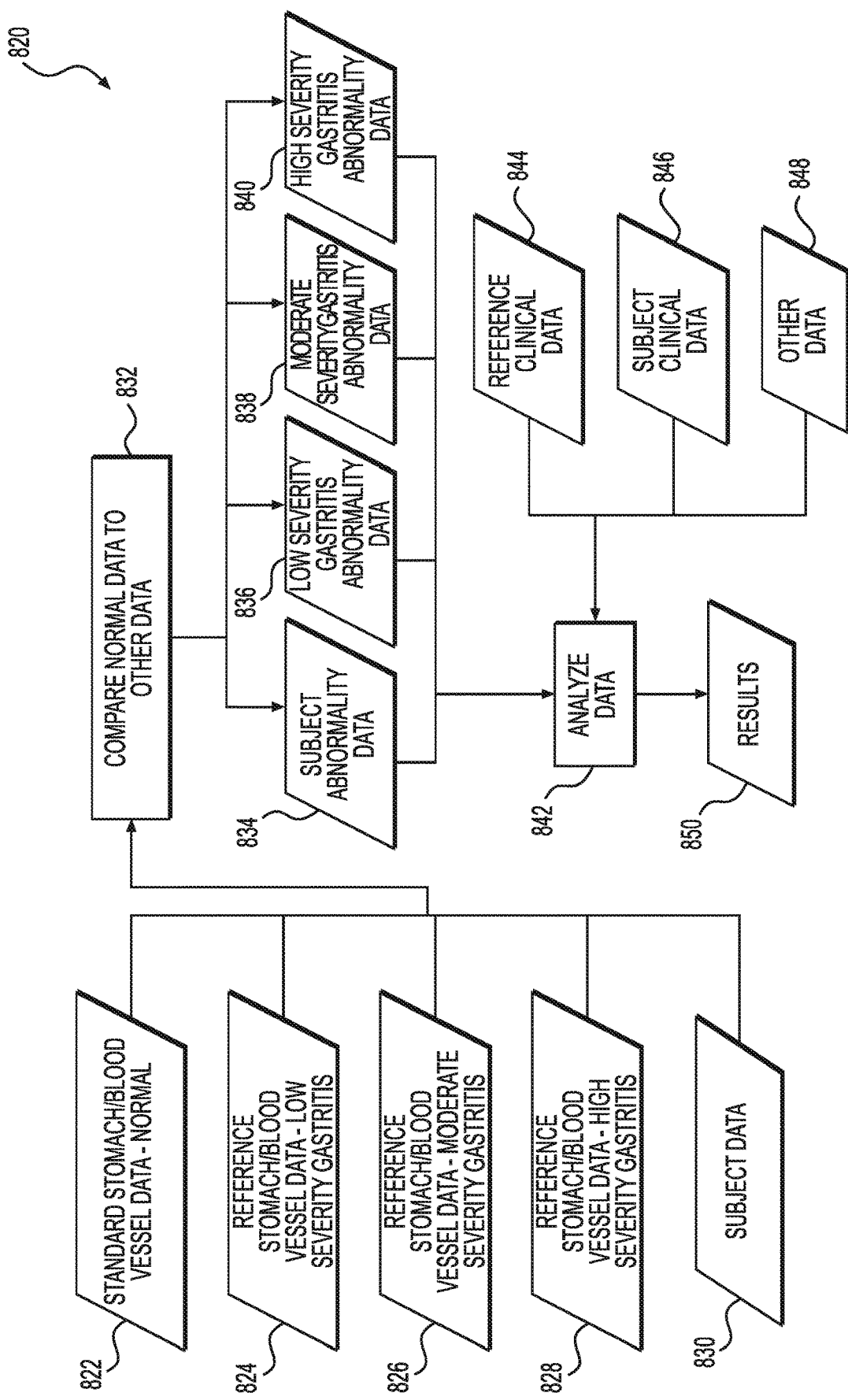
FIG. 21 is a flow chart of an exemplary method for generating and analyzing abnormality data to facilitate diagnosis of a severity level of gastritis.

Based on the subject and reference contrast image and non-image data discussed above, numerous reference and subject abnormality data and images may be created. By way of example, an exemplary method 820 for generating and analyzing such abnormality data is shown in FIG. 21. The method 820 includes acquiring reference stomach data, including reference contrast images, for: normal subjects without gastritis (data 822) (e.g., standard data, including standard contrast image(s)), subjects clinically diagnosed with low severity gastritis (data 824), subjects diagnosed with moderate severity gastritis (data 826), and subjects diagnosed with high severity gastritis (data 828). The method 820 may also include acquiring subject stomach data 830, including subject contrast images.

In step 832, the standard data 822 may be compared to each of the other data 824, 826, 828, and 830, to generate low severity gastritis abnormality data 836, moderate severity gastritis abnormality data 838, high severity gastritis abnormality data 840, and subject abnormality data 834, all of which may represent deviations from the standard/normal data 822. Such abnormality data may include structural abnormality images representative of differences between the subject data 830 and: (i) the reference data 824, 826, and 828 for the particular severity level of gastritis, and/or (ii) the standard data 822.

Structural abnormality images may show deviations in blood vessel visibility (e.g., permeation) through mucosa (e.g., blood vessel contrast), or mucosal thickness from normal, healthy ranges for a particular population. For example, the higher the blood vessel contrast (e.g., the higher the blood vessel visibility/permeation through the mucosa), or the thinner the mucosa, the more severe the atrophy, indicative of low or moderate gastritis. On the other hand, no blood vessel contrast is indicative of a normal, healthy stomach. The structural abnormality images may also show deviations in surface, foveolar, and glandular epithelium in the oxyntic or antral mucosa, such as replacement by intestinal epithelium, which is indicative of severe gastritis.

In step 842, such abnormality data may be analyzed. For example, a subject abnormality image or data may be compared to representative reference abnormality images to facilitate diagnosis of the subject with respect to a particular severity level of gastritis. Additionally, reference clinical data 844, subject clinical data 846, and other data 848 may also be analyzed by a data processing system or a user to facilitate diagnosis. Such analysis may include pattern matching of subject images and reference images, and confidence levels of such matching may be provided to a user. Finally, results 850 of the analysis may be output to a database or server, a storage device, and/or to a user via, for example, an output device 18, such as a display or printer.

The extent of subject deviation from standard data may also be translated into one or more abnormality scores, which may be generated through the methods shown in FIGS. 7 and 8, discussed above. For example, with reference to FIG. 7, the method 140 may be include accessing subject image data 142 (e.g., contrast image data) and reference image data 144 (e.g., contrast image data), including standard contrast image data and contrast image data representative of a particular severity level of gastritis. Such contrast image data may be received from any suitable source, such as a database or an imaging system, such as an endoscope. The contrast image data 142 and 144 may include contrast image data collected from a wide range of sources. The reference contrast image data 144 may be standardized according to any desired characteristics. For instance, the reference contrast image data 144 may be standard contrast image data generally representative of features of normal (e.g., healthy) individuals with certain characteristics, for example, characteristics similar to the subject. In step 146, the subject contrast image data 142 and the reference contrast image data 144 may be compared to determine deviations of the subject contrast image data 142 from the reference contrast image data 144. Such differences may generally represent deviation, for example, structural differences between the subject and normal (e.g., healthy) subjects.

The method 140 may also include calculating 148 one or more subject contrast image abnormality scores for differences between the subject contrast image data 142 and the reference contrast image data 144. Such abnormality scores may be indicative of an array of structural deviations of the subject relevant to the reference contrast image data. The subject contrast image abnormality scores may be calculated in various manners according to any suitable technique. The calculated subject contrast image abnormality scores 150 may then be stored in a database 152, output to a user, or may undergo additional processing in one or more further steps 154. The method 160 of FIG. 8 of calculating a subject non-image abnormality score, which is discussed in more detail above, may also be calculated for diagnosing or facilitating diagnosis of a particular severity level of gastritis.

Figure 22:
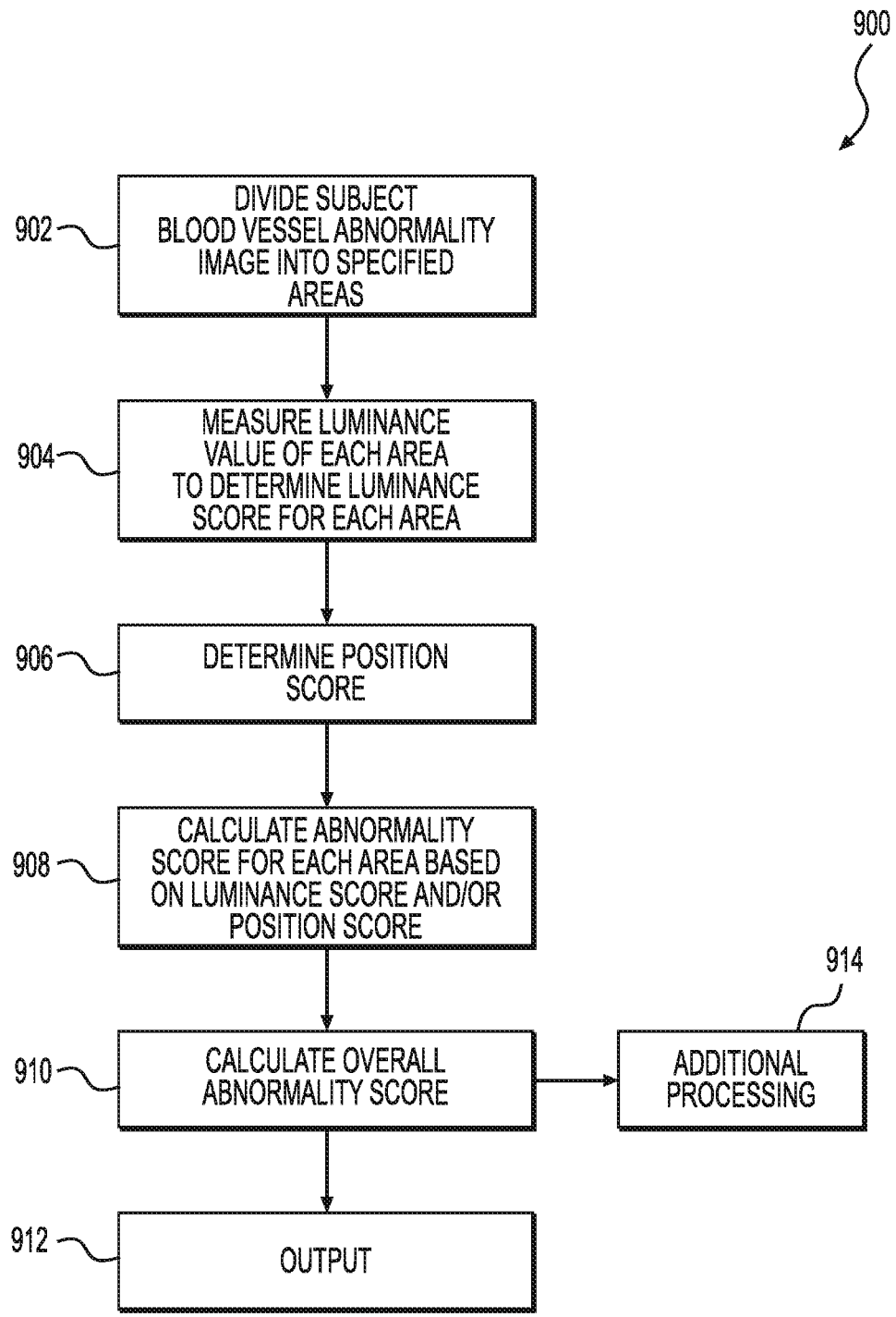
FIG. 22 is a flow chart of an exemplary method for generating abnormality scores for a subject to facilitate diagnosis of a severity level of gastritis.

The abnormality score may be generated through the exemplary method 900 shown in FIG. 22. The method 900 of FIG. 22 includes dividing 902 the subject blood vessel abnormality image by a specified area. For example, the subject abnormality image may be divided into 16×16 areas. Then, the luminance value of each contrast area of the image may be measured in step 904 to determine a luminance score.

The luminance value may be measured by color converting the image to extract only green (G) and measuring the brightness value of green (G) as the luminance value. Then, the measured luminance value may be correlated to a particular luminance score.

For example, the luminance value for each contrast area may be measured by an image analysis device. Likewise, the luminance score may be determined by the same image analysis device or any other device. The image analysis device or other device may be the processor 12 (FIG. 1) or another processor or device that is part of the system 10 shown in FIG. 1. For example, computer-readable instructions for analyzing images to measure luminance values and/or assign a corresponding luminance score for each image area may be stored in the storage device 14, such as the memory or another storage device.

As an example, if the measured luminance value of a particular area is 0-50, then the luminance score for that area may be 0.1 points. If the measured luminance value is 50-150, then the luminance score for that area may be 0.5 points. If the measured luminance value is 150-255, then the luminance score for that area may be 0.8 points.

Then, in step 906, a position score for each contrast area may be determined based on the position of each contrast area. For example, if the contrast area is positioned in a region known to be prone to gastritis, then the contrast area may be assigned a larger position score, whereas the position score may be lower if the contrast area is positioned in a region not known to be prone to gastritis or if the contrast area is in a region is known to be resistant to gastritis.

The position score for each area may be determined by an image analysis device or the processor 12 (FIG. 1) or another processor or device that is part of the system 10 shown in FIG. 1. For example, the processor may execute computer-readable instructions and/or algorithms for analyzing images to determine a position of each contrast area and/or assign a corresponding position score for each contrast area. The computer-readably instructions may be stored in the storage device 14, such as the memory or another storage device.

As an example, the position factor may be 0.1 points for an area not susceptible to gastritis, 0.5 points for an area known to have a small to moderate susceptibility of gastritis, and 0.8 points for an area susceptible to gastritis.

In step 908, an abnormality score for each area may be calculated based on the luminance score determined in step 904 and/or the position score determined in step 906. For example, the luminance score 904 for each area may be multiplied by the position score 906 for each area to calculate the abnormality score 908 for each area. As an example, for a certain area, if the measured luminance is 200, and the area is in a region susceptible to gastritis, then the abnormality score may be calculated as 0.64. That is, based on the above exemplary luminance value and position score ranges, the luminance score would be 0.8, and the position score would be 0.8, resulting in an abnormality score of 0.5×0.8, which is 0.64. In other words, the luminance score 904 of each area may be weighted based on its position 906.

The above luminance score ranges and position score ranges are merely exemplary, non-limiting ranges. The luminance score and position score ranges may be determined by the user or may be determined based on the reference and/or standard image and non-image data.

Then, in step 910, the overall abnormality score may be calculated as a total of the abnormality scores 908 for the areas. In other words, the weighted score (abnormality score 908) for each area may be combined to determine an overall contrast image abnormality score in step 910. For example, if the image was divided into 145 areas, and ten areas were determined to have an abnormality score of 0.4, forty areas were determined to have an abnormality score of 0.05, fifteen areas were determined to have an abnormality score of 0.08, zero areas were determined to have an abnormality score of 0.64, and eighty areas were determined to have an abnormality score of 0.01, the overall abnormality score may be calculated to be 8 (=(0.4×10)+(0.05×40)+(0.08×15)+(0.64×0)+(0.01×80)).

Alternatively, the luminance score may be the abnormality score, eliminating steps 906 and 908 in FIG. 22. In other words, the luminance score for each area determined in step 904 may be the abnormality score of each area such that the overall abnormality score may be calculated in step 910 as a total of the luminance scores for each area 904.

In any event, the overall abnormality score may be output 912 to the user, for example, via an output device 18, such as a display or a printer, or the overall abnormality score 910 may be output to a database or a server for storage. The overall abnormality score 910 may alternatively undergo additional processing in step 914 before being output to a user or server. Alternatively, a user may instruct the processor system 10 to perform additional processing 914 after output of the overall abnormality score 910.

Although the above description discloses calculating the abnormality score based on the subject abnormality image, the abnormality score could instead be calculated using the subject contrast image or any other image derived from the subject contrast image.

As discussed above with respect to FIG. 9, subject abnormality scores may be used to generate one or more visual representations to facilitate subject diagnosis. For example, one or more subject image abnormality scores and one or more subject non-image abnormality scores may be acquired and processed to generate a visual representation of the differences represented by the subject abnormality scores. Subject abnormality scores may be derived from dynamic data (e.g., video) or longitudinal data (e.g., data acquired at discrete points in time over a given period), and multiple visual representations corresponding to deviations at different points of time may be generated. The one or more visual representation may then be output to facilitate diagnosis of the subject in step. For abnormalities derived from dynamic or longitudinal data, multiple visual representations may be output simultaneously or sequentially.

Reference abnormality scores may be determined in the same manner for the reference abnormality images indicative of different severity levels of gastritis. After dividing the reference abnormality images or other reference images into specified areas, calculating the abnormality score for each area based on the luminance score and/or position score for each area, and calculating the overall reference abnormality score for each reference abnormality image, the reference abnormality scores may also be output to a server or database for storage, or may be output to a user. The reference abnormality scores may be calculated for several reference images representative of a particular severity level of gastritis to determine a reference abnormality score range or average for each severity level of gastritis. In other embodiments, a reference abnormality score or average score or range for each particular severity level may be determined from a composite reference image generated from multiple reference abnormality images representative of the particular severity level of gastritis.

As more subjects are diagnosed as having a particular severity level of gastritis using the system and methods disclosed herein, the reference image database and standard image database for subjects that are determined to be healthy may be continuously or periodically updated. Likewise, the reference abnormality score, average score, or score range for each severity level of gastritis may be continuously or periodically updated based on updated reference data.

Figure 23:
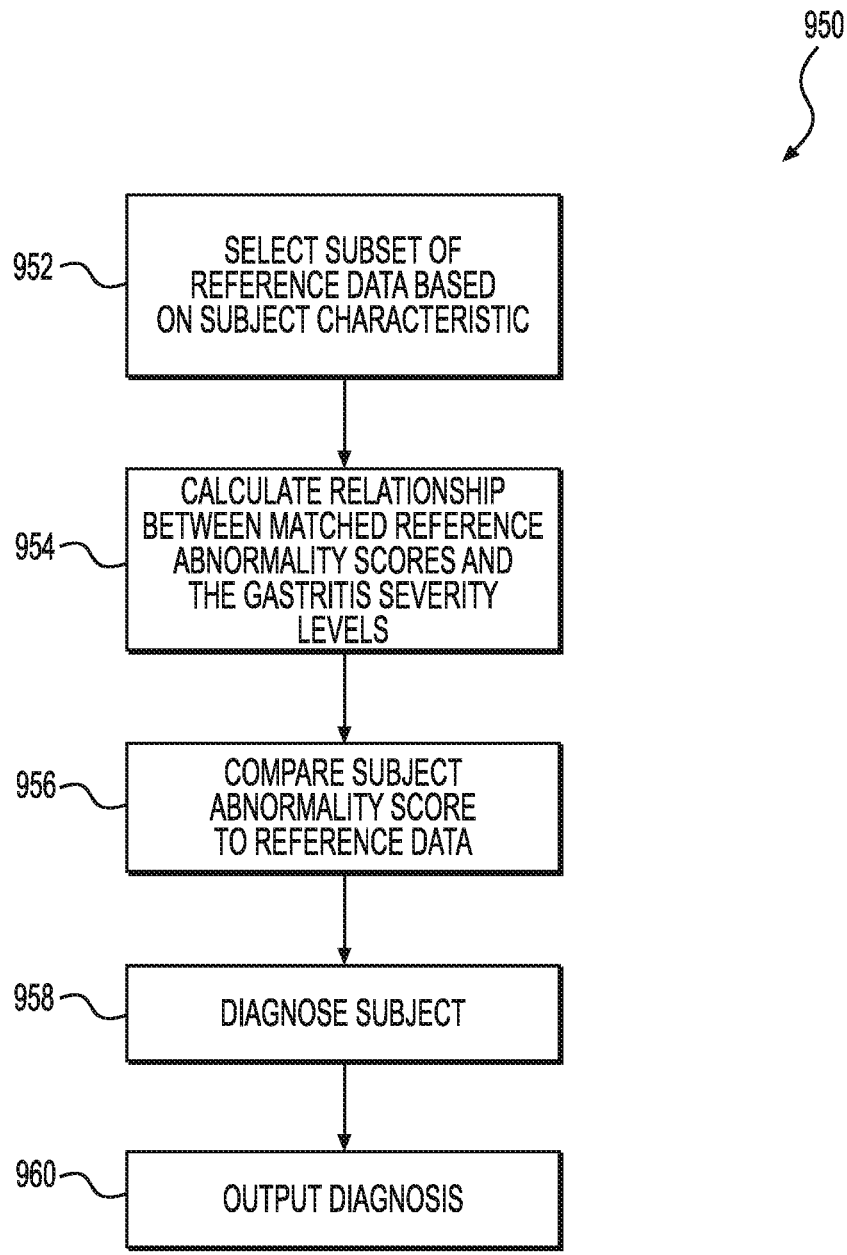
FIG. 23 is a flow chart of an exemplary method for diagnosing a severity of gastritis and/or possibility of gastric cancer based on the subject abnormality score.

The present embodiment may further include systems and methods for diagnosing a subject with a particular severity level of gastritis and/or diagnosing a likelihood of stomach cancer based at least in part of the abnormality score. An exemplary method 950 is shown in FIG. 23. In particular, the method 950 includes a step 952 of selecting a subset of reference data based on a subject characteristic, such as age, gender, or race, as discussed in more detail above. In step 954, a relationship is calculated between the abnormality scores and the gastritis severity level of the matched reference data (e.g., that share a characteristic with the subject).

As an example, the matched reference data may include: (i) 10,000 subjects with a score of 0-20 points, of which 100 have a large degree of gastritis, and 50 have stomach cancer, (ii) 2,000 subjects with a score of 20-40 points, of which 600 have a large degree of gastritis, and 300 have stomach cancer, and (iii) 500 subjects with a score of 40-60 points, of which 400 have a large degree of gastritis, and 200 have stomach cancer. In this case, it may be determined that a subject with a score of 0-20 points has low severity gastritis and a 0.5% possibility of stomach cancer, a subject with a score of 20-40 points has moderate severity gastritis and a 15% possibility of stomach cancer, and a subject with a score of 40-60 points has high severity gastritis, and a 40% possibility of stomach cancer.

For example, Table 2 shows an example correlation between the score and the likelihood of having a various severity levels of gastritis. For example, according to Table 2, if the subject has a score of 50, the probability of being normal is 10% (=200/2000), the probability of low degree gastritis is 20%, the probability of moderate degree gastritis is 30%, and the probability of high degree gastritis is 40%.

TABLE 2

| Score | Number | Normal | Low Degree | Moderate Degree | High Degree |
|---|---|---|---|---|---|
| 0-20 | 5000 | 3000 (60%) | 1500 (30%) | 450 (9%) | 50 (1%) |
| 20-40 | 3000 | 2000 (67%) | 500 (17%) | 400 (13%) | 100 (3%) |
| 40-60 | 2000 | 200 (10%) | 400 (20%) | 600 (30%) | 800 (40%) |

In step 956, the subject abnormality score is compared to the Reference data. Based at least in part on that comparison, the subject is then diagnosed in step 958 as having a particular severity of gastritis and/or the possibility of stomach cancer. For example, if the subject has an overall abnormality score of 8, then the subject may be diagnosed as having low severity gastritis and a 0.5% possibility of stomach cancer. The diagnosis may be output to a user, such as a doctor or technician via a display or printer or other output device 18, and/or the diagnosis may be output to a server or database in, for example, a storage device 14.

The exemplary diagnostic processor system 10 shown in FIG. 1 may be used to facilitate diagnosis of the severity level of gastritis of the subject and/or possibility of stomach cancer. For example, computer-readable instructions for analyzing and/or processing contrast images and data, generating abnormality images, calculating abnormality scores, performing or facilitating diagnosis of a particular severity level of gastritis and/or possibility of stomach cancer may be stored in the storage device 14, such as the memory. The processor 12 may execute the computer-readable instructions to facilitate diagnosis of the subject. As an output device 18, a display may be configured to display one or more of: the subject contrast image, the subject abnormality image, the standard contrast image, the reference contrast images, the reference abnormality images, non-image subject data, a subject abnormality score, and the diagnosis received from the processor.

Based on the diagnosis of the severity of gastritis, the subject may be appropriately treated. The processor may determine which treatment is appropriate based on the severity level of gastritis and output treatment information accordingly. For example, medications that block acid production and promote healing may be administered. Such medications including proton pump inhibitors, such as omeprazole, lansoprazole, rabeprazole, esomeprazle, dexlansoprazole, and pantoprazole. Proton pump inhibitors reduce acid by blocking the action of the parts of the cells that produce acid. Acid blockers or histamine (H-2) blockers may be administered to reduce the amount of acid released in the subject's digestive tract. Such acid blockers include ranitidine, famotidine, cimetidine, and nizatidine. Antacids may also be administered to neutralize exciting stomach acid and provide pain relief. Additionally, antibiotic medications may be administered to kill *H. pylori* in the subject's digestive tract. Such antibiotics may include clarithromycin, amoxicillin, and metronidazole. Further, stomach coating drugs, such as bismuth subsalicylate, that help protect the tissues that line the stomach and small intestine may be administered.

For example, in the treatment of acute gastritis (low degree gastritis), elimination of the cause is important. If the cause is clear, such as stress or drug use, it may be treated by removing the cause. If nausea and vomiting are severe, fasting, feeding by drip infusion, and treatment with gastric acid secretion inhibitors and gastric mucosal protective agents may indicated. If there is bleeding in the gastric mucosa, then use of a hemostat may be indicated.

In the case of chronic gastritis (moderate severity gastritis), the subject may be treated with a drug that suppresses gastric acid secretion. It may be used in combination with gastric mucous membrane protective drugs and stomach movement function improving drugs.

For atrophic gastritis (high severity gastritis), removal of *H. pylori* is indicated. In the eradication therapy, two types of antibacterial drugs and one type of proton pump inhibitor (a drug that suppresses the secretion of gastric acid) may be taken twice daily for 7 days. This therapy may be used to eliminate at least about 70% of bacteria. For remaining bacteria, the subject should be treated again with a different combination of antibacterial agents (secondary eradication therapy). This should eliminate about 90% of bacteria.

Diagnosing the Severity of Gastric Cancer

In an exemplary embodiment, the diagnostic system, method, and computer-readable storage medium are designed for determining or facilitating diagnosis of the severity of gastric cancer in a subject.

Figure 24:
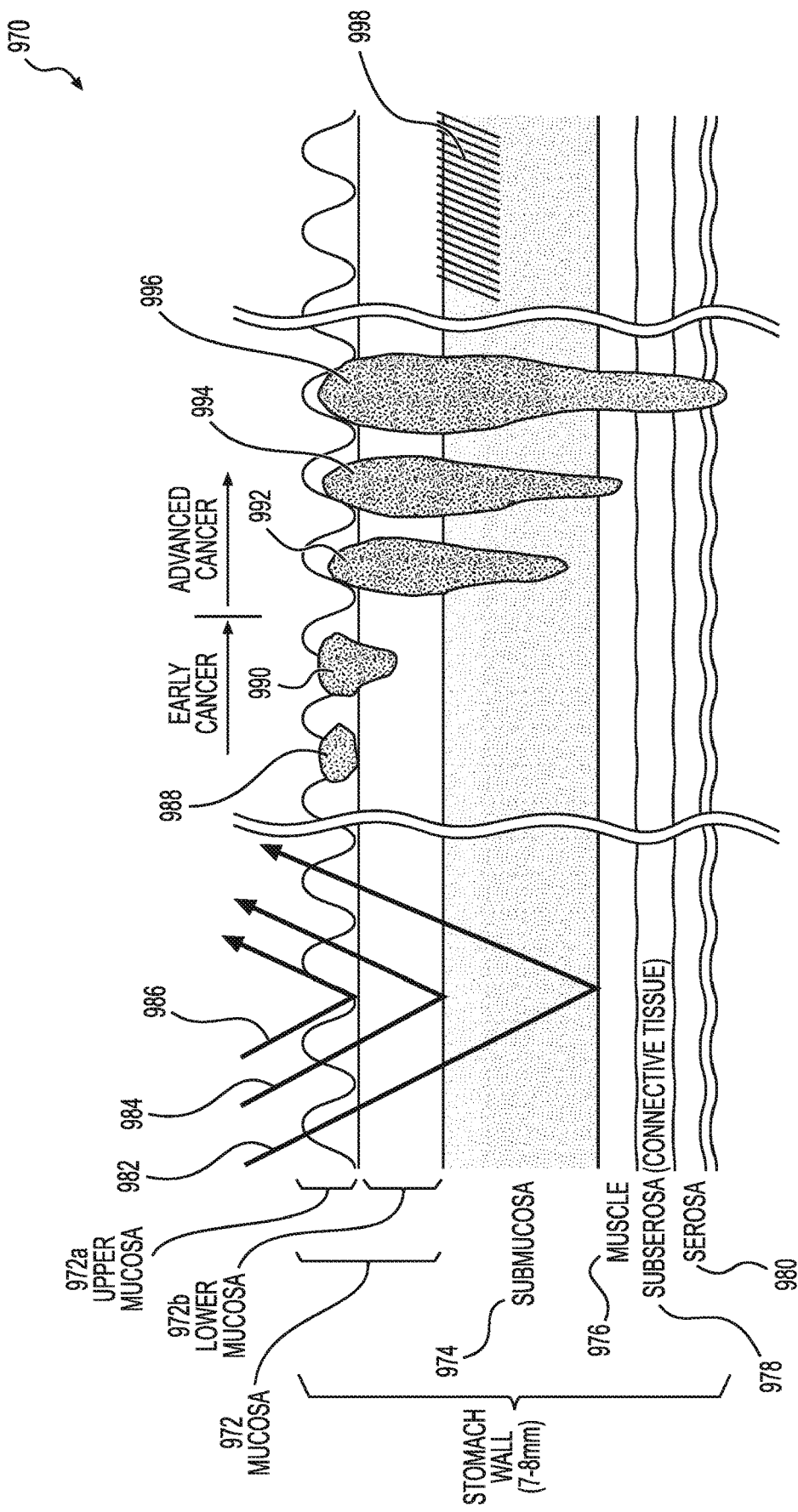
FIG. 24 is a schematic image of the layers of the stomach.

Gastric cancer is a disease in which malignant (cancer) cells form in the stomach wall. As shown in FIG. 24, the wall 970 of the stomach is made up of four layers of tissue. From the innermost layer to the outermost layer, the layers of the stomach wall are: mucosa 972, submucosa 974 (including upper 972a and lower 972b mucosa), muscle 976, and serosa 980, which includes subserosa (connective tissue) 978. Gastric cancer typically begins in the mucosa 972 and spreads through the outer layers as it grows. For instance, FIG. 24 shows various tumors 988, 990, 992, 994, 996 penetrating different layers of the stomach wall. However, some gastric cancers, such as Scirrhous stomach cancer, may have lesion(s) 998 that are present in the submucosal layer 974 or muscle layer 976, but are not present in the mucosal layer 972.

The severity of gastric cancer is generally expressed in stages of gastric cancer. The stage of gastric cancer is representative of the extent of the cancer in the body, and is usually determined based on the depth of gastric cancer in the stomach wall and the presence or absence of metastasis. Determining the severity or stage of gastric cancer is useful for determining how to treat the patient. Gastric cancer stages range from 0 to IV, with stage 0 being the earliest stage (least severe) stage IV being the most severe. In general, the lower the number, the less the cancer has spread. The staging system typically used for gastric cancer is the American Joint Committee on Cancer (ADCC) TNM system. The stage of gastric cancer is usually determined based on 3 important pieces of information: (1) the tumor invasion depth of the cancer into the layers of the stomach wall (see e.g., FIG. 24), (2) whether the cancer has spread to nearby lymph nodes, and (3) whether the cancer as metastasized to distant sites (e.g., distant lymph nodes or organs, such as the liver or lungs).

Gastric cancer is commonly detected and diagnosed by endoscopy in which an image of the stomach is created by capturing the reflected light when the tissue is illuminated by light. Physicians typically diagnose gastric cancer and/or a severity (e.g., stage) of gastric cancer based on structural changes (e.g., surface irregularities) of the surface of the stomach wall and changes in blood vessels by performing endoscopy to image the stomach wall. A physician may first confirm the unevenness and color of the surface by obtaining a white light endoscopic image of the patient's stomach wall. Then, the physician may confirm the blood vessel structure in the stomach wall by obtaining an endoscopic image using a narrower band of illumination light, e.g., by Narrow Band Imaging (NBI).

Gastric cancer diagnoses and stage determinations, however, are inherently subjective determinations by physicians. For example, diagnoses may vary depending on the experience and knowledge of the physician, resulting in inconsistent diagnoses. Additionally, diagnoses may be made based on incomplete information. For example, in white light images, the unevenness of the tissue surface can be visualized, but the organization (e.g., blood vessels) of the stomach wall cannot be visualized. On the other hand, images acquired with narrower wavelength bands can show tissue (e.g., blood vessels) within the layers of the stomach wall depending on the wavelength band of illumination light. However, the unevenness of the tissue surface cannot be visualized in NBI images. Thus, diagnoses based on only white light images or only NBI images may not be accurate or reliable. Further, it is difficult to determine the exact penetration depth of gastric cancer. Although NBI images use different wavelengths of light to penetrate and thus visualize different layers and tissues (e.g., blood vessels) within the stomach wall, the precise depth of the cancer cannot be determined because NBI images show, for example, blood vessels present not only at the depth at which the wavelength band of light can reach, but also show blood vessels present along the penetration route of the light and in the vicinity of the depth at which the wavelength band of light can reach. Thus, the exact depth of the cancer cannot be determined from NBI images.

Figure 26A:
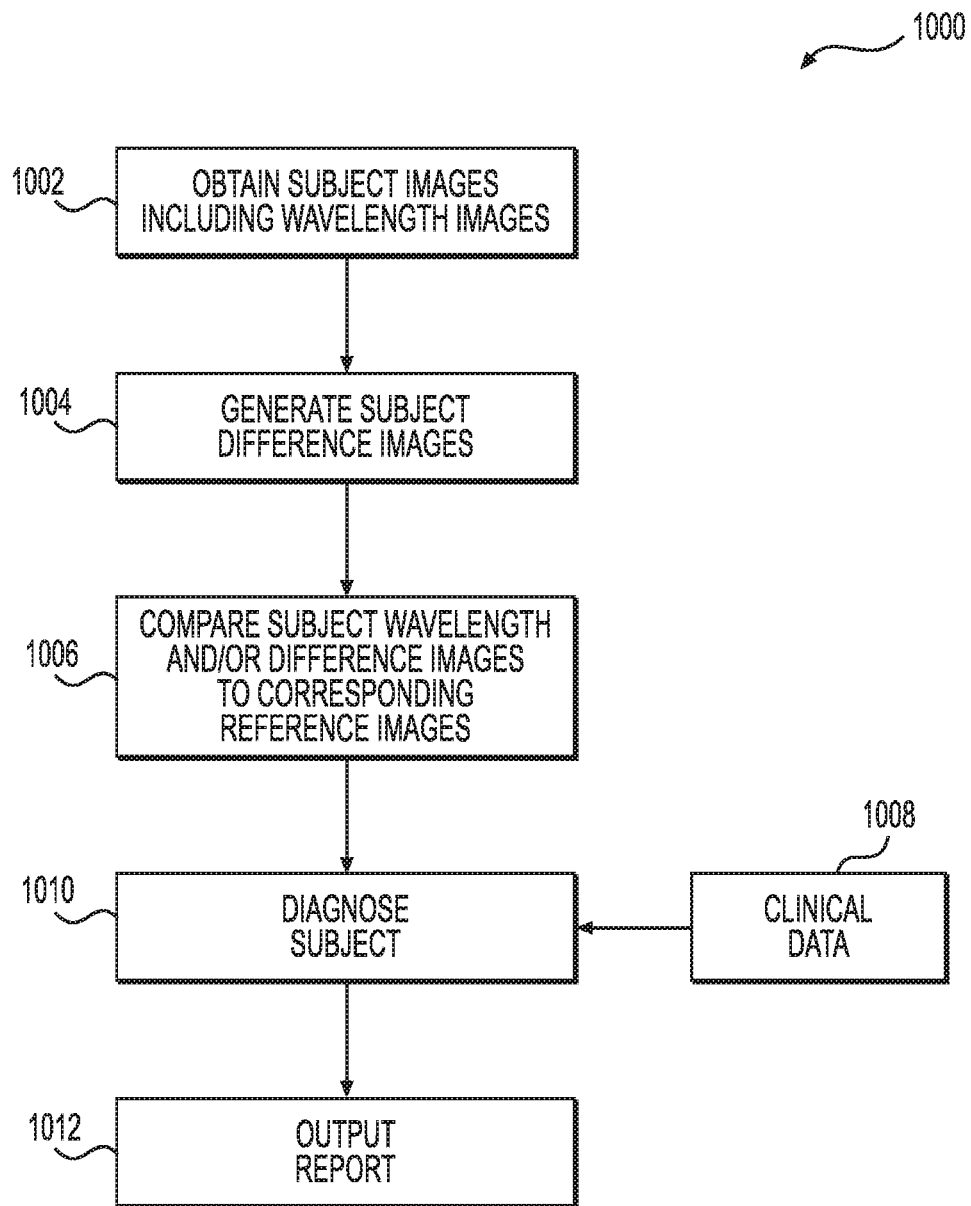
FIGS. 26A and 26B are flow charts of exemplary methods/algorithms for diagnosing a severity of gastric cancer.
Figure 26B:
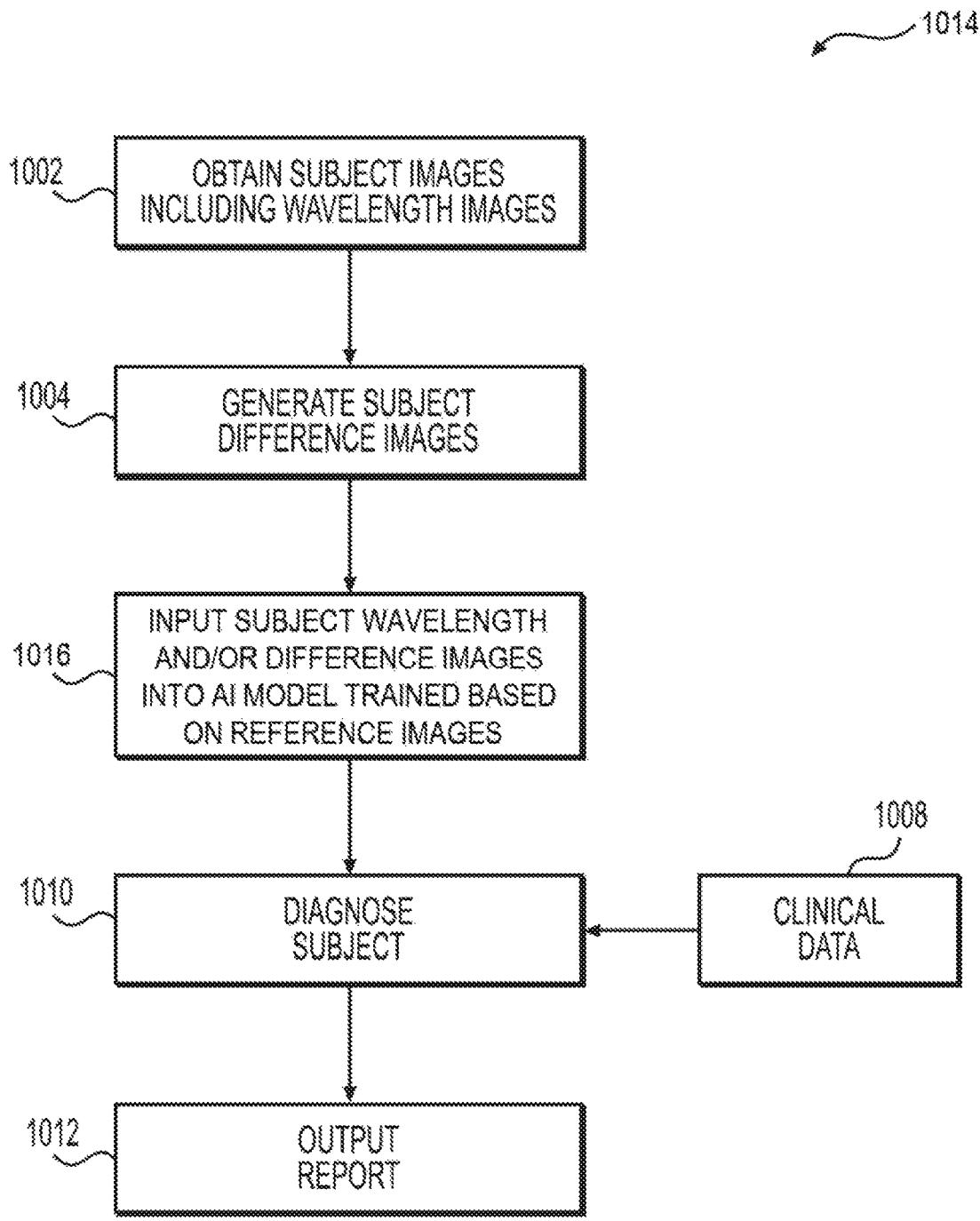

The present systems and methods are designed to improve the accuracy and consistency of gastric cancer diagnoses, and enable the exact depth of cancer to be determined. FIGS. 26A and 26B show exemplary algorithms/methods 1000, 1014 for diagnosing a subject with gastric cancer and a particular severity (e.g. stage) thereof according the present disclosure. The method 1000 of FIG. 26A includes a first step 1002 of capturing endoscopic images of a subject's stomach including images of different wavelength bands to visualize different layers and tissues within the stomach wall. Difference images are then generated from the subject images in step 1004 for improved visualization of particular layers and/or tissues within the stomach wall. In the method 1000 of FIG. 26A, the subject images are then compared to corresponding reference images representative of particular severities (e.g., stages) of gastric cancer to identify reference images with similar feature patterns in step 1006. Multiple subject images, including difference images, may be compared with corresponding reference images to determine the severity or degree of cancer present in each layer of the stomach wall and the precise penetration depth of cancer. The determinations of the severity of cancer present in each layer of the stomach wall can then be compiled and analyzed for facilitating an accurate diagnosis of an overall severity level (e.g., stage) of gastric cancer in step 1010. The diagnosis may be made based not only on the comparison in step 1006 but also on clinical data 1008. A report of the diagnosis may be output by the system in step 1012.

FIG. 26B shows another method/algorithm 1014 for diagnosing gastric cancer and a severity level (e.g., stage) thereof in a subject. The method/algorithm 1014 of FIG. 26B is substantially the same as the method/algorithm 1000 in FIG. 26A except that step 1016 is performed instead of step 1006. Therefore, subject images are obtained in step 1002, and difference images are generated in step 1004. But instead of comparing the subject images to reference images indicative of a particular severity (e.g., stage) of gastric cancer, the subject images, including the wavelength and difference images, are input into an Artificial Intelligence (AI) model that has been trained based on the reference images to diagnose the subject with gastric cancer and a stage thereof. The subject can then be diagnosed in step 1010, and a report may be output in step 1012. The diagnosis may be made based not only on the out of the learned model but also other clinical data 1008.

In both methods 1000, 1014, the first step 1002 involves acquiring an endoscopic image of a subject's stomach by capturing the reflected light when the tissue is illuminated by light. Images of different tissue (e.g., blood vessels) and/or layers of the stomach wall can be obtained by using light of different wavelength bands because a depth of light penetrating tissue varies according to a wavelength of the light. For example, as illustrated in FIG. 24, blue 986, green 984, or infrared light 982 light penetrates different layers of the stomach wall, and thus, an image of the mucosa 972, submucosa 974, and muscle 976 may be obtained according to a wavelength band of the illumination light.

The degree to which light is scattered by living tissue can also vary depending on the wavelength band of light. The refractive index of the tissue can also affect the degree to which light is scattered by the living tissue. In particular, in the case of light with a short wavelength band, such as blue light 986, the light only reaches around the surface layer due to the absorption properties and scattering properties at the living body tissue, being subjected to absorption and scattering within the range up to that depth, so light coming out from the surface is observed. In the case of green light 984 with a wavelength band longer than that of blue light 986, the light reaches a depth deeper than the range where the blue light 986 reaches, is subjected to absorption and scattering within the range at that depth, and light coming out from the surface is observed. Further, red light with a wavelength band longer than that of green light 984, reaches a range even deeper. Infrared (IR) light 982 with an even longer wavelength band reaches a range even deeper.

Although not illustrated in FIG. 24, various other wavelength bands of light, such as red, violet, ultraviolet light, blue-green, violet-blue, white, and the like can be used for penetrating different layers of the stomach and/or imaging different tissue and/or structures (e.g., blood vessels and lesions) within the layers. As used herein, "wavelength image" refers to an image obtained by a particular wavelength band of light, including, but not limited to, ultraviolet, violet, violet-blue, blue, blue-green, green, red, near-infrared, infrared, and white light images.

The wavelength images may be acquired by controlling the wavelength band of the light illuminated during imaging to be a desired wavelength band. As one example, a narrow-band imaging (NBI) endoscope can be used to obtain the wavelength images. An NBI endoscope can separate visible light of a wide band into, for example, blue, green, or red light of narrow bands using a rotary filter wheel. The separated narrow band light is sequentially or selectively illuminated onto a particular part of the stomach to obtain an image. Wavelength images may include images obtained with white, violet, violet-blue, blue, blue-green, green, red, ultraviolet, infrared, and near-infrared light. The wavelength images may be obtained by illuminating light of a particular wavelength band and capturing the reflected light. Alternatively, wavelength images (of a narrower wavelength band than white light) can be obtained from white light images by decomposing the images into wavelength components, and synthesizing images of desired wavelength bands. An arbitrary spectral image may be extracted from an image acquired with white light (400 to 700 nm) as in Flexible Spectral Imaging Color Enhancement (FICE) to obtain a narrow wavelength band image.

A lamp may be used as the light source to illuminate light having a particular wavelength band, or a laser may be used as the light source. In the former case, the lamp light of a particular wavelength band reaches a depth having a width in the depth direction of the stomach wall. In the latter case, the wavelength band of the laser is very narrow. Therefore, the depth to which the laser reaches does not have a width. As such, it is possible to determine whether or not the cancer has reached a specific depth (e.g., 1 mm in depth, 2 mm in depth, etc. . . . ) by using a laser. For example, ultraviolet light can be used to detect/diagnose very early cancers occurring in the surface layer of the mucosal layer. Near-infrared light can also be used to detect and diagnose cancers that develop in the muscularis (deeper layers of the stomach wall). Table 3 shows the invasion depth of exemplary lamp and laser lights of various wavelength bands.

TABLE 3

| Light source | | Name | Wavelength band | Invasion depth |
|---|---|---|---|---|
| Lamp | | White | 340-700 nm | Muscular layer |
| | | Purple color | 265-310 nm | Mucosal layer |
| | | Blue | 390-445 nm | Mucosal layer |
| | | Green | 530-550 nm | Submucosal layer |
| | | Infrared | 790-820 nm, 905-970 nm | Muscular layer |
| Laser | Solid state | Ho:YAG | 206 nm | Mucosal layer |
| | | Er:YAG | 294 nm | Mucosal layer |
| | | Ruby | 694 nm | Muscular layer |
| | | Nd: glass | 1060 nm | Muscular layer |
| | | Nd:YAG | 1061 nm | Muscular layer |
| | Gas state | Excimer | 193-353 nm | Mucosal layer |
| | | He-Cd | 325 nm (442 nm) | Mucosal layer |
| | | Ne | 332 nm | Mucosal layer |
| | | N2 | 337 nm | Mucosal layer |
| | | Xe | 460-627 nm | Submucosal layer |
| | | Ar+ | 458-515 nm | Submucosal layer |
| | | Kr | 472-647 nm | Submucosal layer |
| | | Cu | 500 nm | Submucosal layer |
| | | CO | 530 nm | Submucosal layer |
| | | He-Ne | 633 nm (1150 nm, 3390 nm) | Submucosal layer |
| | | CO2 | 928 nm (962 nm, 1060 nm) | Muscular layer |
| | Semi-conductor | InGaN | 450 nm | Mucosal layer |
| | | ZnCdSe | 489 nm | Mucosal layer |
| | | ZnTeSe | 512 nm | Submucosal layer |
| | | GaP | 555 nm | Submucosal layer |
| | | AGaInP | 570 nm | Submucosal layer |
| | | InGaN | 590 nm | Submucosal layer |
| | | AlGaAs | 660 nm | Muscular layer |
| | | GaP(Zn-0) | 700 nm | Muscular layer |
| | | GaAs(Si) | 980 nm | Muscular layer |
| | | InGaAsP | 1300 nm | Serosa |

White light images can be used to visualize unevenness of the stomach wall surface and the color of the stomach wall surface (e.g., redness). Light (e.g., from a lamp or laser) of a narrower wavelength band can be illuminated to visualize specific layers of the stomach or specific tissues within the stomach wall layers. For instance, FIG. 24 shows penetration of various layers of the stomach wall by exemplary wavelength bands of light, e.g., blue 986, green 984, and infrared 982 lights. Blue light (e.g., wavelength band of 390-445 nm) reaches the mucosal layer 972, and green light (e.g., wavelength band of 530-550 nm) reaches the submucosal layer 974. Various images showing different layers of the stomach can be acquired by changing the wavelength band of light. Additionally, different wavelength bands of light absorb/reflect different tissues. Therefore, the structure that can be observed also differs depending on the wavelength band. For example, white light (e.g., wavelength band of 340-700 nm) is absorbed/reflected by hemoglobin. Blue light (e.g., wavelength band of 390-445 nm) delineates blood vessels containing hemoglobin.

Images acquired with violet light (e.g., wavelength band of 265-310 nm) can provide vascular image information of the surface layer of the mucosal layer. Images acquired with blue light (e.g., wavelength band of 390-445 nm) can provide information on the vascular image of the mucosal layer. Images acquired with green light (e.g., wavelength band of 530-550 nm) can provide information on the blood vessel image of the submucosa. An image obtained by near-infrared light (e.g., a wavelength band of 905 to 970 nm) can provide information on a blood vessel image of a muscular layer.

Lesion or tumor areas may be identified from the microvascular pattern. Gastric cancer builds up blood vessels to share nutrients with cancer cells. Therefore, gastric cancer, including early gastric cancer, may be detected and diagnosed by analyzing the microvascular pattern and microsurface structures of the superficial mucosa. For instance, a lesion area can be determined as an area in which blood vessels are densely present. A regular microvascular pattern may be one in which in which the mucosal capillaries have a uniform shape that can be closed-loop (polygonal) or open-loop, and a consistent size, and their arrangement and distribution are regular and symmetrical. An irregular microvascular pattern, on the other hand, may be one in which the vessels differ in shape, are closed-loop (polygonal), open-loop, tortuous, branched, bizarrely shaped, with or without a network. In an irregular microvascular pattern, the size of the vessels may also vary and their arrangement and distribution may be irregular and asymmetrical. For instance, an irregular microvascular pattern may be defined by the presence of thin spiral blood vessels within the fine lobular superficial structure, or the presence of vertical spiral blood vessels within the coarse lobular superficial structure. Other irregular microvascular patterns may include fine networks including fine tubular structures surrounded by thin microvasculature or corkscrew patterns, which appear as obliterated surface structures and irregular vascular patterns without loop formation. A microvascular pattern may be absent when the subepithelial microvascular pattern is obscured by the presence of an opaque substance, for example, white opaque substance, within the superficial part of the mucosa. An irregular or absent microvascular pattern may be indicative of gastric cancer.

In step 1004 of FIGS. 26A and 26B, difference images can be generated to visualize particular layers of the stomach wall, and/or particular tissues or structures (e.g., blood vessels, lesions) within the layers. As used herein, "difference image(s)" refers to subtraction images, addition images, and combinations thereof. For example, a difference image may be generated by comparing or adding a first image and a second image. One or both of the first and second images may be wavelength images of different wavelength bands of light, or may be difference images. For example, a difference image may be generated by subtracting a second wavelength image of a second wavelength band of light from a first wavelength image of a first wavelength band of light, longer than the second wavelength band, or a difference image may be generated by subtracting a wavelength image of a specific wavelength band of light from a previously generated difference image. A difference image may also include addition images obtained by adding a first image to a second image. One or both of the first and second images may be wavelength images of different wavelength bands of light, or may be difference images. Additionally, a difference image may include an addition/subtraction image obtained by adding a first image to a second image and subtracting a third image from the addition image. For example, such a difference image may obtained by adding a first wavelength image to a second wavelength image (e.g., white light image) and subtracting a second wavelength image from the addition image. Different layers or combinations of layers can be visualized by changing the images being subtracted and/or added.

Table 4 below shows exemplary wavelength bands of the first and second wavelength images for acquiring images of specific stomach layers. Although Table 4 only shows exemplary stomach layers images by obtaining subtraction-type difference images, addition images in which a first image and a second image of a different wavelength band are added together, as well as an addition/subtraction image in which a first wavelength image is added to a second wavelength image (e.g., a white light image), and then a third wavelength image is subtracted, can also be obtained for facilitating accurate diagnosis of gastric cancer severity.

TABLE 4

| Stomach Layer Visualized in Difference Image | First Image (wavelength) | Second Image* (wavelength) |
|---|---|---|
| Upper Mucosa 972a | Blue (440-460 nm) | None |
| Mucosa 972 (upper 972a and lower 972b) | Green (530-550 nm) | None |
| Lower Mucosa 972b | | Blue (440-460 nm) |
| Mucosa 972, Submucosa 974, and muscle layer 976 | Infrared (940 nm) | None |
| Lower Mucosa 972b, Submucosa 974, and muscle layer 976 | | Blue (440-460 nm) |
| Submucosa 974, and muscle layer 976 | | Green (530-550 nm) |
| Mucosa 972 (upper 972a and lower 972b), Submucosa 974, and upper part of muscle layer 976 | White (340-700 nm) | None |
| Upper part of muscle layer 976 | | Blue (440-460 nm) |
| Submucosa 974, and upper part of muscle layer 976 | | Green (530-550 nm) |

*The Second Image is subtracted from the First Image to create the Difference Image.

The subject images include wavelength, white light, difference, addition, and addition/difference images. For example, the subject images may include one or more of the following types of images: (1) wavelength images obtained using lamp or laser light source including (a) a white light image with information on the surface irregularities and color of the stomach wall, (b) a narrower wavelength band image with information on tissue(s) and/or structure(s) in the various stomach wall layers, and (2) a difference image obtained by: (a) subtracting a second wavelength image of a second wavelength band from a first wavelength image of a first wavelength band (e.g., the first wavelength image may be a white light image or a narrower wavelength band image), (b) an addition image obtained by adding a first wavelength image to a second wavelength light image (e.g., the first or second wavelength images may be a white light image or a narrower wavelength band image), or (c) an addition/subtraction image obtained by adding a first wavelength image to a second wavelength light image and subtracting a third wavelength image from the addition image (e.g., the first or second wavelength images may be a white light image or a narrower wavelength band image). The images may include those acquired with lamp light of a particular wavelength band and those acquired with a laser of a narrower wavelength band. The more subject images obtained and compared to reference images, the more accurate the diagnosis of the severity (e.g., stage) of gastric cancer.

In step 1006 of method 1000 of FIG. 26A, the subject images, including the wavelength and difference images, are compared to reference image indicative of a particular severity level (e.g., stage) of gastric cancer. The reference images also include images representative of a normal or healthy stomach that does not have gastric cancer. The subject images are compared with corresponding reference wavelength and/or difference images to identify to identify reference images with similar feature patterns. The feature patterns may include microvascular patterns and the size and depth of lesions. The subject images are compared to corresponding reference images to diagnose the subject with a particular severity level (e.g., stage) of gastric cancer. For example, a blue wavelength subject image is compared with a blue wavelength reference image in the database, or a subject difference image of green wavelength and blue wavelength subject images is compared with a reference difference image of green wavelength and blue wavelength reference images. Accuracy can be improved by acquiring multiple images of the subject showing various stomach layers and tissues, and comparing each of those images with corresponding reference images in the database. For example, by acquiring multiple images, the different layers and tissues in the stomach wall can be individually examined to determine the extent or degree of gastric cancer for each stomach wall layer. This facilitates determining a depth of the cancer in the stomach wall for making an accurate diagnosis. An overall diagnosis of the severity (e.g., stage) of gastric cancer can be made based on the individual determinations for each stomach wall layer.

The use of multiple images including images of a particular wavelength band ("wavelength images") and difference images provides significantly improved visualization of the various layers of the stomach wall, as well as various tissues and structures within the stomach wall layers, enabling the location, size (e.g., lateral extent), and invasion depth of a tumor or lesion to be readily determined. The difference images enable feature patterns corresponding to the severity of gastric cancer, such as a malformation, lesion, tumor, and/or microvascular pattern, including thickness and branching of blood vessels, the occupation rate, and the number of blood vessels per area, to be clearly visualized. A topography and color (e.g., redness) of the stomach wall surface can also be observed when one of the wavelength images is a white light image. Additionally, by processing and comparing the images as discussed herein, lesions or tumors can be identified and analyzed to make accurate and consistent diagnoses of the severity and/or stage of gastric cancer. For instance, by comparing subject images to reference images indicative of various stages of gastric cancer, feature patterns, such as lesions, tumors, and irregular microvascular patterns, can be more reliably detected. Accuracy and consistency of diagnoses can further increase as the databases of reference images increases.

By acquiring a plurality of images of the subject's stomach, including wavelength and difference images, each layer of the subject's stomach and the surface topography and color can be visualized. Feature patterns can be extracted from the images to determine how far into the stomach layers the cancer has spread. For example, how far the cancer has penetrated into each of the stomach layers can be determined by acquiring images of the upper layers 972a and lower layers 972b of the mucosa 972, and the submucosa 974, individually, and determining the extent or severity of gastric cancer in each layer. Then, the determinations for each layer can be compiled and analyzed to make an overall diagnosis of the severity (e.g., stage) of gastric cancer. Lesion(s) 998 that are present in the submucosal layer 974 or muscle layer 976, but are not present in the mucosal layer 972, which are indicative of Scirrhous stomach cancer, may be identified by acquiring and visualizing multiple images (including wavelength and difference images). For example, a difference image of an infrared (first) wavelength image and a green (second) wavelength image would allow visualization of the submucosa 974, and a green wavelength image would allow visualization of the mucosa 972. If feature patterns of cancer are present in the submucosa 974 but not in the mucosa 972, then the subject could be diagnosed with Scirrhous stomach cancer 998.

The comparison in step 1006 is then used to make a diagnosis in step 1010. The diagnosis 1010 may also be made by taking other data and analysis 1008 into consideration, including non-image data, such as family history, clinical data, laboratory data, subject history, family history, subject vital signs, results of various tests (e.g., genetic tests), and any other relevant non-image data. Numerous subject and reference data and images may be created and compared. Then, a report of the diagnosis is output in step 1012, for example, to an output device 18 (shown in FIG. 1), such as a display or a printer, or to a database or server for storage, or to a user in a human-readable format.

In the method 1014 of FIG. 26B, the subject images, including the wavelength and difference images, are input into an AI model that has been trained based on the reference images to diagnose the subject with gastric cancer and a stage thereof instead of comparing the subject images to reference images indicative of a particular severity (e.g., stage) of gastric cancer. For example, the AI model may be a deep learning model, such as convolutional neural network. The reference images are labeled as representing a healthy stomach free of gastric cancer, or labeled as representing a stomach having a particular severity (e.g., stage) of gastric cancer. The gastric cancer diagnosis and severity (e.g., stage) assigned to each of the reference images may be based on the results of diagnostic imaging or tissue diagnosis. Severity labeling may begin with imaging or histological diagnosis by a doctor and metastasis to lymphatic vessels or other organs by CT and/or MRI. During training, e.g., supervised learning, the model learns feature patterns corresponding to gastric cancer and a severity thereof from the reference images collected in the database. The model may be trained via a pattern recognition algorithm to extract and learn the feature patterns corresponding to healthy and various severity levels (e.g., stages) of gastric cancer. For example, such feature patterns may include microvascular patterns, such as blood vessels and feature points based on the thickness, branching, and position of bloods vessels and the number of blood vessels per area, occupation rate, topography (e.g., unevenness) of surface of stomach wall and color (e.g., redness), and malformations.

The system may perform data analytics to determine meaningful patterns in image and non-image data and build models based on these determined patterns, which can be used to automatically analyze images and other medical data. For example, after developing a model using training data, the system may update the model based on feedback designating a correctness of the training information or a portion thereof. For example, the system may update a model based on clinical results associated with one or more images included in the training information. In some embodiments, a user may manually indicate whether diagnostic information included in the training information was correct as compared to an additional (e.g., later established) diagnosis).

Figure 29:
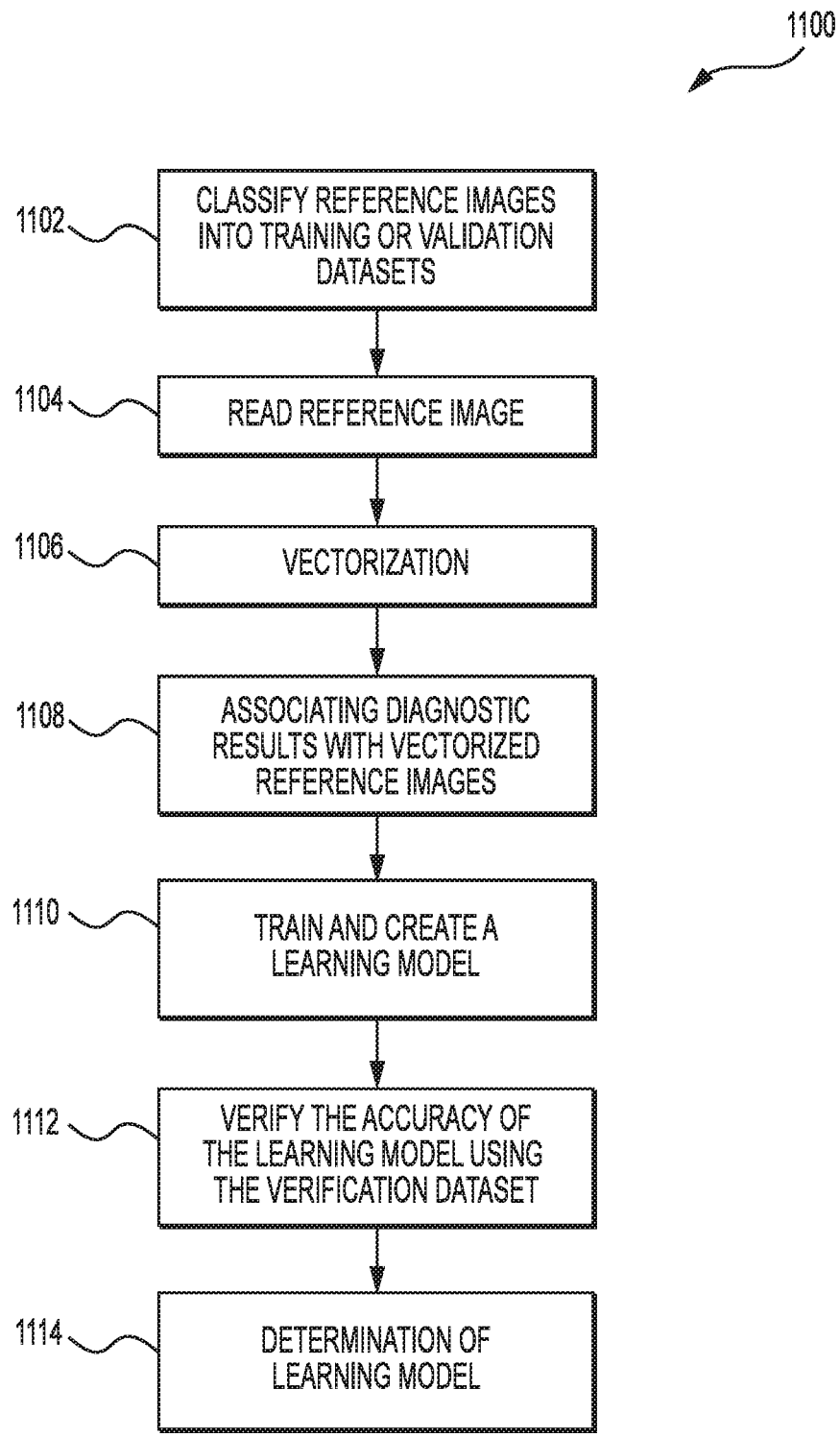
FIG. 29 shows an exemplary method/algorithm for preparing (e.g., processing) the reference images and training an artificial intelligence (AI) model using the reference images.

FIG. 29 shows an exemplary method/algorithm 1100 for preparing (e.g., processing) the reference images and training the model using the reference images. The reference images and associated diagnostic results (presence or absence of stomach cancer and severity (stage)) are collected and stored in a database. First, the reference images are randomly classified into two groups in step 1102. The first group is the learning data set, which classifies about two thirds of the total data. The second group is a data set for validation (e.g., verification), and approximately one third of all data is classified. Then in step 1104, the images are read and images belonging to the following exclusion criteria are excluded. Excluded images include subjects with severe gastritis, gastric ulcers or lesions adjacent to ulcers, poor quality images, bleeding, halation, blurring, and defocus. After exclusion, images of approximately 800 patients are used. The learning data set uses about 8,000 images. The images are stored in JPEG form and used for training. The reference images can be rotated, expanded/reduced, moved, or distorted to increase the number of pieces of data that can be used to train the AI model.

The reference images are then vectorized in step 1106. Specifically, a white image and a difference image are vectorized, respectively, and the vectorized white image and the difference image are integrated into one piece of data. Next, the diagnosis result (presence or absence of gastric cancer and severity (stage)) is associated with the vectorized reference image in step 1108. Vectorization and related of diagnostic results are performed for all reference images. The vectorization of images may be performed by algorithm, such as Potrace. The algorithm is basically vectorized by 1) extraction of contour coordinates, 2) polygonization, and 3) approximation with a Bezier curve.

Then in step 1110, the learned model is then trained using the first group of data (e.g., training dataset). When creating the learned model, the number of nodes is appropriately changed in accordance with the output accuracy of the learned model to create the learned model. Thereafter, in step 1112, the reference images classified into the second group (e.g., validation dataset) are input to the learned model, and a diagnosis result is output. The matching rate between the result output by the learned model and the diagnostic result associated with the reference image is calculated to determine the accuracy of the learning model.

Further, the first group and the second group create a plurality of learned models by changing the combination of reference images. In step 1114, the learned model with the highest precision is selected among the plurality of learned models created and used to analyze the subject images in the methods and systems disclosed herein for diagnosing a severity (e.g., stage) of gastric cancer.

The learned model with the highest precision is employed in the systems and methods disclosed herein. When a subject image is input into the learned model, the learned model can identify the presence and severity of gastric cancer from the subject image based on the learned feature patterns from training on the plurality of reference images in the database. The learned model extracts features from the subject images and outputs a severity (e.g., stage) diagnosis based on the feature patterns. Accuracy and consistency of diagnoses can be improved by the use of AI to extract feature patterns related to the severity of gastric cancer using a model trained with multiple reference images. Additionally, accuracy is improved when multiple subject images (e.g., including various white light, narrower wavelength, and difference images) such that the learned model can identify the severity of cancer present in each layer of the stomach wall to determine a penetration depth of gastric cancer in the stomach wall and diagnose a stage of gastric cancer.

In addition to subject images, the learned model may also receive non-image data for analysis and may diagnose the subject as having gastric cancer and/or a severity or stage thereof based on both the image and non-image data. For example, the subject's images and medical record information may be input into the system. The system can diagnose gastric cancer based on learned information and the images using the model. The system may identify the severity (e.g., stage) of gastric cancer based on the above diagnosis and medical record information (e.g., presence or absence of cancer metastasis). The system may output to a user a diagnosis of the presence or absence of gastric cancer and the stage of gastric cancer. As more and more subjects are diagnosed with various severity levels and stages of gastric cancer, the system may update its models accordingly. For example, the learned model may be designed to adjust itself in response to new data and conditions. For example, the model may be retained with new subject images after they are diagnosed as showing a particular severity level (e.g., stage) of gastric cancer.

The learned AI model can then output a diagnosis in step 1010 based on the subject images. The diagnosis may also be made by taking other data and analysis 1008 into consideration, including non-image data, such as family history, clinical data, laboratory data, subject history, family history, subject vital signs, results of various tests (e.g., genetic tests), and any other relevant non-image data. Numerous subject and reference data and images may be created and compared. Then, in step 1012, a report of the diagnosis is output, for example, to an output device 18 (shown in FIG. 1), such as a display or a printer, or to a database or server for storage, or to a user in a human-readable format.

The various images and data described herein may be stored in one or more databases to facilitate subsequent data analysis. Moreover, any or all of the comparisons may be performed either automatically by a data processing system, such as system 10, or by a medical professional, such as a doctor, or by some combination thereof, to facilitate automatic or manual diagnosis of the subject.

The present embodiments may use a database of reference/training images (including wavelength and difference images) indicative of various severity levels (e.g., stages) of gastric cancer, and normal (healthy) stomach walls that do not have gastric cancer. The reference images may be images collected from past patients, preferably of various ages, genders, and ethnicities. The database is constructed to include reference image data including wavelength images acquired at different wavelength bands (including white light images) and difference images. The diagnosis result is associated with each reference image and other data in the database. Accuracy and consistency of diagnoses increase as the number of reference images, as well as reference severity information, in the database increases. The database may be stored on a server, in one or more memory or storage devices, and/or in other suitable media. Such databases may be continuously or periodically updated as more subjects are diagnosed with a particular stage of gastric cancer.

Figure 25:
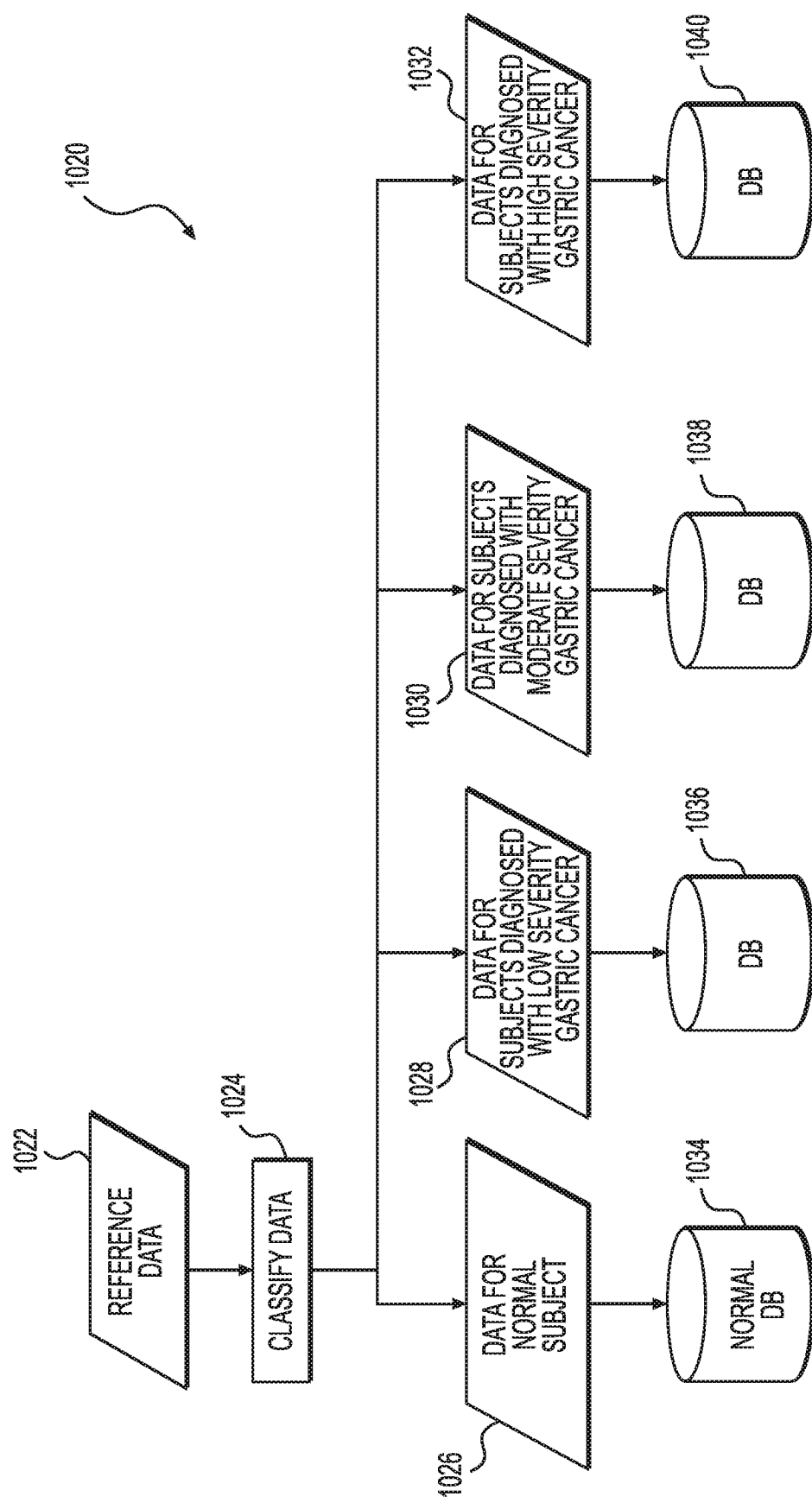
FIG. 25 is a flow chart of an exemplary method for categorizing reference and standard data to facilitate diagnosis of a severity level and/or stage of gastric cancer.

Additionally, reference image data may be categorized and sorted into standardized databases, such as through an exemplary method 1020 shown in FIG. 25. The method 1020 may include acquiring reference data 1022, which may include image and non-image data from various people, and categorizing the data in step 1024. For example, the reference data 1022 may be categorized into various groups, such as normal (healthy) subject data 1026, data 1028 of subjects clinically diagnosed with low severity gastric cancer, data 1030 of subjects diagnosed with moderate severity gastric cancer, and data 1032 of subjects diagnosed with high severity gastric cancer. The data 1026, 1028, 1030, and 1032 may be stored in respective databases 1034, 1036, 1038, and 1040. Such databases may be stored on a server, in one or more memory or storage devices, and/or in other suitable media. Such databases may be continuously or periodically updated as more subjects are diagnosed.

Each database for normal 1034, low severity 1036, moderate severity 1038, and high severity 1040 gastric cancer may include one or more of the following types of reference images: (1) wavelength images obtained using a lamp or laser light source including (a) a white light image with information on the surface irregularities and color of the stomach wall, (b) a narrower wavelength band image with information on tissue(s) and/or structure(s) in the various stomach wall layers, and (2) a difference image obtained by: (a) subtracting a second wavelength image of a second wavelength band from a first wavelength image of a first wavelength band (e.g., the first wavelength image may be a white light image or a narrower wavelength band image), (b) an addition image obtained by adding a first wavelength image to a second wavelength light image (e.g., the first or second wavelength images may be a white light image or a narrower wavelength band image), or (c) an addition/subtraction image obtained by adding a first wavelength image to a second wavelength light image and subtracting a third wavelength image from the addition image (e.g., the first or second wavelength images may be a white light image or a narrower wavelength band image). The images may include those acquired with lamp light of a particular wavelength band and those acquired with a laser of a narrower wavelength band. Multiple images (e.g., multiple different wavelength images, which are used to produce multiple different difference images) may be stored for each stage of gastric cancer, each layer of the stomach wall, and/or each tissue within the stomach wall. The reference images are accumulated in a database together with the respective stage of gastric cancer or may be identified as "normal" or "healthy" for images of stomachs that do not have gastric cancer. The data 1026, 1028, 1030, and 1032 in each database 1034, 1036, 1038, and 1040 may be further standardized and classified according to various subject characteristics, such as age, gender, and race, or type of image, such as white light images, blue wavelength images, purple wavelength images, red wavelength images, green wavelength images, ultraviolet wavelength images, infrared wavelength images, near-infrared wavelength images, and difference images generated from various wavelength images.

Figure 27A:
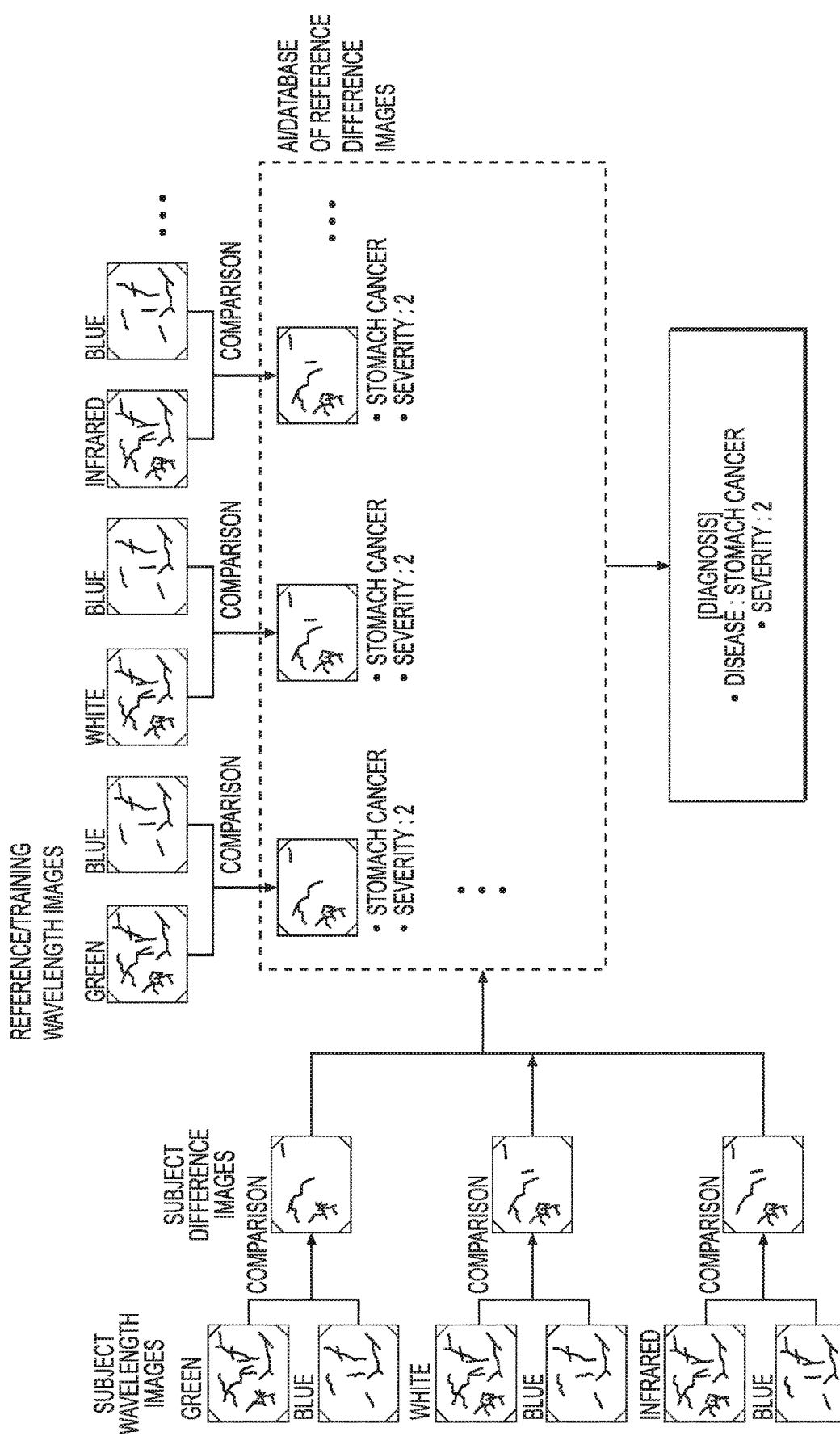
FIGS. 27A-27C show exemplary methods for comparing subject images with reference images to diagnose a severity of gastric cancer.

An exemplary embodiment is shown in FIG. 27A, in which a subject is diagnosed with severity 2 gastric cancer (which may correspond to stage II gastric cancer). One or more wavelength images of the subject are acquired and difference images are generated for the purpose of visualizing different stomach layers. The wavelength images and/or difference images are compared with corresponding reference wavelength and/or difference images indicative of various severity levels of gastric cancer in the database to identify similar reference images in order to diagnose the subject with a particular severity level (e.g., stage) of gastric cancer. Although FIG. 27A only shows comparing difference images, wavelength images and white light images that have not been processed as a difference image can also be used in the comparison. Similarly, the subject images are compared to multiple reference images indicative of various severities of gastric cancer, not just the relevant severity 2 (e.g., stage II) reference images shown in FIG. 27A.

Then, the subject images are compared to a plurality of corresponding reference images in the database to identify reference images with similar feature patterns, and determine the severity of gastric cancer of the subject. The feature patterns may include microvascular patterns and the size and depth of lesions. By acquiring multiple images, different layers of the stomach can be imaged for determining how deep the cancer has invaded into the stomach in order to facilitate making an accurate diagnosis of the severity. In FIG. 27A, feature patterns, such as blood vessels and feature points based on the thickness of bloods vessels and position of the blood vessels/branches, have been extracted from the images to facilitate the comparison between the subject images and the reference images for making an accurate diagnosis of the severity.

Alternatively, the database shown in FIG. 27A may be an AI database in which multiple reference images indicative of various severities (e.g., stages) of gastric cancer have been accumulated. The reference images collected in the database are used to train an AI model, such as a deep learning model, e.g., a convolutional neural network. The reference images are labeled as representing a particular severity (e.g., stage) of gastric cancer or as representing a normal or healthy stomach free of gastric cancer. Gastric cancer diagnosis and severity may be assigned to the reference images based on the results of diagnostic imaging or tissue diagnosis. Severity labeling begins with imaging or histological diagnosis by a doctor and metastasis to lymphatic vessels or other organs by CT and/or MRI. The model learns feature patterns corresponding to gastric cancer and a severity thereof from the reference images collected in the database. For example, such feature patterns may include microvascular patterns, such as blood vessels and feature points based on the thickness, branching, and position of bloods vessels and the number of blood vessels per area, occupation rate, topography (e.g., unevenness) of surface of stomach wall and color (e.g., redness), and malformations. Once the model has been sufficiently trained, a learned model is created.

When a subject image is input into the learned model, the learned model can identify the severity of gastric cancer from the subject image based on the learned feature patterns from training on the plurality of reference images in the database. The learned model extracts features from the subject images and outputs a severity (e.g., stage) diagnosis based on the feature patterns. Accuracy and consistency of diagnoses can be improved by the use of AI to extract feature patterns related to the severity of gastric cancer based on a training model of multiple reference images.

The diagnosis may also be made by taking other data and analysis into consideration, including non-image data, such as family history, clinical data, laboratory data, subject history, family history, subject vital signs, results of various tests (e.g., genetic tests), and any other relevant non-image data. The various images and data described herein may be stored in one or more databases to facilitate subsequent data analysis. Moreover, any or all of the comparisons may be performed either automatically by a data processing system, such as system 10, or by a medical professional, such as a doctor, or by some combination thereof, to facilitate automatic or manual diagnosis of the subject.

Figure 27B:
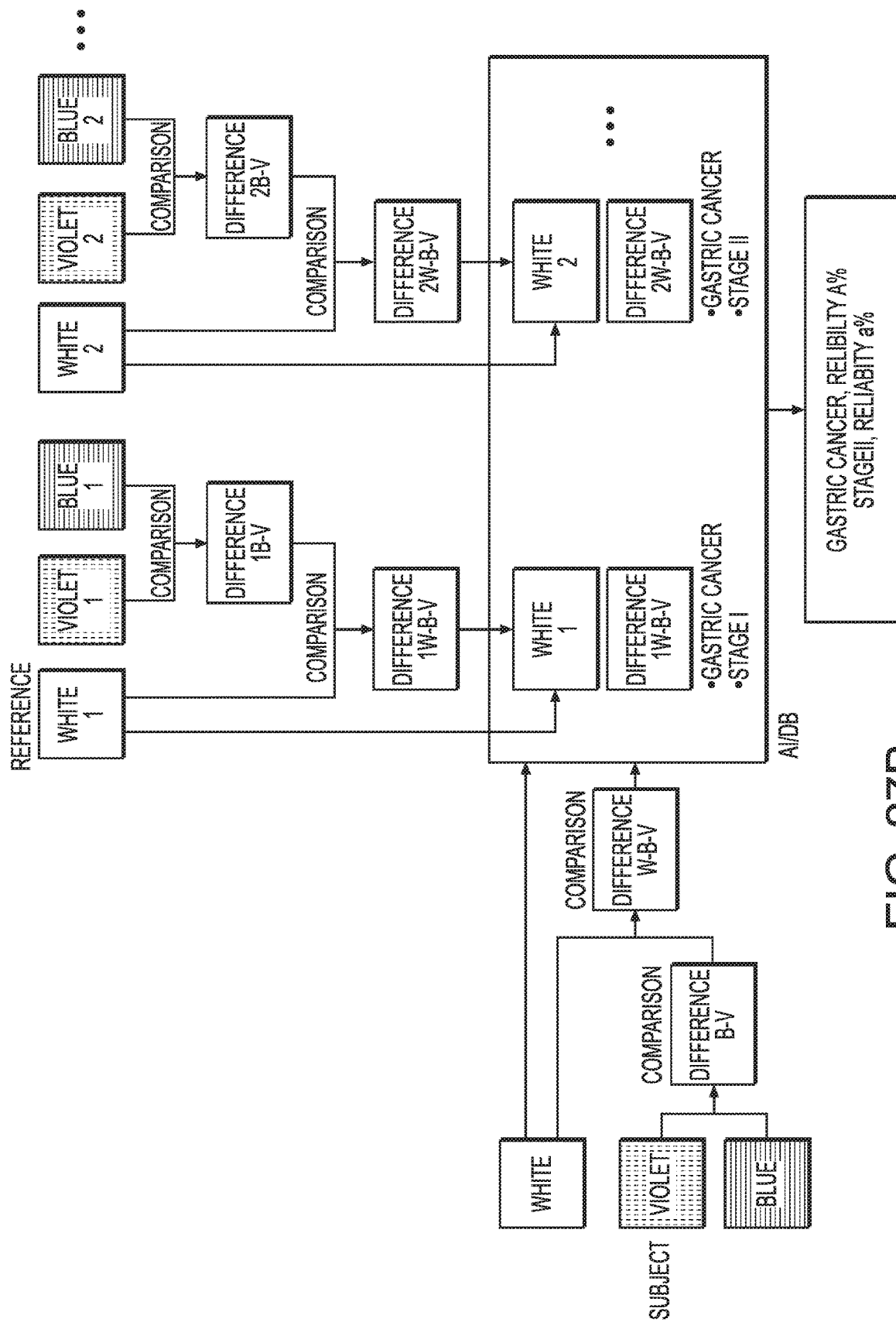

FIG. 27B shows an exemplary method in which the mucosal layer is examined and diagnosed as showing Stage II gastric cancer using white light, blue light, and purple light images. White light, blue light, and purple light images of a subject's stomach wall are obtained. An image obtained by white light (e.g., wavelength band of 340-700 nm) can show unevenness or color of the surface of tissue. Blue light (e.g., wavelength band of 390-445 nm) can reach the mucosal layer of the stomach wall and is further absorbed and/or reflected by hemoglobin. Blue light (e.g., wavelength band of 390-445 nm) can delineate blood vessels in the superficial layer of the mucosal layer. The purple light (e.g., wavelength band of 265-310 nm) can reach the surface layer of the stomach wall (the surface layer of the mucosal layer), and is further absorbed and/or reflected by hemoglobin. Purple light (e.g., wavelength band of 265-310 nm) can delineate blood vessels in the superficial layer of the mucosal layer.

A difference image (difference b-v in FIG. 27B) is generated by subtracting the purple light image from the blue light image. The difference image b-v is a blood vessel image of the mucosal layer (a blood vessel image obtained by removing the surface layer of the mucosal layer from the mucosal layer).

Further, a difference image (difference w-b-v in FIG. 27B) is created by subtracting the difference image (difference b-v) from the white light image. The surface of the stomach wall contains digestive enzymes (e.g., amylase, protease, lipase, maltase) and saline. Therefore, the surface of the stomach wall is highlighted by digestive enzymes and physiological saline present on the surface of the gastric juice. As a result, surface highlighting also occurs in acquired white light images. The surface highlighting can be deleted by subtracting the difference image (difference b-v) from the white light image.

In the same manner as described above, reference images (e.g., white 1, white 2, difference 1w-b-v, difference 2w-b-v, ...) indicative of specific severities (e.g., stages) of gastric cancer are stored in the database. The reference images includes a white light image (white 1, white 2, ...) and difference images (difference 1w-b-v, difference 2w-b-v, ...) generated from reference wavelength images. Further, the reference images (difference image, white light image) accumulated in the database are each associated (e.g., labeled) with their diagnosis result (e.g., presence or absence of stomach cancer, severity (stage)). Although the database in FIG. 27B only shows Stage I and Stage II images as exemplary reference images, the database preferably contains multiple images representative of all the various stages of gastric cancer, as well as images showing normal (healthy) stomachs that do not have gastric cancer.

Then, in FIG. 27B, diagnoses are performed by comparing the reference images (difference images, white light images) stored in the database with the subject wavelength image (e.g., white light image) and difference image (e.g., difference w-b-v). Diagnosis includes an assessment of stomach cancer, reliability of gastric cancer assessment (A %), severity (stage) (e.g., Stage II), and reliability of stage assessment (a %).

"Reliability" refers to, for example, how many patients who are judged to be positive for gastric cancer (output results) are confirmed to have gastric cancer by definitive diagnosis. Specifically, it can be calculated by the following equation.

$$\frac{\text{True Positive}}{\text{True Positive} + \text{False Positive}} = \frac{\text{Positive is the number of correct answers}}{\text{Total number of positives}}$$

Similarly, the reliability of stage assessment refers to how many patients who are judged as having a particular stage of gastric cancer are confirmed to have that stage of gastric cancer.

As discussed above, AI (deep learning) may be used instead of comparing the subject images to the references images in the database. In this case, the AI creates a learned model by learning the reference images (difference image, white light image in FIG. 27B) and the diagnosis result (presence or absence of stomach cancer and severity (stage)) associated with each image. Diagnostics are then performed by inputting a difference w-b-v and a white light image of the subject to the learned models. In the case of using AI, learning and diagnosis can be performed with higher accuracy than in the case of learning and diagnosing only with a difference image or only with a white light image by learning and diagnosing using a white light image and a difference image.

Figure 27C:
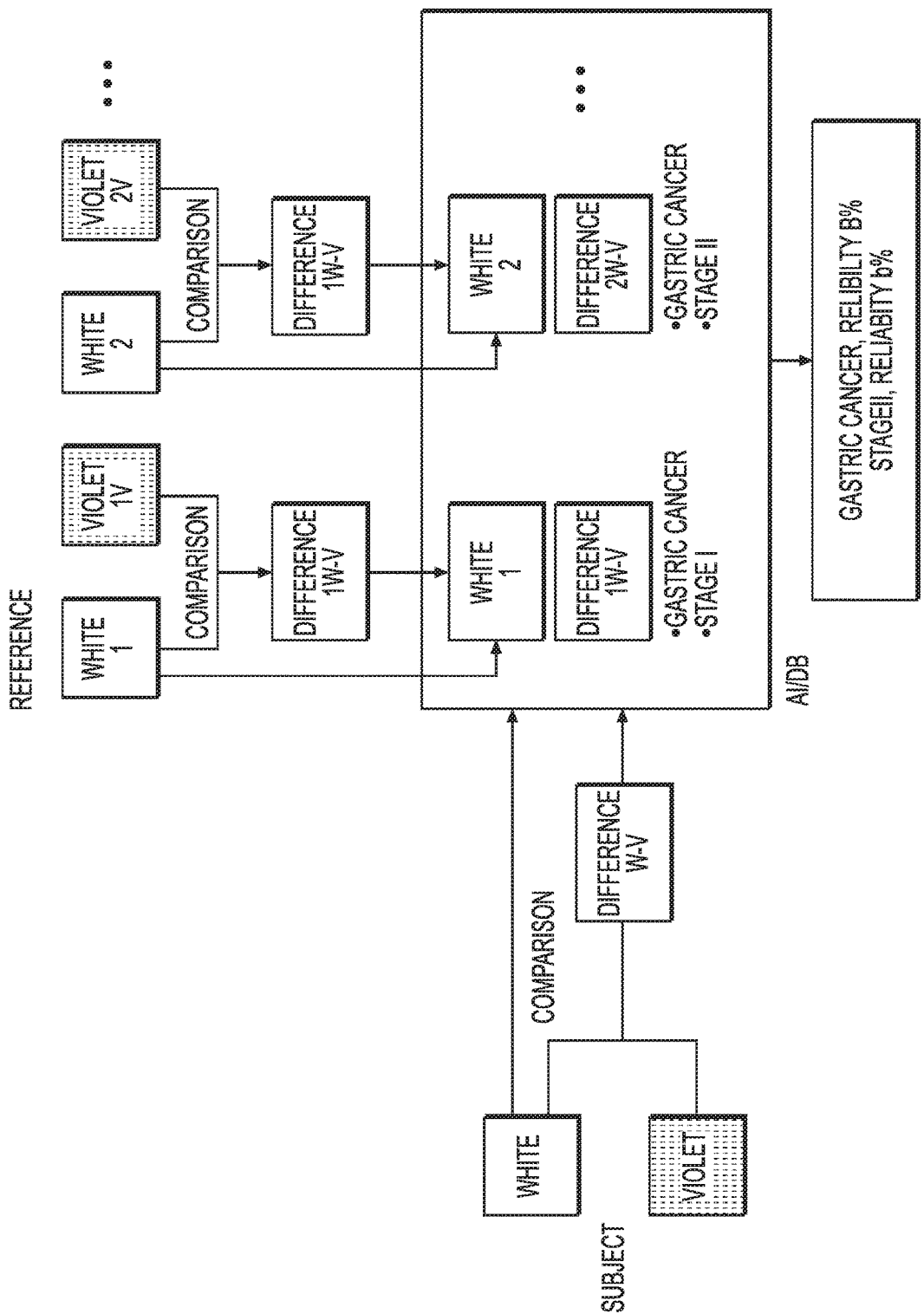

FIG. 27C sows an exemplary method in which the superficial gastric wall is diagnosed as showing Stage II gastric cancer using white light and purple light images. White light and purple light images of a subject's gastric wall are obtained. An image obtained by white light (e.g., wavelength band of 340-700 nm) can show unevenness or color of the surface of tissue. The purple light (e.g., wavelength band of 265-310 nm) reaches the surface layer of the stomach wall (the surface layer of the mucosal layer), and is further absorbed and/or reflected by hemoglobin. That is, purple light (e.g., wavelength band of 265-310 nm) can delineate blood vessels in the superficial layer of the mucosal layer. Therefore, cancer reaching the surface layer of the stomach wall can be diagnosed by an image acquired by purple light. A subject difference image (difference w-v) is created by subtracting the purple light image from the white light image. The mucosal surface layer is delineated by the difference between the white image and the purple image in the subject difference image (difference w-v). In addition, the influence of reflection by the body fluid of the image can be excluded by the difference image.

In the same manner as described above, reference images indicative of particular severities (e.g., stages) of gastric cancer (e.g., white 1, white 2, difference 1w-v, difference 2w-v, . . . ) are stored in the database. The reference images includes a white light image (white 1, white 2, . . . ), and difference images (difference 1w-v, difference 2w-v, . . . ) generated from reference wavelength images. Further, the reference images (difference image, white light image) accumulated in the database are each associated (e.g., labeled) with their diagnosis result (e.g., presence or absence of stomach cancer, severity (stage)). Although the database in FIG. 27C only shows Stage I and Stage II images as exemplary reference images, the database preferably contains multiple images representative of all the various stages of gastric cancer, as well as images showing normal (healthy) stomachs that do not have gastric cancer.

Then, in FIG. 27C, diagnoses are performed by comparing the reference images (difference images, white light images) stored in the database with the subject wavelength image (e.g., white light image) and difference image (e.g., difference w-v). Diagnosis includes an assessment of stomach cancer, reliability of gastric cancer assessment (B %), severity (e.g., stage II), and reliability of stage assessment (b %).

As discussed above, AI (deep learning) may be used instead of comparing the subject images to the references images in the database. In this case, the AI creates a learned model by learning the reference images (difference image, white light image in FIG. 27C) and the diagnosis result (presence or absence of stomach cancer and severity (stage)) associated with each image. Diagnostics are then performed by inputting a difference w-v and a white light image of the subject to the learned models. In the case of using AI, learning and diagnosis can be performed with higher accuracy than in the case of learning and diagnosing only with a difference image or only with a white light image by learning and diagnosing using a white light image and a difference image.

The severity or extent of gastric cancer present on the surface and in multiple layers of the stomach wall may be determined by acquiring multiple images. For example, a severity diagnosis and reliability determination (x %) may be made for each layer of the stomach wall (including the surface) by any of the above methods. The individual severity diagnoses and reliability determinations for the various stomach wall layers may then be compiled and analyzed to determine an overall diagnosis of the stage of gastric cancer. For example, a depth of gastric cancer may be determined from the diagnoses for each layer of the stomach, which is an important feature for diagnosing the stage of gastric cancer. Clinical information regarding metastases may be further taken into consideration to make an overall gastric cancer stage diagnosis.

Figure 28A:
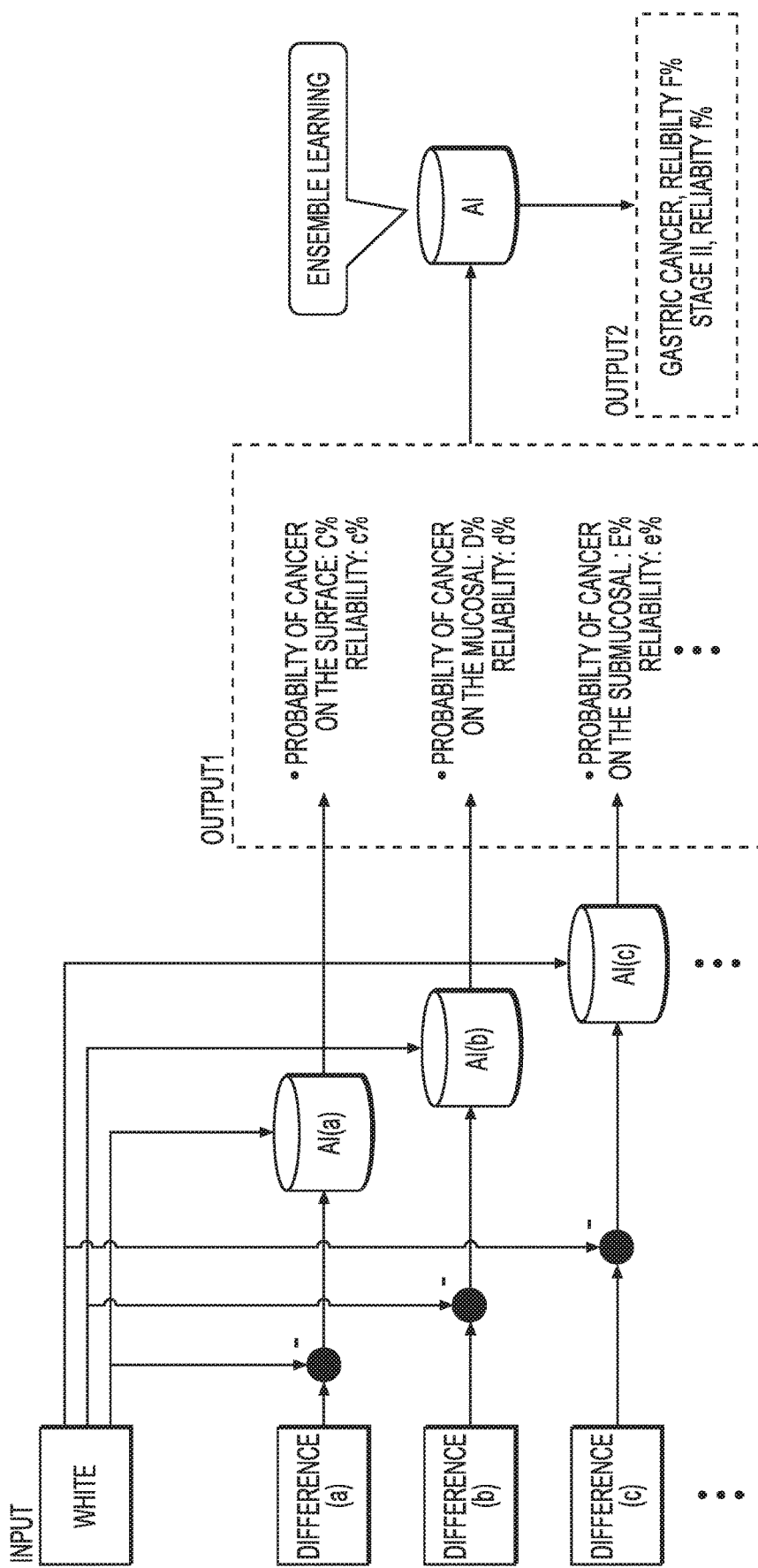
FIGS. 28A and 28B show exemplary ensemble learning models for determining a gastric cancer stage and reliability score.

Alternatively, an ensemble learning AI model may be used to make an overall stage diagnosis based on the diagnoses and reliability determinations for each stomach wall layer (including the surface). FIG. 28A shows an exemplary algorithm for diagnosing the severity (e.g., stage) of gastric cancer based on the severity of gastric cancer in each stomach wall layer. For example, the severity of gastric cancer in individual layers of the stomach wall, such as the superficial gastric wall (see, e.g., FIG. 27B), the muscosal layer (see, e.g., FIG. 27A), the submucosal layer, the muscle layer, and the like, is first determined. The probability (e.g., C %, D %, E %) of cancer on the surface, in the mucosal layer, submucosal layer, muscle layer, and the like and the reliability (e.g., c %, d %, e %) of the diagnoses are output (output 1 in FIG. 28A). The outputs for the individual layers are then input into an ensemble learning AI model to diagnose the subject as either having or not having gastric cancer, and diagnose an overall gastric cancer severity (e.g., stage II) (output 2 in FIG. 28A). The reliability (F %) of the diagnosis of gastric cancer and the reliability (f %) of stage assessment are also output.

Figure 28B:
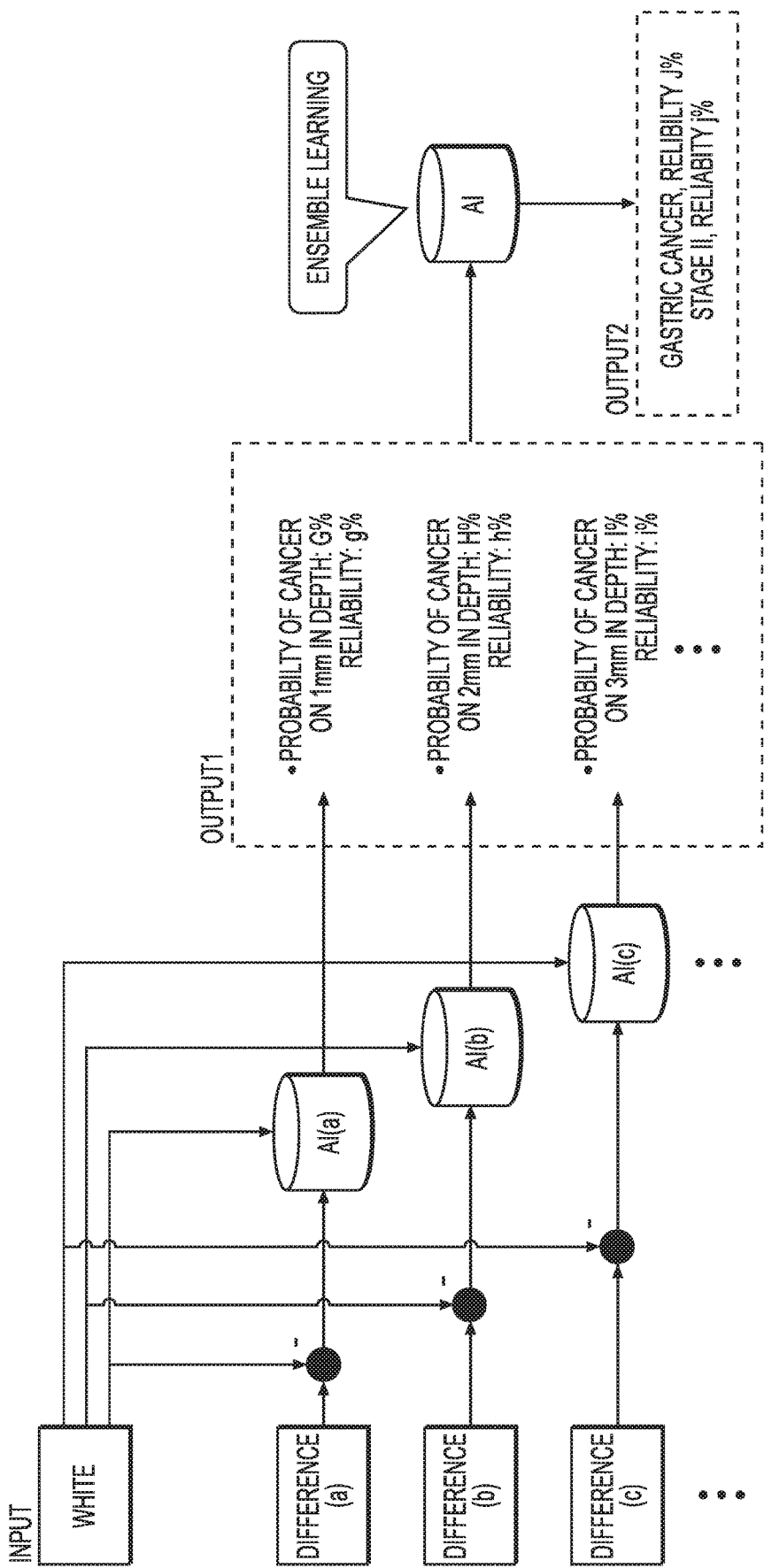

FIG. 28B shows an exemplary algorithm for diagnosing the severity (e.g., stage) of gastric cancer based on the severity of gastric cancer at specific depths within the stomach wall (e.g., 1 mm in depth, 2 mm in depth, . . . ). The severity of gastric cancer at specific depths in the stomach wall can be determined by obtaining images using a laser as the light source, which has a narrower wavelength band than lamp light. For example, ultraviolet light can be used to detect/diagnose very early cancers occurring in the surface layer of the mucosal layer. Near-infrared light can also be used to detect and diagnose cancers that develop in the muscularis (deeper layers of the stomach wall). By determining the precise depth of gastric cancer in the stomach wall, the overall stage of gastric cancer can be accurately diagnosed.

For example, the following steps may be employed to make an overall diagnosis:

(A) Using AI specialized for a white light image and each difference image, whether or not cancer exists at a specific depth is output as a "probability of cancer existing in n-layer" (diagnostic result: stomach cancer probability: G %) and "reliability" (reliability: g %).

(B) Step (A) is performed for a plurality of depths to output the probability (e.g., H % probability at depth of 2 mm) and reliability of the presence of cancer for various depths in the stomach wall (e.g., h % reliability of probability determination for 2 mm depth).

(C) The plurality of results output in (B) ("the existence probability of the cancer of X layer," "the reliability") is output to the AI model trained by ensemble learning, the overall severity (stage) and the reliability are output from a comprehensive viewpoint.

In FIGS. 28A and 28B, each AI (AI(a), AI(b) . . . ) outputs the presence probability and reliability of cancer for each layer or depth of the stomach wall. The output result is input to an ensemble learner (AI). In the AI (ensemble learner), training is performed by learning with teaching. Two types of information may be used for training. The first is the probability and reliability of cancer from each AI (AI(a), AI(b) . . . ) to each layer or depth of the stomach wall. The second is the diagnostic result associated with the reference images. The AI (ensemble learner) weighs the diagnosis result associated with the reference image with the highest coincidence probability by repeatedly attempting while changing the weighting for the input (the existence probability and reliability of cancer for each depth or each layer of the stomach wall) from each AI (AI(a), AI(b), . . . ).

The present systems and methods enable determining the size and/or invasion depth of the cancer into the stomach wall, which can be useful for determining appropriate treatment. For example, the subject images may show relatively small size lesion(s) growing, for example, on the top layer of cells of the mucosa, indicative of low severity gastric cancer. The subject images may show medium sized lesion(s) in the mucosa and/or submucosa, indicative of moderate severity gastric cancer. The subject images may show one or more large lesions in at least the mucosa and submucosa, indicative of high severity gastric cancer.

Determining the size of the lesion by the present systems and methods not only allows the severity of gastric cancer to be accurately diagnosed, but it also permits an appropriate method of treatment be employed. In some embodiments, the system may also output information treatment recommendations based on the diagnosed severity (e.g., stage) of gastric cancer and size and depth of the cancer in the stomach wall. Table 5 shows a method of treatment indicated for each severity level of gastric cancer and lesion size.

TABLE 5

| Lesion Diameter (d) | Gastric Cancer Severity* | Method of treatment |
| --- | --- | --- |
| d ≤ 5 mm | 1 | Hot biopsy |
| 5 mm < d ≤ 20 mm | 2 | EMR** |
| 20 mm < d ≤ 30 mm | 3 | ESD*** |

*1 = low severity; 2 = moderate severity; and 3 = high severity.
**EMR = Endoscopic Mucosal Resection
***ESD = Endoscopic Submucosal Dissection The present methods may include treating the subject based on the determined severity level of gastric cancer. As shown in Table 5, different treatment methods are indicated for different size lesions/different severity levels of gastric cancer. A brief discussion of the various treatment methods follows.

Hot biopsy may be indicated for low severity (1) gastric cancer lesions. For example, hot biopsy may be indicated for micro polyp removal (e.g., having a diameter of 5 mm or less) and can be performed well in the large intestine with many small polyps. Hot biopsy involves removing lesion tissue while supplying high frequency current. Hot biopsy forceps can be used to achieve hemostasis simultaneously with tissue collection. The procedure involves pulling the grasp tissue with the forceps such that the root of the lesion is thin and stretched, and passing high frequency current in this state. The current is concentrated in the stretched tissue area, and the tissue is ablated and whitened. After confirmation of tissue whitening, the tissue is torn and removed for collection.

Endoscopic Mucosal Resection (EMR) may be indicated for moderate severity (2) gastric cancer lesions. For instance, EMR may be indicated for removal of lesions having a diameter larger than 5 mm. For example, the lesion may have a size in a range of from 5 to 20 mm. EMR may involve a submucosal injection under the lesion, snaring, and removing the lesion. For example, physiological saline may be injected into the submucosal layer of a flat lesion to make it bulge. Then, the root of the raised lesion may be surrounded by a high frequency snare. While raising the snare, the snare is tightened (e.g., squeezed) around the root of the raised lesion and high frequency current is applied to the lesion to cauterize and excise the lesion tissue.

Endoscopic Submucosal Dissection (ESD) may be indicated for high severity (3) gastric cancer lesions. For example, ESD may be indicated for removal of lesions having a diameter larger than 5 mm or even larger than 20 mm. ESD may be used to remove lesions up to about 30 mm or more. ESD allows en bloc resection of larger lesions. ESD may involve submucosal injection, circumferential mucosal precutting and dissection. For example, ESD may involve marking around the lesion, injecting physiological saline into the submucosal layer of the lesion (e.g., to raise the lesion), incising the perimeter of the lesion, and removing the incised submucosal layer to remove the entire lesion.

As mentioned above, gastric cancer stage may be determined based on the penetration depth of gastric cancer in the layers of the stomach and metastasis information. Subject images (e.g., wavelength and difference images) may be acquired for each layer of the stomach to determine whether the cancer is present in the each of the layers of the stomach, such as the gastric wall surface, the mucosal layer, submucosal layer, and muscle layer. The images may images of various bands of light, including, for example, blue light, green light, red light, white light, and infrared bands of light, as well as difference images obtained by subtracting various images from one another, adding various images together, and combinations thereof, such as addition/subtraction images in which one image is added to another and then a third image is subjected from the addition image.

For example, with reference to FIG. 24, the subject wavelength images may show cancer cells 988 only in the top layer of cells of the mucosa 972, indicative of stage 0 gastric cancer. The subject wavelength images may show lesion(s) 990 that have grown from the top layer of cells of the mucosa 972 into the next layers below, such as the lamina propria and the muscularis mucosa, which is indicative of stage I gastric cancer. The subject wavelength images may show lesion(s) 992 that have grown from the mucosa 972 into the submucosa 974, indicative of stage II gastric cancer. The subject wavelength images may show lesion(s) 994 that have grown from the mucosa 972 to the muscle layer 976, indicative of stage III gastric cancer. The subject wavelength images may show lesion(s) 996 that have grown from the mucosa 972 deep into the muscle layer 976, indicative of stage IV gastric cancer. Finally, the subject wavelength image may show lesion(s) 998 that are present in the submucosal layer 974 or muscle layer 976, but are not present in the mucosal layer 972, which is indicative of Scirrhous stomach cancer. Therefore, the subject may be diagnosed with stage 0-IV gastric cancer or Scirrhous stomach cancer based on a depth of lesion(s) in the stomach layers. The methods and systems may also use electronic medical record information, regarding, for example, whether the cancer has metastasized to facilitate the diagnosis of the severity (e.g., stage) of gastric cancer, in combination with, for example, the depth and/or size of lesions in the subject stomach.

In particular, the diagnoses of gastric cancer stages may be further facilitated by non-image data, such as information concerning whether the cancer has spread to nearby lymph nodes or whether the cancer has spread to distant sites (metastasis). For example, such metastasis information in combination with the above gastric cancer depth and size information can be used to precisely diagnose the stage of gastric cancer. For example, if the tumor has grown from the top layer of cells of the mucosa 972 into the next layers below such as the lamina propria, the muscularis mucosa, or submucosa 974, but has not spread to nearby lymph nodes or to distant sites, then the subject may be diagnosed with stage IA gastric cancer. On the other hand, if the tumor is the same size, but the cancer has spread to 1 to 2 nearby lymph nodes (and has not spread to distant sites), then the subject may be diagnosed with stage IIB gastric cancer.

Thus, the subject images may be used to determine the size and/or invasion depth of gastric cancer in the stomach layers to accurate diagnose the severity (e.g., stage) of gastric cancer. The present systems can further take into account information regarding metastasis of the cancer for accurately diagnosing the stage of gastric cancer.

Reference data, including image data and non-image data, may be collected from people or groups of people. Such people may include healthy people that are not suffering from gastric cancer, and other people suffering from different severity levels of gastric cancer. The reference image and non-image data may be standardized and categorized according to one or more characteristics, as discussed above. For example, such reference data may be categorized based on population characteristics, such as race, gender, or age of the people from which the data was collected. Standardized data permits average stomach characteristics to be calculated for healthy subjects and subjects with different severity levels of gastric cancer.

The exemplary diagnostic processor system 10 shown in FIG. 1 may be used to facilitate diagnosis of the severity (e.g., stage) of gastric cancer of the subject. For example, computer-readable instructions for analyzing and/or processing images and data, generating difference images, calculating reliability scores, performing or facilitating diagnosis of a particular severity level (e.g., stage) of gastric cancer may be stored in the storage device 14, such as the memory. The processor 12 may execute the computer-readable instructions to facilitate diagnosis of the subject. As an output device 18, a display may be configured to display one or more of: the subject image, generated difference images, the reference images, non-image subject data, and the diagnosis received from the processor, including the reliability score.

Based on the diagnosis of the severity (e.g., stage) of gastric cancer, the subject may be appropriately treated. The processor may determine which treatment is appropriate based on the severity (e.g., stage) of gastric cancer and output treatment information accordingly. For example, some small stage 0 and stage IA cancers may be treated by endoscopic resection. Other stage 0 and stage I gastric cancers may be treated by surgery to remove the tumor(s), such as by subtotal or total gastrectomy, in which part or all of the stomach is removed, along with nearby lymph nodes. All stages of gastric cancer may additionally or alternatively be treated by chemotherapy or chemoradiation to shrink the cancer. In some cases, a laser beam directed through an endoscope (a long, flexible tube passed down the throat) can be used to destroy the tumor and relieve obstruction without surgery. If needed, a stent may be placed where the esophagus and stomach meet to help keep it open and allow food to pass through it. This can also be done at the junction of the stomach and the small intestine. Targeted therapy can also be helpful in treating advanced gastric cancers. For example, Trastuzumab can be added to chemotherapy for subjects with tumors that are HER2-positive. Ramucirumab may also be used by itself or with chemotherapy. Pembrolizumab, which is an immunotherapy drug, may also be administered.

Exemplary treatments based on gastric cancer depth and metastasis are shown in Table 6 below.

TABLE 6

Treatment Based on Depth and Metastasis

| Depth | | No metastasis | Metastasis to lymph node | Metastasis to distant place |
|---|---|---|---|---|
| T1 (M) | Mucosal layer | EMR | Surgery → Chemotherapy | Chemotherapy |
| T1 (SM) | Submucosal layer | Surgery → Chemotherapy | Surgery → Chemotherapy | |
| T2 | Muscular layer | Surgery → Chemotherapy | Surgery → Chemotherapy | |
| T3 | Over muscular layer | Surgery → Chemotherapy | Chemotherapy → Surgery | |
| T4 | Appears on the surface of the stomach | Chemotherapy → Surgery | Chemotherapy → Surgery | |

In some instances, the treatment recommendation output by the processor may include instructions to perform Computed Tomography (CT) examination and/or Magnetic Resonance Imaging (MRI) examination. For example, when the diagnosis result (severity) suggests that the cancer may have metastasized to another organ, the processor may be programmed to output a treatment recommendation that includes performing a CT and/or MRI to confirm whether the cancer has metastasized to another organ.

Some embodiments may employ systems and methods for image analytics using machine learning. For example, the images, including wavelength and difference images, the diagnosis (e.g., gastric cancer stage, reliability score), and medical record information (e.g., information of patient's age, gender, nationality, medical history, and other tests, such as X-ray imaging examination, CT examination, MRI examination, PET examination, ultrasound examination, pathological examination results, or the like) may be input into a system, such as the system 10 (FIG. 1). The system may be configured to execute a program to "learn" the image and the cancer diagnosis, and determine a relationship between the image and the cancer. For example, the program may be taught to analyze images by providing the program with training information that includes previously-analyzed images and associated diagnoses, as well as other relevant clinical, demographic, and external data. The system may learn the image and the diagnosis (e.g., cancer stage), and determine a relationship between the image and the diagnosis (e.g., cancer stage). The system may also learn the image, the cancer, and the stage, and the medical record information to determine each relationship.

Technical effects of the present disclosure include the accurate and consistent diagnoses of various gastric conditions and severity levels thereof, as well as providing decision support tools for user-diagnosis of subjects. For example, technical effects may include the visualization of subject image and non-image information together in a holistic, intuitive, and uniform manner, facilitating accurate and objective diagnosis by a user. Additionally, the present systems, methods, and computer-readable media enable the generation of subject abnormality images and reference abnormality images of known gastric conditions and/or severity levels thereof, and the combination of such images with other clinical tests, to facilitate quantitative assessment and diagnosis of gastric conditions and their severity level. The disclosed systems, methods, and computer-readable media enable analysis of multiple parameters, including both image and non-image data, to accurately and objectively diagnose severity levels of gastric conditions.

It will be appreciated that any of the above-disclosed and other features and functions, or alternatives thereof, may be desirably combined into many other different systems or applications. Also, various presently unforeseen or unanticipated alternatives, modifications, variations, or improvements therein may be subsequently made by those skilled in the art, and are also intended to be encompassed by the following claims.

What is claimed is:

1. A diagnostic system for determining a severity of gastric cancer in a subject, comprising:
    a processor programmed to:
        obtain subject images of a stomach of a subject collected by an endoscope including a first wavelength image of a first wavelength band and a second wavelength image of a second wavelength band,
        generate a subject difference image by subtracting the second wavelength image from the first wavelength image, the first wavelength band being longer than the second wavelength band,
        compare the subject difference image with corresponding reference images representative of different severity levels of gastric cancer stored in a database, or input the subject difference image into a learned model trained using the reference images stored in the database to extract a feature pattern corresponding to a severity level of gastric cancer; and
        diagnose the subject as having a particular severity level of gastric cancer.

2. The diagnostic system according to claim 1, wherein the reference images include: reference wavelength images of different wavelength bands, and reference difference images obtained from the reference wavelength images.

3. The diagnostic system according to claim 1, wherein a plurality of subject difference images are generated from different subject wavelength images of different wavelength bands.

4. The diagnostic system according to claim 1, wherein the processor is further programmed to compare a subject wavelength image with corresponding reference images or input the subject wavelength image into the learned model.

5. The diagnostic system according to claim 1, wherein the processor is further programmed to determine a severity level of gastric cancer for each of multiple layers of a wall of the stomach of the subject by comparing a plurality of subject images with corresponding reference images.

6. The diagnostic system according to claim 5, wherein the severity level of gastric cancer is determined for each of a mucosal layer, submucosal layer, and muscle layer of the wall of the stomach of the subject.

7. The diagnostic system according to claim 5, wherein the subject is diagnosed as having the particular severity level of gastric cancer based on the severity level of gastric cancer for each of the multiple layers of the wall of the stomach.

8. The diagnostic system according to claim 1, wherein the processor is further programmed to determine severity levels of gastric cancer at various depths a wall of the stomach of the subject by comparing a plurality of subject images with corresponding reference images.

9. The diagnostic system according to claim 1, wherein the processor is further programmed to output treatment recommendation based on the diagnosis of the severity level of gastric cancer.

10. The diagnostic system according to claim 1, wherein the processor is further programmed to recommend a Computerized Tomography (CT) examination or Magnetic Resonance Imaging (MRI) examination to determine whether cancer has metastasized to another organ based on the diagnosis of the severity level of gastric cancer.

11. A method for determining a severity of gastric cancer in a subject, comprising:
    obtaining subject images of a stomach of a subject collected by an endoscope including a first wavelength image of a first wavelength band and a second wavelength image of a second wavelength band,
    generating, via a processor, a subject difference image by subtracting the second wavelength image from the first wavelength image, the first wavelength band being longer than the second wavelength band,
    comparing, via the processor, the subject difference image with corresponding reference images representative of different severity levels of gastric cancer stored in a database, or inputting the subject difference image into a learned model trained using the reference images stored in the database to extract a feature pattern corresponding to a severity level of gastric cancer; and
    diagnosing, via the processor, the subject as having a particular severity level of gastric cancer.

12. The method according to claim 11, wherein the reference images include: reference wavelength images of different wavelength bands, and reference difference images obtained from the reference wavelength images.

13. The method according to claim 11, wherein a plurality of subject difference images are generated from different subject wavelength images of different wavelength bands.

14. The method according to claim 11, further comprising comparing a subject wavelength image with corresponding reference images or inputting the subject wavelength image into the learned model.

15. The method according to claim 11, further comprising determining a severity level of gastric cancer for each of multiple layers of a wall of the stomach of the subject by comparing a plurality of subject images with corresponding reference images.

16. The method according to claim 15, wherein the severity level of gastric cancer is determined for each of a mucosal layer, submucosal layer, and muscle layer of the wall of the stomach of the subject.

17. The method according to claim 15, the subject is diagnosed as having the particular severity level of gastric cancer based on the severity level of gastric cancer for each of the multiple layers of the wall of the stomach.

18. The method according to claim 11, further comprising determining severity levels of gastric cancer at various depths a wall of the stomach of the subject by comparing a plurality of subject images with corresponding reference images.

19. The method according to claim 11, further comprising treating the subject based on the diagnosis of the severity of gastric cancer.

20. A computer-readable storage medium storing a computer-executable program that causes a computer to perform functions comprising:
- obtaining subject images of a stomach of a subject collected by an endoscope including a first wavelength image of a first wavelength band and a second wavelength image of a second wavelength band,
- generating a subject difference image by subtracting the second wavelength image from the first wavelength image, the first wavelength band being longer than the second wavelength band,
- comparing the subject difference image with corresponding reference images representative of different severity levels of gastric cancer stored in a database, or inputting the subject difference image into a learned model trained using the reference images stored in the database to extract a feature pattern corresponding to a severity level of gastric cancer; and
- diagnosing the subject as having a particular severity level of gastric cancer.

\* \* \* \* \*